(12) United States Patent　(10) Patent No.: US 8,163,935 B2
Aso et al.　(45) Date of Patent: Apr. 24, 2012

(54) FUSED HETEROCYCLIC COMPOUNDS

(75) Inventors: Kazuyoshi Aso, Osaka (JP); Michiyo Mochizuki, Osaka (JP); Albert Charles Gyorkos, Westminster, CO (US); Christopher Peter Corrette, Boulder, CO (US); Suk Young Cho, Gyeonggi-Do (KR); Scott Alan Pratt, Boulder, CO (US); Christopher Stephen Siedem, Boulder, CO (US)

(73) Assignee: Takeda Pharmaceutical Company Limited, Osaka (JP)

( * ) Notice: Subject to any disclaimer, the term of this patent is extended or adjusted under 35 U.S.C. 154(b) by 1041 days.

(21) Appl. No.: 11/919,435

(22) PCT Filed: Apr. 26, 2006

(86) PCT No.: PCT/US2006/015646
§ 371 (c)(1),
(2), (4) Date: Dec. 12, 2007

(87) PCT Pub. No.: WO2006/116412
PCT Pub. Date: Nov. 2, 2006

(65) Prior Publication Data
US 2009/0312383 A1　Dec. 17, 2009

Related U.S. Application Data

(60) Provisional application No. 60/675,113, filed on Apr. 27, 2005, provisional application No. 60/742,101, filed on Dec. 2, 2005.

(51) Int. Cl.
C07D 403/02　(2006.01)
C07D 235/24　(2006.01)
C07D 235/26　(2006.01)
C07D 235/30　(2006.01)
A61K 31/415　(2006.01)

(52) U.S. Cl. ............... 548/306.1; 548/306.4; 548/307.4; 514/395

(58) Field of Classification Search ........................ None
See application file for complete search history.

(56) References Cited

U.S. PATENT DOCUMENTS

| | | | |
|---|---|---|---|
| 6,124,463 A | 9/2000 | Beck et al. | |
| 6,358,978 B1 | 3/2002 | Ritzeler et al. | |
| 6,376,664 B1* | 4/2002 | Chan et al. ................. | 540/465 |
| 7,714,009 B2* | 5/2010 | Gyorkos et al. .............. | 514/388 |
| 2002/0016460 A1 | 2/2002 | Snow et al. | |
| 2002/0132842 A1 | 9/2002 | Hofmeister et al. | |
| 2003/0191170 A1 | 10/2003 | Hofmeister et al. | |
| 2004/0006119 A1 | 1/2004 | Lang et al. | |
| 2004/0122237 A1 | 6/2004 | Amiri et al. | |
| 2004/0242560 A1 | 12/2004 | Heinelt et al. | |
| 2005/0042212 A1 | 2/2005 | Nanda et al. | |
| 2006/0160872 A1 | 7/2006 | Norman et al. | |
| 2007/0021456 A1 | 1/2007 | Mitjans et al. | |
| 2007/0066660 A1 | 3/2007 | Stahle et al. | |
| 2007/0135452 A1* | 6/2007 | Gyorkos et al. ............ | 514/259.2 |
| 2009/0186879 A1* | 7/2009 | Aso et al. ..................... | 514/220 |
| 2010/0041891 A1* | 2/2010 | Setoh et al. ................ | 546/281.1 |
| 2010/0048658 A1* | 2/2010 | Aso et al. ..................... | 514/395 |

FOREIGN PATENT DOCUMENTS

| | | |
|---|---|---|
| EP | 1 342 489 | 9/2003 |
| WO | 97/48697 | 12/1997 |
| WO | WO 9805327 A1 * | 2/1998 |
| WO | 00/01697 | 1/2000 |
| WO | 01/00611 | 1/2001 |
| WO | 01/21160 | 3/2001 |
| WO | 01/25238 | 4/2001 |
| WO | 01/97786 | 12/2001 |
| WO | 02/14319 | 2/2002 |
| WO | 02/49629 | 6/2002 |
| WO | WO 02062771 A1 * | 8/2002 |
| WO | 02/092575 | 11/2002 |
| WO | 03/053961 | 7/2003 |
| WO | 03/082272 | 10/2003 |
| WO | 2004/043913 | 5/2004 |
| WO | 2004/099148 | 11/2004 |
| WO | 2005/002520 | 1/2005 |
| WO | 2005/044793 | 5/2005 |
| WO | 2005/058870 | 6/2005 |
| WO | 2005/058871 | 6/2005 |
| WO | 2005/058873 | 6/2005 |
| WO | 2005/065680 | 7/2005 |
| WO | 2005/070920 | 8/2005 |
| WO | 2005/077936 | 8/2005 |
| WO | 2006/099379 | 9/2006 |
| WO | 2008/013270 | 1/2008 |

OTHER PUBLICATIONS

Jonas et al, European Journal of Medicinal Chemistry (1993), vol. 28(2), 141-148.*

(Continued)

Primary Examiner — Kamal Saeed
Assistant Examiner — Nyeemah A Grazier
(74) Attorney, Agent, or Firm — Wenderoth, Lind & Ponack, L.L.P.

(57) ABSTRACT

There is provided a CRF receptor antagonist comprising a compound of the formula (I):

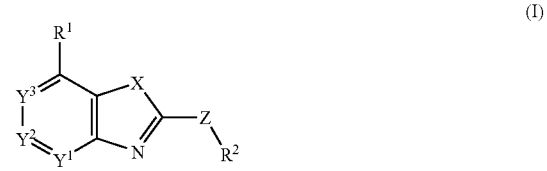

wherein $R^1$ is an optionally substituted hydrocarbyl, an optionally substituted C-linked heterocyclic group, an optionally substituted N-linked heteroaryl group, a cyano or an acyl; $R^2$ is an optionally substituted cyclic hydrocarbyl or an optionally substituted heterocyclic group; X is oxygen, sulfur or —$NR^3$— (wherein $R^3$ is a hydrogen, an optionally substituted hydrocarbyl or an acyl); $Y^1$, $Y^2$ and $Y^3$ are each an optionally substituted carbon or a nitrogen, provided that one or less of $Y^1$, $Y^2$ and $Y^3$ is nitrogen; and Z is a bond, —CO—, oxygen, sulfur, —SO—, —$SO_2$—, —$NR^4$—, —$NR^4$-alk-, —$CONR^4$— or —$NR^4CO$— (wherein alk is an optionally substituted $C_{1-4}$ alkylene and $R^4$ is a hydrogen, an optionally substituted hydrocarbyl or an acyl); or a salt thereof or a prodrug thereof.

20 Claims, No Drawings

OTHER PUBLICATIONS

Alexander Kiselyov, Tetrahedron Letters (1999), 40(22), 4119-4122.*

X. Wang et al., "A practical synthesis of 2-(N-substituted)-aminobenzimidazoles utilizing CuCl-promoted intramolecular cyclization of N-(2-aminoaryl)thioureas", Tetrahedron Letters, vol. 45, pp. 7167-7170, 2004.

R. J. Snow et al., "Isoquinolinone synthesis by $S_NAr$ reaction: a versatile route to imidazo[4,5-h]isoquinolin-9-ones", Tetrahedron Letters, vol. 43, pp. 7553-7556, 2002.

D. R. Goldberg et al., "Optimization of 2-phenylaminoimidazo[4,5-h]isoquinolin-9-ones: orally active inhibitors of Ick kinase", J. Med. Chem., vol. 46, pp. 1337-1349, 2003.

F. Jung et al., "Synthesis and structure-activity relationship of new cephalosporins with amino heterocycles at C-7. Dependence of the antibacterial spectrum and β-lactamase stability on the $pK_a$ of the C-7 heterocycle", J. Med. Chem., vol. 34, No. 3, pp. 1110-1116, 1991.

R. Chen et al. "Expression cloning of a human corticotropin-releasing-factor receptor", Proc. Natl. Acad. Sci. USA, vol. 90, pp. 8967-8971 (Oct. 1993).

Supplementary Partial European Search Report issued Jul. 14, 2008.

Search Report issued Oct. 8, 2008 from National Centre of the Intellectual Property "Sakpatenti" of Georgia in the Georgian Application No. AP 2006 010339 of which the present application corresponds.

Taiwanese Office Action issued Aug. 30, 2011 in corresponding Taiwanese Application No. 095114290, with English translation.

* cited by examiner

FUSED HETEROCYCLIC COMPOUNDS

This application is a U.S. national stage of International Application No. PCT/US2006/015646 filed Apr. 26, 2006 which claims the benefit of U.S. Provisional Application No 60/675,113, filed Apr. 27, 2005 and claims the benefit of U.S. Provisional Application No. 60/742,101, filed Dec. 2, 2005.

TECHNICAL FIELD

The present invention relates to novel nitrogen-containing fused heterocyclic compounds having CRF (corticotropin releasing factor) antagonistic activity and pharmaceutical compositions containing them.

BACKGROUND ART

Corticotropin-releasing factor (hereinafter, abbreviated as "CRF") is a neuropeptide composed of 41 amino acids, and was isolated and purified as a peptide promoting release of adrenocorticotropic hormone (ACTH) from pituitary gland. First, the structure thereof was determined from sheep hypothalamus and, thereafter, the presence thereof was confirmed also in a rat or a human, and the structure thereof was determined [Science, 213, 1394 (1981); Proc. Natl. Acad. Sci. USA, 80, 4851 (1983); EMBO J. 5, 775 (1983)]. An amino acid sequence is the same in a human and a rat, but differed in 7 amino acids in ovine. CRF is synthesized as a carboxy-terminal of prepro CRF, cut and secreted. The CRF peptide and a mRNA thereof are present at the largest amount in a hypothalamus and pituitary gland, and are widely distributed in a brain such as cerebral cortex, cerebellum, hippocampus and corpus amygdaloideum. In addition, in peripheral tissues, the existence has been confirmed in placenta, adrenal gland, lung, liver, pancreas, skin and digestive tract [J. Clin. Endocrinol. Metab., 65, 176 (1987); J. Clin. Endocrinol. Metab., 67, 768 (1988); Regul. Pept., 18, 173 (1987), Peptides, 5 (Suppl. 1), 71 (1984)]. A CRF receptor is a 7-transmembrane G protein-coupled receptor, and two subtypes of CRF1 and CRF2 are present. It is reported that CRF1 is present mainly in cerebral cortex, cerebellum, olfactory bulb, pituitary gland and tonsil nucleus. On the other hand, the CRF2 receptor has two subtypes of CRF2α and CRF2β. It was made clear that the CRF2α receptor is distributed much in hypothalamus, septal area and choroids plexus, and the CRF2β receptor is present mainly in peripheral tissues such as skeletal muscle and is distributed in a blood vessel in a brain [J. Neurosci. 15, 6340 (1995); Endocrinology, 137, 72 (1996); Biochim. Biophys. Acta, 1352, 129 (1997)]. Since each receptor differs in distribution in a living body, it is suggested that a role thereof is also different [Trends. Pharmacol. Sci. 23, 71 (2002)].

As a physiological action of CRF, the action on the endocrine system is known in which CRF is produced and secreted in response to stress in hypothalamus and acts on pituitary gland to promote the release of ACTH [Recent Prog. Horm. Res., 39, 245 (1983)]. In addition to the action on the endocrine system, CRF acts as a neurotransmitter or a neuroregulating factor in a brain, and integrates electrophysiology, autonomic nerve and conducts to stress [Brain Res. Rev., 15, 71 (1990); Pharmacol. Rev., 43, 425 (1991)]. When CRF is administered in a cerebral ventricle of experimental animal such as a rat, anxiety conduct is observed, and much more anxiety conduct is observed in a CRF-overexpressing mouse as compared with a normal animal [Brain Res., 574, 70 (1992); J. Neurosci., 10, 176 (1992); J. Neurosci., 14, 2579 (1994)]. In addition, α-helical CRF(9-41) of a peptidergic CRF receptor antagonist exerts an anti-anxiety action in an animal model [Brain Res., 509, 80 (1990); J. Neurosci., 14, 2579 (1994)]. A blood pressure, a heart rate and a body temperature of a rat are increased by stress or CRF administration, but the α-helical CRF(9-41) of a peptidergic CRF antagonist inhibits the increase in a blood pressure, a heart rate and a body temperature due to stress [J. Physiol., 460, 221 (1993)]. The α-helical CRF(9-41) of a peptidergic CRF receptor antagonist inhibits abnormal conducts due to withdrawal of a dependent drug such as an alcohol and a cocaine [Psychopharmacology, 103, 227 (1991); Pharmacol. Rev. 53, 209 (2001)]. In addition, it has been reported that learning and memory are promoted by CRF administration in a rat [Nature, 375, 284 (1995); Neuroendocrinology, 57, 1071 (1993); Eur. J. Pharmacol., 405, 225 (2000)].

Since CRF is associated with stress response in a living body, there are clinical reports regarding stress-associated depression or anxiety. The CRF concentration in a cerebrospinal fluid of a depression patient is higher as compared with that of a normal person [Am. J. Psychiatry, 144, 873 (1987)], and the mRNA level of CRF in hypothalamus of a depression patient is increased as compared with that of a normal person [Am. J. Psychiatry, 152, 1372 (1995)]. A CRF binding site of cerebral cortex of a patient who suicided by depression is decreased [Arch. Gen. Psychiatry, 45, 577 (1988)]. The increase in the plasma ACTH concentration due to CRF administration is small in a depression patient [N. Engl. J. Med., 314, 1329 (1986)]. In a patient with panic disorder, the increase of plasma ACTH concentration due to CRF administration is small [Am. J. Psychiatry, 143, 896 (1986)]. The CRF concentration in a cerebrospinal fluid of a patient with anxiety induced by stress such as obsessive-compulsive neurosis, post-psychic trauma stress disorder, Tourette's syndrome and the like is higher as compared with that of a normal person [Arch. Gen. Psychiatry, 51, 794 (1994); Am. J. Psychiatry, 154, 624 (1997); Biol. Psychiatry, 39, 776 (1996)]. The CRF concentration in a cerebrospinal fluid of schizophrenics is higher as compared with that of a normal person [Brain Res., 437, 355 (1987); Neurology, 37, 905 (1987)]. Thus, it has been reported that there is abnormality in the living body response system via CRF in stress-associated mental disease.

The action of CRF on the endocrine system can be presumed by the characteristics of CRF gene-introduced animal and actions in an experimental animal. In a CRF-overexpressing mouse, excessive secretions of ACTH and adrenal cortex steroid occur, and abnormalities analogous to Cushing's syndrome such as atrophy of muscle, alopecia, infertility and the like are observed [Endocrinology, 130, 3378 (1992)]. CRF inhibits ingestion in an experimental animal such as a rat [Life Sci., 31, 363 (1982); Neuropharmacology, 22, 337 (1983)]. In addition, α-helical CRF(9-41) of a peptidergic CRF antagonist inhibited decrease of ingestion due to stress loading in an experimental model [Brain Res. Bull., 17, 285 (1986)]. CRF inhibited weight gain in a hereditary obesity animal [Physiol. Behav., 45, 565 (1989)]. In a nervous orexia inactivity patient, the increase of ACTH in plasma upon CRF administration is small [J. Clin. Endocrinol. Metab., 62, 319 (1986)]. It has been suggested that a low CRF value is associated with obesity syndrome [Endocrinology, 130, 1931 (1992)]. There has been suggested a possibility that ingestion inhibition and weight loss action of a serotonin reuptake inhibiting agent are exerted via release of CRF [Pharmacol. Rev., 43, 425 (1991)].

CRF is centrally or peripherally associated with the digestive tract movement involved in stress or inflammation [Am. J. Physiol. Gastrointest. Liver Physiol. 280, G315 (2001)]. CRF acts centrally or peripherally, weakens the shrinkablity of stomach, and decreases the gastric excreting ability [Regulatory Peptides, 21, 173 (1988); Am. J. Physiol., 253, G241 (1987)]. In addition, α-helical CRF (9-41) of a peptidergic CRF antagonist has a restoring action for hypofunction of stomach by abdominal operation [Am. J. Physiol., 258, G152 (1990)]. CRF inhibits secretion of a bicarbonate ion in stomach, decreases gastric acid secretion and inhibits ulcer due to cold restriction stress [Am. J. Physiol., 258, G152 (1990)]. Furthermore, α-helical CRF (9-41) of a peptidergic CRF antagonist shows the inhibitory action on gastric acid secretion decrease, gastric excretion decrease, small intestinal transport decrease and large intestinal transport enhancement due to restriction stress [Gastroenterology, 95, 1510 (1988)]. In a healthy person, mental stress increases a gas and abdominal pain due to anxiety and intestine dilation, and CRF decreases a threshold of discomfort [Gastroenterology, 109, 1772 (1995); Neurogastroenterol. Mot., 8, 9 [1996]. In a irritable bowel syndrome patient, large intestinal movement is excessively enhanced by CRF administration as compared with a healthy person [Gut, 42, 845 (1998)].

It has been reported from studies on experimental animals and clinical studies that CRF is induced by inflammation and is involved in a inflammatory reaction. In an inflammatory site of an experimental animal and in a joint fluid of a rheumatoid arthritis patient, production of CRF is topically increased [Science, 254, 421 (1991); J. Clin. Invest., 90, 2555 (1992); J. Immunol., 151, 1587 (1993)]. CRF induces degranulation of a mast cell and enhances the blood vessel permeability [Endocrinology, 139, 403 (1998); J. Pharmacol. Exp. Ther., 288, 1349 (1999)]. CRF can be detected also in a thyroid gland of autoimmune thyroiditis patient [Am. J. Pathol. 145, 1159 (1994)]. When CRF is administered to an experimental autoimmune cerebrospinal meningitis rat, the progression of symptom such as paralysis was remarkably inhibited [J. Immunil., 158, 5751 (1997)]. In a rat, the immune response activity such as T-lymphocyte proliferation and the natural killer cell activity is reduced by CRF administration or stress loading [Endocrinology, 128, 1329 (1991)].

From the above-mentioned reports, it is expected that the CRF receptor antagonistic compound would exert an excellent effect for treating or preventing various diseases in which CRF is involved.

As a CRF antagonist, for example, peptide CRF receptor antagonists are reported in which a part of an amino acid sequence of CRF or associated peptides of a human or other mammals is altered or deleted, and they are reported to show a pharmacological action such as ACTH release-inhibiting action and anti-anxiety action [Science, 224, 889 (1984); J. Pharmacol. Exp. Ther., 269, 564 (1994); Brain Res. Rev., 15, 71 (1990)]. However, from a pharmacokinetic point of view such as chemical stability and absorbability for oral administration in a living body, bioavailability and intracerebral transferability, peptide derivatives have a low utility value as a medicine.

DISCLOSURE OF INVENTION

According to the present invention, there is provided:
(1) A compound represented by the formula (I):

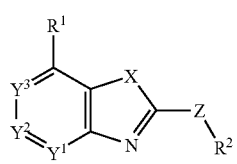

wherein $R^1$ is an optionally substituted hydrocarbyl, an optionally substituted C-linked heterocyclic group, an optionally substituted N-linked heteroaryl group, or an acyl, provided that methyl, and trifluoromethyl are excluded;
$R^2$ is an optionally substituted cyclic hydrocarbyl or an optionally substituted heterocyclic group, provided that 2-[2-(1,1-dimethylethyl)phenyloxy]-3-pyridinyl is excluded;
X is oxygen, sulfur or —$NR^3$— (wherein $R^3$ is a hydrogen, an optionally substituted hydrocarbyl or an acyl);
$Y^1$, $Y^2$ and $Y^3$ are each an optionally substituted carbon or a nitrogen, provided that one or less of $Y^1$, $Y^2$ and $Y^3$ is nitrogen; and
Z is a bond, —CO—, oxygen, sulfur, —SO—, —$SO_2$—, —$NR^4$—, —$NR^4$-alk-, —$CONR^4$— or —$NR^4CO$— (wherein alk is an optionally substituted $C_{1-4}$ alkylene and $R^4$ is a hydrogen, an optionally substituted hydrocarbyl or an acyl);
provided that
(i) the compound wherein X is —NH—, and $R^2$ is an optionally substituted thiophene ring,
(ii) the compound wherein $R^1$ is cyano, $Y^3$ is carbon which is substituted with methyl substituted with three substituents, one of which is acyl, and other two of which may form a ring,
(iii) a) 6-amino-2-[(2,6-dichlorophenyl)amino]-1-methyl-1H-benzimidazole-7-carbonitrile,
b) 6-amino-2-[(2,6-dichlorophenyl)amino]-1-methyl-1H-benzimidazole-7-carboxamide, and
c) 6-{[(allylamino)carbonothioyl]amino}-2-[(2,6-dichlorophenyl)amino]-1-methyl-1H-benzimidazole-7-carboxamide,
(iv) 4-({2-[(4-chlorophenyl)amino]-1,7-dimethyl-1H-benzimidazol-5-yl}oxy)-N-methylpyridine-2-carboxamide,
(v) the compound wherein $R^3$ is substituted heteroarylmethyl, $R^2$ is 4-piperidinyl bearing a substituent at the 1-position,
(vi) the compound wherein $R^2$ is substituted 8-oxo-5-thia-1-aza-bicyclo[4.2.0]oct-2-en-7-yl, and
(vii) 7-ethyl-1-methyl-N-[4-(trifluoromethoxy)phenyl]-5-(trifluoromethyl)-1H-benzimidazol-2-amine and 7-ethenyl-1-methyl-N-[4-(trifluoromethoxy)phenyl]-5-(trifluoromethyl)-1H-benzimidazol-2-amine
are excluded; or a salt thereof;
(2) A prodrug of the compound according to the above-mentioned (1);
(3) The compound according to the above-mentioned (1) wherein $R^1$ is an optionally substituted acyclic branched $C_{3-11}$ hydrocarbyl;
(4) The compound according to the above-mentioned (1) wherein $R^1$ is an optionally substituted $C_{6-10}$ aryl;
(5) The compound according to the above-mentioned (1) wherein $R^1$ is an optionally substituted C-linked 5- to 14-membered heterocyclic group or N-linked 5- to 10-membered heteroaryl group;
(6) The compound according to the above-mentioned (1) wherein X is —$NR^3$— (wherein $R^3$ is as defined in the above-mentioned (1));
(7) The compound according to the above-mentioned (6) wherein $R^3$ is methyl, ethyl or hydroxyethyl;
(8) The compound according to the above-mentioned (1) wherein $Y^1$ is $CR^{3a}$, $Y^2$ is $CR^{3b}$, and $Y^3$ is $CR^{3c}$ (wherein $R^{3a}$, $R^{3b}$ and $R^{3c}$ are independently a hydrogen, a halogen, a nitro, a cyano, an optionally substituted $C_{1-4}$ hydrocarbyl, an optionally substituted $C_{1-4}$ hydrocarbyloxy, an optionally substituted $C_{1-4}$ hydrocarbylthio, an optionally substituted amino or an acyl containing up to 4 carbon atoms;
(9) The compound according to the above-mentioned (8) wherein $R^{3a}$ is a hydrogen, a halogen, a cyano, an optionally substituted $C_{1-3}$ alkyl, or an optionally substituted $C_{1-3}$ alkoxy, $R^{3b}$ is a hydrogen, and $R^{3c}$ is a hydrogen;

(10) The compound according to the above-mentioned (9) wherein $R^{3a}$ is chlorine, bromine, methoxy or methyl;

(11) The compound according to the above-mentioned (1) wherein one of $Y^1$, $Y^2$ and $Y^3$ is nitrogen;

(12) The compound according to the above-mentioned (1) wherein $R^2$ is an optionally substituted $C_{6-10}$ aryl or an optionally substituted 5- to 8-membered heterocyclic group;

(13) The compound according to the above-mentioned (1) wherein $R^2$ is phenyl which is 2,4,6-trisubstituted, 2,4,5-trisubstituted or 2,4-disubstituted;

(14) The compound according to the above-mentioned (1) wherein Z is —$NR^4$— (wherein $R^4$ is as defined in the above-mentioned (1)), or oxygen;

(15) The compound according to the above-mentioned (14) wherein $R^4$ is a hydrogen;

(16) The compound according to the above-mentioned (1) which is
N-(4-chloro-2-methoxy-6-methylphenyl)-7-(2-ethylphenyl)-1-methyl-1H-benzimidazol-2-amine,
N-(4-bromo-2-methoxy-6-methylphenyl)-7-(3,5-diethyl-1H-pyrazol-1-yl)-1-methyl-1H-benzimidazol-2-amine,
N-(4-bromo-2-methoxy-6-methylphenyl)-4-chloro-7-(1-ethylpropyl)-1-methyl-1H-benzimidazol-2-amine,
4-chloro-2-(2,4-dichloro-6-methylphenoxy)-7-(1-ethylpropyl)-1-methyl-1H-benzimidazole,
N-(4-chloro-2-methoxy-6-methylphenyl)-7-(1-ethylpropyl)-1,4-dimethyl-1H-benzimidazol-2-amine, or
2-(2,4-dichloro-6-methylphenoxy)-7-(1-ethylpropyl)-4-methoxy-1-methyl-1H-benzimidazole, or a salt thereof;

(17) A process for producing the compound according to the above-mentioned (1), which comprises reacting a compound represented by the formula:

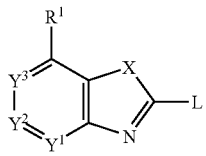

(i)

wherein L represents a leaving group selected from halogen atom, sulfonyloxy group and acyloxy group, and other symbols are as defined in the above-mentioned (1), with a compound represented by the formula:

$$R^2-ZH$$ (ii)

wherein each symbol is as defined in the above-mentioned (1);

(18) A pharmaceutical composition which comprises the compound according to the above-mentioned (1);

(19) A CRF receptor antagonist which is the compound represented by the formula (I'):

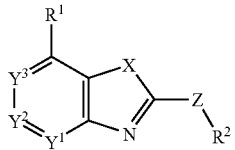

(I')

wherein $R^1$ is an optionally substituted hydrocarbyl, an optionally substituted C-linked heterocyclic group, an optionally substituted N-linked heteroaryl group, a cyano or an acyl;

$R^2$ is an optionally substituted cyclic hydrocarbyl or an optionally substituted heterocyclic group;

X is oxygen, sulfur or —$NR^3$— (wherein $R^3$ is a hydrogen, an optionally substituted hydrocarbyl or an acyl);

$Y^1$, $Y^2$ and $Y^3$ are each an optionally substituted carbon or a nitrogen, provided that one or less of $Y^1$, $Y^2$ and $Y^3$ is nitrogen;

Z is a bond, —CO—, oxygen, sulfur, —SO—, —$SO_2$—, —$NR^4$—, $NR^4$-alk-, —$CONR^4$— or —$NR^4CO$— (wherein alk is an optionally substituted $C_{1-4}$ alkylene and $R^4$ is a hydrogen, an optionally substituted hydrocarbyl or an acyl); or a salt thereof;

(20) A method for treating or preventing a disease wherein a CRF receptor is implicated, which comprises administering to a subject in need thereof an effective amount of the CRF receptor antagonist according to the above-mentioned (19);

(21) The method according to the above-mentioned (20) wherein the disease being treated or prevented is selected from affective disorder, depression or anxiety;

(22) Use of the CRE receptor antagonist according to the above-mentioned (19) for manufacturing a medicament for preventing or treating a disease wherein a CRF receptor is implicated;

(23) The use according to the above-mentioned (22) wherein the disease being treated or prevented is selected from affective disorder, depression or anxiety;

(24) A pharmaceutical composition for preventing or treating a disease wherein a CRF receptor is implicated, which comprises the CRF receptor antagonist according to the above-mentioned (19);

(25) The pharmaceutical composition according to the above-mentioned (24) wherein the disease being treated or prevented is selected from affective disorder, depression or anxiety; and the like.

BEST MODE FOR CARRYING OUT THE INVENTION

In the present specification, the term "hydrocarbyl" means a univalent group containing only carbon and hydrogen.

In the formula (I) and (I'), X represents an oxygen, a sulfur or —$NR^3$— (wherein $R^3$ is a hydrogen, an optionally substituted hydrocarbyl or an acyl). That is, examples of the 5-membered ring in the formula (I) and (I') include an oxazole ring, a thiazole ring and an imidazole ring.

Examples of the "hydrocarbyl" of the "optionally substituted hydrocarbyl" represented by $R^3$ of the formula: —$NR^3$— include an optionally substituted aliphatic hydrocarbon group, an optionally substituted alicyclic hydrocarbon group, an optionally substituted alicyclic-aliphatic hydrocarbon group, an optionally substituted alicyclic-alicyclic hydrocarbon group, an optionally substituted aromatic hydrocarbon group, an optionally substituted aromatic-aliphatic hydrocarbon group (an aralkyl group), and the like.

Examples of said aliphatic hydrocarbon group include a saturated aliphatic hydrocarbon group having 1-8 carbon atoms (e.g., alkyl group) such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; and an unsaturated aliphatic hydrocarbon group having 2-8 carbon atoms (e.g., alkenyl group, alkynyl group, alkadienyl group, alkadiynyl group, etc.) such as vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 2,4-hexadienyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl, 1-heptynyl, 1-octynyl, etc.

Examples of said alicyclic hydrocarbon group include a saturated alicyclic hydrocarbon group having 3-7 carbon atoms (e.g., cycloalkyl group, etc.) such as cyclopropyl, cyclobutyl, cyclopentyl, cyclohexyl, cycloheptyl, and the like; an unsaturated alicyclic hydrocarbon group having 3-7 carbon atoms (e.g., cycloalkenyl group, cycloalkadienyl group, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.; a partly saturated and fused bicyclic hydrocarbon group [preferably, $C_{9-10}$ partly saturated and fused bicyclic hydrocarbon group, etc. (including those where the benzene ring is combined to 5- or 6-membered non-aromatic cyclic hydrocarbon group)] such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc.; and the like. Said alicyclic hydrocarbon group may be cross-linked.

Examples of said alicyclic-aliphatic hydrocarbon group include those where the above-mentioned alicyclic hydrocarbon group and the above-mentioned aliphatic hydrocarbon group are combined, for example, those having 4-14 carbon atoms such as cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphtyl)ethyl, 2-(1,2,3,4-tetrahydro-2-naphtyl)ethyl, 2-(3,4-dihydro-2-naphtyl)ethenyl, etc. (e.g., $C_{3-7}$ cycloalkyl-$C_{1-4}$ alkyl group, $C_{3-7}$ cycloalkenyl-$C_{1-4}$ alkyl group, $C_{3-7}$ cycloalkyl-$C_{2-4}$ alkenyl group, $C_{3-7}$ cycloalkenyl-$C_{2-4}$ alkenyl group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl groups, etc.).

Examples of said alicyclic-alicyclic hydrocarbon group include a $C_{1-4}$ alkyl group substituted with two $C_{3-7}$ cycloalkyls selected from the above-mentioned alicyclic hydrocarbon group, for example, those represented by the formula:

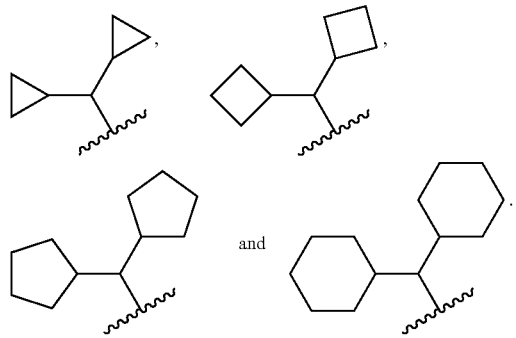

Examples of said aromatic hydrocarbon group include an aryl group having 6-10 carbon atoms (including that where a 5- to 6-membered non-aromatic hydrocarbon ring is fused with phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of said aromatic-aliphatic hydrocarbon group include an aralkyl group having 7-14 carbon atoms ($C_{6-10}$ aryl-$C_{1-4}$ alkyl group) such as phenyl-$C_{1-4}$ alkyl group, e.g., benzyl, phenethyl, 1-phenylethyl, 1-phenylpropyl, 2-phenylpropyl, 3-phenylpropyl, etc.; naphthyl-$C_{1-4}$ alkyl group such as α-naphthylmethyl, α-naphthylethyl, β-naphthylmethyl, β-naphthylethyl, etc.; $C_{6-10}$ aryl-$C_{2-4}$ alkenyl group such as phenyl-$C_{2-4}$ alkenyl group, e.g., styryl, cinnamyl, etc.; and the like.

The above-mentioned "hydrocarbyl" group may have a substituent at a substitutable position. Examples of such substituent include a halogen, nitro, cyano, oxo, (1) an optionally substituted heterocyclic group, (2) an optionally substituted sulfinyl group, (3) an optionally substituted sulfonyl group, (4) optionally substituted hydroxyl group, (5) optionally substituted thiol group, (6) an optionally substituted amino group, (7) an acyl group, (8) an optionally esterified or amidated carboxyl group, (9) an optionally substituted phosphoryl group, or the like.

Examples of the substituent of above-mentioned (2) an optionally substituted sulfinyl group, (3) an optionally substituted sulfonyl group, (4) optionally substituted hydroxyl group, (5) optionally substituted thiol group and (6) an optionally substituted amino group include an optionally substituted hydrocarbyl. Examples of "hydrocarbyl" of such optionally substituted hydrocarbyl include those exemplified above. Such hydrocarbyl may be substituted by one or more substituents at a substitutable position. Examples of the substituent group of the optionally substituted hydrocarbyl as a substituent group include halogen, nitro, cyano, hydroxyl, thiol, amino and carboxyl.

As the optionally substituted sulfinyl group of above-mentioned (2), specifically, $C_{1-6}$ alkylsulfinyl (e.g., methylsulfinyl, ethylsulfinyl, propylsulfinyl, butylsulfinyl etc.) and $C_{6-10}$ arylsulfinyl (e.g., phenylsulfinyl, naphthylsulfinyl etc.) are exemplified.

As the optionally substituted sulfonyl group of above-mentioned (3), specifically, $C_{1-6}$ alkylsulfonyl (e.g., methylsulfonyl, ethylsulfonyl, propylsulfonyl, butylsulfonyl etc.) and $C_{6-10}$ arylsulfonyl (e.g., phenylsulfonyl, naphthylsulfonyl etc.) are exemplified.

As the optionally substituted hydroxyl group of above-mentioned (4), specifically, hydroxyl, $C_{1-6}$ alkoxy (e.g., methoxy, ethoxy, n-propoxy, isopropoxy, n-butoxy, isobutoxy, sec-butoxy, t-butoxy, n-pentyloxy, isopentyloxy, neopentyloxy, etc.) and $C_{6-10}$ aryloxy (e.g., phenoxy, naphthoxy, etc.) are exemplified.

As the optionally substituted thiol group of above-mentioned (5), specifically, thiol, $C_{1-6}$ alkylthio (e.g., methylthio, ethylthio, propylthio, etc.) and $C_{6-10}$ arylthio (e.g., phenylthio, naphthylthio etc.) are exemplified.

As the optionally substituted amino group of above-mentioned (6), specifically, amino, mono-$C_{1-6}$ alkylamino (e.g., methylamino, ethylamino, propylamino, isopropylamino, butylamino etc.), di-$C_{1-6}$ alkylamino (e.g., dimethylamino, diethylamino, ethylmethylamino, dipropylamino, diisopropylamino, dibutylamino etc.), and the like are exemplified.

Examples of the acyl group of above-mentioned (7) include the same group as the acyl for $R^3$.

Examples of the ester group or amide group of the optionally esterified or amidated carboxyl group of above-mentioned (8) include ester group with the same optionally substituted hydrocarbyl as the substituent of optionally substituted hydroxyl group of above-mentioned (4) or amide group with optionally substituted amino group of above-mentioned (6).

As the optionally esterified carboxyl group, specifically, carboxyl, $C_{1-6}$ alkoxy-carbonyl (e.g., methoxycarbonyl, ethoxycarbonyl, propoxycarbonyl, tert-butoxycarbonyl etc.), $C_{6-10}$ aryloxy-carbonyl (e.g., phenoxycarbonyl etc.), $C_{7-16}$ aralkyloxy-carbonyl (e.g., benzyloxycarbonyl, phenethyloxycarbonyl etc.), and the like are exemplified.

As the optionally amidated carboxyl group, specifically, carbamoyl, mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), $C_{6-10}$ aryl-carbamoyl (e.g., phenylcarbamoyl, 1-naphthylcarbamoyl, 2-naphthylcarbamoyl etc.), 5- to 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), and the like are exemplified.

Examples of the "acyl" represented by $R^3$ of the formula: —$NR^3$— include a formyl and a group where the carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group or an aromatic group (e.g., phenyl group, pyridyl group, etc.) (e.g., acetyl, propionyl, butyryl, isobytyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.) and the like.

$R^3$ is preferably hydrogen, $C_{1-10}$ alkyl, $C_{2-10}$ alkenyl, $C_{2-10}$ alkynyl, and more preferably hydrogen, $C_{1-10}$ alkyl.

Specifically, as $R^3$, methyl, ethyl, hydroxyethyl and the like are preferred.

$R^1$ in the formula (I) and (I') is an optionally substituted hydrocarbyl, an optionally substituted C-linked heterocyclic group, an optionally substituted N-linked heteroaryl group, a cyano or an acyl. Here, the term "C-linked" of said "optionally substituted C-linked heterocyclic group" means that $R^1$ is linked via a carbon atom of the heterocyclic group of $R^1$ to the fused bicyclic ring represented by the formula (I). Also, the term "N-linked" of the "optionally substituted N-linked heteroaryl group" means that $R^1$ is linked via a nitrogen atom of the heteroaryl group of $R^1$ to the fused bicyclic ring represented by the formula (I).

Examples of the "optionally substituted hydrocarbyl" for $R^1$ include the same groups as those exemplified with respect to the optionally substituted hydrocarbyl of $R^3$.

Examples of the "optionally substituted heterocyclic group" in the "optionally substituted C-linked heterocyclic group" for $R^1$ include the same groups as those exemplified below with respect to the optionally substituted heterocyclic group of $R^2$.

Examples of the "heteroaryl group" in the "optionally substituted N-linked heteroaryl group" for $R^1$ include a 5- to 10-membered aromatic heterocyclic group optionally containing 1 to 3 hetero atoms selected from a nitrogen atom, a sulfur atom and an oxygen atom in addition to one nitrogen atom (e.g., pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, indolyl, isoindolyl, benzimidazolyl, indazolyl, etc). Said heteroaryl group may be substituted with 1 to 3 substituents selected from the group consisting of halogen, $C_{1-6}$ alkyl, $C_{2-6}$ alkenyl, $C_{1-6}$ alkoxy-$C_{1-6}$ alkyl, $C_{5-7}$ cycloalkyl, $C_{6-10}$ aryl (said aryl may have 1 or 2 substituents selected from halogen, $C_{1-6}$ alkyl, halogeno $C_{1-6}$ alkyl and $C_{1-6}$ alkoxy), $C_{7-14}$ aralkyl (said aralkyl may have 1 or 2 substituents selected from halogen, $C_{1-6}$ alkyl, halogeno $C_{1-6}$ alkyl and $C_{1-6}$ alkoxy), hydroxy, hydroxy-$C_{1-6}$ alkyl, $C_{6-10}$ aryloxy (said aryloxy may have 1 or 2 substituents selected from halogen, $C_{1-6}$ alkyl, halogeno $C_{1-6}$ alkyl and $C_{1-6}$ alkoxy), $C_{7-14}$ aralkyloxy, $C_{6-10}$ aryl-carbonyl, carboxyl, $C_{1-6}$ alkoxy-carbonyl, carbamoyl, $C_{6-10}$ aryl-carbamoyl, amino, $C_{6-10}$ aryl-carbonylamino, $C_{1-6}$ alkyl-carbonylamino, $C_{1-6}$ alkoxy-carbonylamino, $C_{6-10}$ arylthio, $C_{6-10}$ arylsulfonyl, cyano, 5- to 7-membered heterocyclic group and oxo.

Examples of the "acyl" for $R^1$ include the same groups as those exemplified with respect to the acyl of $R^3$.

Among these, $R^1$ in the formula (I) and (I') is preferably an optionally substituted acyclic branched $C_{3-14}$ hydrocarbyl (preferably acyclic branched $C_{3-7}$ hydrocarbyl such as 2-propyl, 3-hexyl, 3-pentyl, 4-heptyl, etc.), an optionally substituted $C_{6-10}$ aryl, an optionally substituted C-linked 5- to 14-membered heterocyclic group or N-linked 5- to 10-membered heteroaryl group.

$R^2$ in the formula (I) and (I') is an optionally substituted cyclic hydrocarbyl or an optionally substituted heterocyclic group.

Examples of the "cyclic hydrocarbyl" of the "optionally substituted cyclic hydrocarbyl" for $R^2$ include a $C_{3-7}$ cycloalkyl group (e.g., cyclopropyl, cyclobutyl, cyclopentyl, cyclohexyl, cycloheptyl, etc), a $C_{3-7}$ cycloalkenyl group (e.g., 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, etc), an aryl group having 6-10 carbon atoms (including that where a 5- to 6-membered non-aromatic hydrocarbon ring is fused with phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of the "heterocyclic" of the "optionally substituted heterocyclic group" for $R^2$ include (i) a 5- to 7-membered heterocyclic group containing one sulfur atom, one nitrogen atom or one oxygen atom, (ii) a 5- to 6-membered heterocyclic group containing 2-4 nitrogen atoms, (iii) a 5- to 6-membered heterocyclic group containing 1-2 nitrogen atoms and one sulfur or oxygen atom, (iv) a 8- to 12-membered fused bicyclic or tricyclic heterocyclic group containing 1-4 heteroatoms selected from nitrogen atom, sulfur atom and oxygen atom, and the like. In addition, each of the heterocyclic groups exemplified in (i) to (iv) may be a saturated or unsaturated heterocyclic group and the unsaturated heterocyclic group may be either aromatic or non-aromatic.

Examples of the heterocyclic group for an optionally substituted heterocyclic group of $R^2$ include an aromatic monocyclic heterocyclic group and a non-aromatic heterocyclic group.

Specific examples of the heterocyclic group for an optionally substituted heterocyclic group include (i) an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.) and (ii) a non-aromatic, heterocyclic group (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.), and (iii) a fused heterocyclic group such as 8- to 12-membered bicyclic or tricyclic heterocyclic group (e.g., benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 1,2,5,6-tetrahydro-4H-pyrrolo[3,2,1-ij]quinolinyl, etc.).

The above-mentioned "cycloalkyl", "cycloalkenyl", "aryl" and "heterocyclic group" in $R^2$ may have the same substituent as those exemplified with respect to the optionally substituted hydrocarbyl group of $R^3$ and further may have the same group as optionally substituted hydrocarbyl group of $R^3$ as their substituent.

In addition, two of the substituents of the "cyclic hydrocarbyl" in the "optionally substituted cyclic hydrocarbyl" or "heterocyclic group" in the "optionally substituted heterocyclic group" for $R^2$ may be combined each other to form a fused ring with the cyclic hydrocarbyl or heterocyclic group. Examples of the fused ring include, for example, an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Furthermore, the substituent of the "cyclic hydrocarbyl" in the "optionally substituted cyclic hydrocarbyl" or "heterocyclic group" in the "optionally substituted heterocyclic group" for $R^2$ may be combined together with the substituent: $R^4$ of —$NR^4$—, —$NR^4$-alk-, —$CONR^4$— or —$NR^4CO$— in Z of formula (I) or (I') to form a nitrogen-containing fused ring with the cyclic hydrocarbyl or heterocyclic group of $R^2$. Examples of the fused ring include, for example, 8- to 12-membered bicyclic heterocyclic group formed by a fusion of a benzene ring with a saturated monocyclic heterocyclic group containing one nitrogen atom such as 1,2,3,4-tetrahydroquinolyl, 2,3,4,5-tetrahydro-1H-1-benzazepinyl, and the like.

The above-mentioned "fused ring" and "nitrogen-containing fused ring" may further have one to three substituents selected from an acyl (e.g., acetyl, propionyl, etc.), an amide (e.g., dimethylaminocarbonyl, methylaminocarbonyl, etc.), an amine (e.g., dimethylamino, methylamino, amino, etc.), a halogen (e.g., fluorine, chlorine, bromine, etc.), a lower alkyl (e.g., methyl, ethyl, trifluoromethyl, etc.) and a lower alkoxy (e.g., methoxy, ethoxy, trifluoromethoxy, etc.), each of which may be substituted.

Among these, $R^2$ is preferably an optionally substituted $C_{6-10}$ aryl (more preferably phenyl) or an optionally substituted 5- to 8-membered (more preferably 5- to 6-membered) heterocyclic group (more preferably pyridyl) $R^2$ is more preferably phenyl which is 2,4-disubstituted, 2,4,6-trisubstituted or 2,4,5-trisubstituted with two or three substituents, or pyridyl which is disubstituted or trisubstituted with two or three substituents. The substituents for the phenyl and pyridyl may be the same or different and examples thereof include an acyl (e.g., acetyl, propionyl, etc.), an amide (e.g., dimethylaminocarbonyl, methylaminocarbonyl, etc.), an amine (e.g., dimethylamino, methylamino, amino, etc.), a halogen (e.g., fluorine, chlorine, bromine, etc.), a lower alkyl (e.g., methyl, ethyl, trifluoromethyl, etc.) and a lower alkoxy (e.g., methoxy, ethoxy, trifluoromethoxy, etc.), each of which may be substituted.

In the formula (I) and (I'), $Y^1$ is $CR^{3a}$ or a nitrogen, $Y^2$ is $CR^{3b}$ or a nitrogen, and $Y^3$ is $CR^{3c}$ or a nitrogen (wherein $R^{3a}$, $R^{3b}$ and $R^{3c}$ are independently a hydrogen, a halogen, a nitro, a cyano, an optionally substituted hydrocarbyl, an optionally substituted hydrocarbyloxy, an optionally substituted hydrocarbylthio, an optionally substituted amino or an acyl), provided that one or less of $Y^1$, $Y^2$ and $Y^3$ is nitrogen.

The 6-membered ring with $Y^1$, $Y^2$ and $Y^3$ of the formula (I) and (I') is a ring containing one or less nitrogen atom such as benzene ring and pyridine ring.

Examples of halogen include fluorine, chlorine, bromine, iodine, and the like, preferably, chlorine and bromine.

Examples of the "optionally substituted hydrocarbyl" in $R^{3a}$, $R^{3b}$ and $R^{3c}$ include the same groups as those exemplified with respect to the optionally substituted hydrocarbyl of $R^3$. Among them, an optionally substituted $C_{1-3}$ alkyl is preferred, and an unsubstituted $C_{1-3}$ alkyl, $C_{1-3}$ alkyl substituted with hydroxy and $C_{1-3}$ alkyl substituted with an amine (e.g., dimethylamino, methylamino, pyrrolidine, etc.) are more preferred. Examples of the hydrocarbyl for said "optionally substituted hydrocarbyloxy" and "optionally substituted hydrocarbylthio" of $R^{3a}$, $R^{3b}$ and $R^{3c}$ include the same groups as those exemplified with respect to the optionally substituted hydrocarbyl of $R^3$. In particular, hydrocarbyl having 1 to 4 carbon atoms is preferred.

Among them, an optionally substituted $C_{1-3}$ alkoxy is preferred, and an substituted $C_{1-3}$ alkoxy and halogenated substituted $C_{1-3}$ alkoxy are more preferred, and in particular, methoxy, difluoromethoxy and trifluoromethoxy are preferred. Examples of the "optionally substituted amino" for $R^{3a}$, $R^{3b}$ and $R^{3c}$ include amino group, an N-mono-substituted amino group, and an N,N-di-substituted amino group. Examples of said substituted amino groups include that having one or two substituents of an optionally substituted hydrocarbyl group (e.g., a $C_{1-8}$ alkyl group, a $C_{3-7}$ cycloalkyl group, a $C_{2-8}$ alkenyl group, a $C_{2-8}$ alkynyl group, a $C_{3-7}$ cycloalkenyl group, a $C_{6-10}$ aryl group that may have a $C_{1-4}$ alkyl group, etc.), an optionally substituted heterocyclic group (e.g., the same group as an optionally substituted heterocyclic group of $R^2$), or the formula: —$COR^{3d}$ (wherein $R^{3d}$ represents hydrogen atom or an optionally substituted hydrocarbyl group or an optionally substituted heterocyclic group. As for "the hydrocarbyl group" or "the heterocyclic group" in "an optionally substituted hydrocarbyl group" or "an optionally substituted heterocyclic group" of $R^{3d}$ may have the same substituent as that of "the hydrocarbyl group" or "the heterocyclic group" in "an optionally substituted hydrocarbyl" of $R^3$ or "an optionally substituted heterocyclic group" of $R^2$), preferably a $C_{1-10}$ acyl group (e.g., a $C_{2-7}$ alkanoyl, benzoyl, nicotinoyl, etc.).

Specific examples thereof include methylamino, dimethylamino, ethylamino, diethylamino, dipropylamino, dibutylamino, diallylamino, cyclohexylamino, phenylamino, N-methyl-N-phenylamino, acetylamino, propionylamino, benzoylamino, nicotinoylamino, and the like.

In addition, the two groups in said substituted amino groups may be combined to form a nitrogen-containing 5- to 7-membered ring (e.g., piperidino, piperazino, morpholino, thiomorpholino, etc.).

Examples of the acyl for $R^{3a}$, $R^{3b}$ and $R^{3c}$ include the same groups as those exemplified with respect to the acyl for $R^3$. In particular, an acyl having 2 to 4 carbon atoms is preferred.

In the formula (I) and (I'), $Y^1$, $Y^2$ and $Y^3$ are preferably $CR^{3a}$, $CR^{3b}$ and $CR^{3c}$ respectively, or one of $Y^1$, $Y^2$ and $Y^3$ is nitrogen. $R^{3a}$, $R^{3b}$ and $R^{3c}$ are preferably hydrogen, halogen, cyano, acyl, $C_{1-4}$ alkyl optionally substituted by hydroxy (for example, methyl, ethyl, hydroxymethyl), amino, and $C_{1-4}$ alkoxy (for example, methoxy, ethoxy). As $R^{3a}$, chlorine, bromine, methoxy and methyl are more preferred.

In the formula (I) and (I'), Z is a bond, —CO—, an oxygen (—O—), a sulfur (—S—), —SO—, —SO$_2$—, —NR$^4$—, —NR$^4$-alk-, —CONR$^4$— or —NR$^4$CO—.

Said alk is an optionally substituted $C_{1-4}$ alkylene such as methylene, ethylene, propylene, butylene and the like.

$R^4$ is a hydrogen, an optionally substituted hydrocarbyl or an acyl. The "optionally substituted hydrocarbyl" and "acyl" for $R^4$ include the same groups as those exemplified with respect to the optionally substituted hydrocarbyl group and acyl for $R^3$.

In addition, $R^4$ may be combined together with the substituent of the cyclic hydrocarbyl or heterocyclic group in the optionally substituted hydrocarbyl or optionally substituted heterocyclic group of $R^2$ to form a ring. Examples of said ring include the same rings as those exemplified with respect to the rings formed by the two substituents of $R^2$ mentioned above.

Provided that
(i) the compound wherein X is —NH—, and $R^2$ is an optionally substituted thiophene ring,
(ii) the compound wherein $R^1$ is cyano, $R^{3c}$ is methyl substituted with three substituents, one of which is acyl, and other two of which may form a ring,
(iii) a) 6-amino-2-[(2,6-dichlorophenyl)amino]-1-methyl-1H-benzimidazole-7-carbonitrile,
b) N-{7-cyano-2-[(2,6-dichlorophenyl)amino]-1-methyl-1H-benzimidazol-6-yl}acetamide,
c) 6-amino-2-[(2,6-dichlorophenyl)amino]-1-methyl-1H-benzimidazole-7-carboxamide, and
d) 6-{[(allylamino)carbonothioyl]amino}-2-[(2,6-dichlorophenyl)amino]-1-methyl-1H-benzimidazole-7-carboxamide,
(iv) 4-({2-[(4-chlorophenyl)amino]-1,7-dimethyl-1H-benzimidazol-5-yl}oxy)-N-methylpyridine-2-carboxamide,
(v) N-[3,5-bis(trifluoromethyl)phenyl]-7-methyl-1H-benzimidazol-2-amine,
(vi) the compound wherein $R^3$ is substituted heteroarylmethyl, $R^2$ is 4-piperidinyl bearing a substituent at the 1-position,
(vii) 6-chloro-4-methyl-N-piperidin-4-yl-1H-benzimidazol-2-amine, and
(viii) the compound wherein $R^2$ is substituted 8-oxo-5-thia-1-aza-bicyclo[4.2.0]oct-2-en-7-yl are excluded from the compounds of the formula (I).

As a preferred compound of the formula (I) and (I'), a compound wherein X is $NR^3$ (wherein $R^3$ is preferably methyl, ethyl, hydroxyethyl, etc.); $Y^1$ is $CR^{3a}$ (wherein $R^{3a}$ is preferably H, Me, halogen (eg. F, Cl, Br), cyano, acyl, alkoxy, etc.), $Y^2$ is $CR^{3b}$ (wherein $R^{3b}$ is preferably H, Me, halogen (eg. F, Cl, Br), etc.) or nitrogen and $Y^3$ is $CR^{3c}$ (wherein $R^{3c}$ is preferably H, Me, halogen (eg. F, Cl, Br), etc.) or nitrogen; Z is $NR^4$ (wherein $R^4$ is preferably H, $C_{1-4}$ alkyl, etc.) or oxygen; $R^1$ is an optionally substituted acyclic branched $C_{3-7}$ hydrocarbyl (in particular, 2-propyl, 3-hexyl, 3-pentyl, 4-heptyl); and $R^2$ is an optionally substituted $C_{6-10}$ aryl (in particular, phenyl, more preferably di- or tri-substituted phenyl) or an optionally substituted pyridyl (in particular, pyridyl, more preferably di- or tri-substituted pyridyl) is exemplified. Among them, particularly preferred is the compound wherein $R^1$ is 3-pentyl, 3-hexyl or 4-heptyl, X is $NR^3$, $R^3$ is methyl, ethyl or hydroxyethyl, $Y^1$ is $CR^{3a}$, $Y^2$ is $CR^{3b}$, $Y^3$ is $CR^{3c}$, $R^{3a}$ is chloro, bromo, methoxy or methyl, $R^{3b}$ is a hydrogen, $R^{3c}$ is a hydrogen, $R^2$ is phenyl which is 2,4,6-trisubstituted, 2,4,5-trisubstituted or 2,4-disubstituted with substituents or pyridyl which is trisubstituted or disubstituted with substituents. Examples of the substituents for the phenyl and pyridyl include an acyl such as acetyl and propionyl, an amide such as dimethylaminocarbonyl and methylaminocarbonyl, an amine such as dimethylamino, methylamino and amino, a halogen such as fluoro, chloro and bromo, a lower alkyl such as methyl, ethyl and trifluoromethyl and a lower alkoxy such as methoxy, ethoxy and trifluoromethoxy, each of which may be substituted.

Compound (I) or (I') may be in the form of a prodrug thereof. The prodrug of compound (I) or (I') refers to a compound that is converted into compound (I) or (I') by a reaction with an enzyme, gastric acid, or the like under a physiological condition in the living body, namely, (i) a compound that is converted into compound (I) or (I') by an enzymatic oxidation, reduction, hydrolysis, or the like, and (ii) a compound that is converted into compound (I) or (I') by hydrolysis with gastric acid or the like. Examples of a prodrug of compound (I) or (I') to be used include a compound or its salt wherein hydroxyl group in compound (I) or (I') is acylated, alkylated, phosphorylated, or converted into borate (e.g., a compound or its salt wherein hydroxyl group in compound (I) or (I') is converted into acetyloxy, palmitoyloxy, propanoyloxy, pivaloyloxy, succinyloxy, fumaryloxy, alanyloxy, dimethylaminomethylcarbonyloxy, etc.), a compound or its salt wherein carboxyl group in compound (I) or (I') is esterified or amidated (e.g., a compound or its salt wherein carboxyl group in compound (I) or (I') is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide, etc.), or the like. These prodrugs can be produced according to a per se known method or its modified method.

Further, a prodrug of compound (I) or (I') may be a compound or its salt that is converted into compound (I) or (I') under physiological conditions as described in "Development of Drugs", Volume 7, Molecular Design, Hirokawa Shoten, 1990; pages 163-198.

General Synthetic Method

Production of a compound of formula (I) or a salt thereof of the present invention is discussed below. The following examples are given to illustrate the invention and are not intended to be inclusive in any manner. Alternative methods may be employed by one skilled in the art.

A process for preparing compound (I) or a salt thereof of the present invention is shown in the following methods.

(Scheme 1)

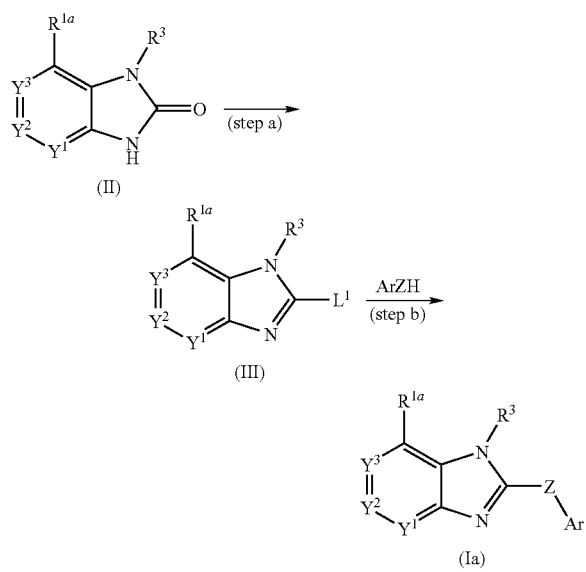

wherein $R^{1a}$ is an optionally substituted hydrocarbyl, an optionally substituted C-linked heterocyclic, an optionally substituted N-linked heteroaryl and acyl, Ar is an optionally substituted aryl, $L^1$ is a leaving group (for example, halogen atom such as chlorine, bromine and iodine, etc, sulfonyloxy group such as p-toluenesulfonyloxy group, methanesulfonyloxy group and trifluoromethanesulfonyloxy group, etc., and acyloxy group such as acetyloxy group and benzoyloxy group, etc.) and each of other symbols has a meaning defined above.

Compound (III) or a salt thereof can be prepared by halogenation, sulfonylation or acylation of compound (II) or a salt thereof with a halogenation agent, sulfonylation agent or acylation agent, respectively.

Examples of a halogenation agent include phosphorous oxychloride, phosphorous oxybromide, phosphorous trichloride, phosphorous tribromide, phosphorous pentachloride, chlorine, bromine and thionyl chloride. The halogenation agent is employed in an amount of 1 moles to excess per 1 mole of compound (II) or as a solvent.

Examples of solvent having no adverse effect on the reaction include aromatic hydrocarbons such as benzene, toluene and xylene, ethers such as diethyl ether, dioxane and tetrahydrofuran, esters such as ethyl acetate, nitrites such as acetonitrile, halogenated hydrocarbon such as chloroform and dichloromethane, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio.

While the reaction temperature may vary depending on compound (II) or a salt thereof employed as well as other conditions, it is 0 to 200° C., preferably 20 to 150° C. The reaction time is 10 minutes to 24 hours, preferably 30 minutes to 12 hours.

The thus obtained compound (III) can be isolated and purified by the known isolating and purifying methods, for example, concentration under reduced pressure, extraction with solvent, crystallization, recrystallization, transfer dissolution and chromatography.

When $L^1$ is a sulfonyloxy or an a acyloxy group in compound (III) or a salt thereof, compound (III) or a salt thereof can be prepared by reacting compound (II) with a sulfonylation agent or an acylation agent after base treatment of compound (II).

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

Examples of a sulfonylation agent include p-toluenesulfonyl chloride, methanesulfonylchloride, trifluoromethanesulfonylchloride, etc. The sulfonylation agent is employed in an amount of 1 to 10 moles, preferably 1 to 5 moles per 1 mole of compound (II).

Examples of an acylation agent include acetylchloride, benzoyl chloride, etc. The acylation agent is employed in an amount of 1 to 10 moles, preferably 1 to 5 moles per 1 mole of compound (II).

Examples of the solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (II) or a salt thereof employed as well as other conditions, it is 0 to 200° C., preferably 0 to 150° C. The reaction time is 10 minutes to 24 hours, preferably 30 minutes to 12 hours.

The thus obtained compound (III) can be isolated and purified by the known isolating and purifying methods, for example, concentration under reduced pressure, extraction with solvent, crystallization, recrystallization, transfer dissolution and chromatography.

Compound (Ia) or a salt thereof, which is encompassed within compound (I) of the invention, can be prepared by reacting compound (III) with ArZH.

In this step, 1 to 20 moles, preferably 1 to 10 moles of a compound represented by ArZH or a salt thereof are employed per 1 mole of compound (III) or a salt thereof.

This reaction may be performed under basic conditions. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (III) or a salt thereof employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

The thus obtained compound (Ia) can be isolated and purified by the known isolating and purifying methods, for example, concentration, concentration under reduced pressure, extraction with solvent, crystallization, recrystallization, transfer dissolution and chromatography.

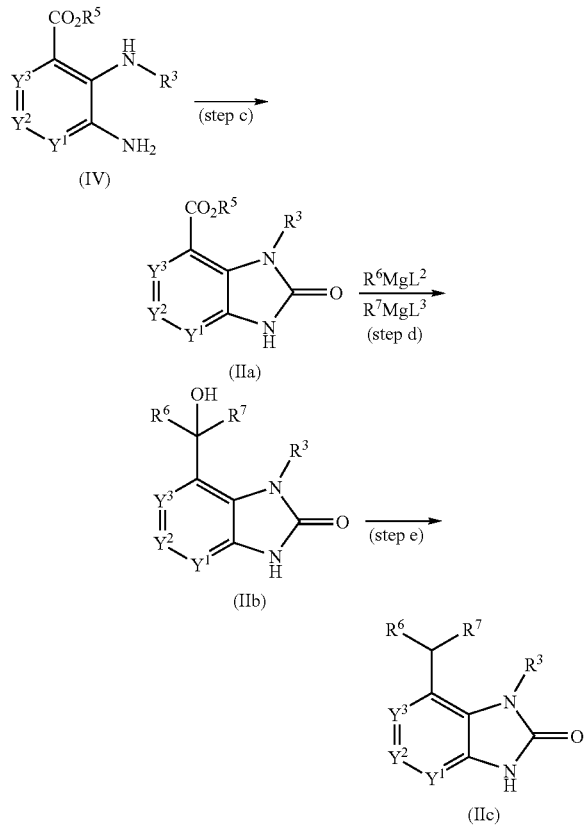

wherein $R^5$ is hydrogen and an optionally substituted hydrocarbyl, $R^3$ and $R^5$ may be combined each other to form a ring, $R^6$ and $R^7$ are optionally substituted hydrocarbyl, $L^2$ and $L^3$ are halogen atoms such as chlorine, bromine and iodine and each of other symbols has a meaning defined above.

Compound (IIa) or a salt thereof can be prepared by treatment of compound (IV) with 1,1'-carbonyl diimidazole, phosgene, triphosgene, alkyl haloformate such as ethyl chloroformate, phenyl haloformate such as phenyl chloroformate or urea, etc. Compound (IV) or a salt thereof is mainly commercially available or can be prepared from the nitro derivatives corresponded to compound (IV).

In this step, 1 to 5 moles, preferably 1 to 3 moles of an agent for cyclization or a salt thereof are employed per 1 mole of compound (IV) or a salt thereof.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (IV) or a salt thereof employed as well as other reaction conditions, it is 0 to 150° C., preferably 20 to 100° C. The reaction time is 5 minutes to 48 hours, preferably 5 minutes to 24 hours.

The thus obtained compound (IIa) can be isolated and purified by the known isolating and purifying methods, for example, concentration, concentration under reduced pressure, extraction with solvent, crystallization, recrystallization, transfer dissolution and chromatography.

Compound (IIb) or a salt thereof can be prepared by Grinard reaction of compound (IIa) or a salt thereof with $R^6MgL^2$ and $R^7MgL^3$. When $R^6$ is equal to $R^7$ in compound (IIb), $R^6MgL^2$ may be used in this step. When $R^6$ is not equal to $R^7$ in compound (IIb), the Grinard reactions may be performed stepwise by $R^6MgL^2$ and $R^7MgL^3$ in this step.

In this step, 1 to 20 moles, preferably 1 to 10 moles of a compound represented by $R^6MgL^2$ and $R^7MgL^3$ or a salt thereof are employed per 1 mole of compound (IIa) or a salt thereof.

Examples of solvent having no adverse effect on the reaction include ethers such as diethyl ether, dioxane and tetrahydrofuran, aromatic hydrocarbons such as benzene, toluene and xylene, halogenated hydrocarbons such as chloroform and dichloromethane, ketones such as acetone and 2-butanone and sulfoxides such as dimethylsulfoxide. These solvents may be used by mixing at an appropriate ratio, or may not be used.

While the reaction temperature may vary depending on compound (IIa) or a salt thereof employed as well as other reaction conditions, it is −20 to 150° C., preferably 0 to 100° C. The reaction time is 5 minutes to 24 hours, preferably 5 minutes to 12 hours.

The thus obtained compound (IIb) can be isolated and purified by the known isolating and purifying methods, for example, concentration, concentration under reduced pressure, extraction with solvent, crystallization, recrystallization, transfer dissolution and chromatography.

Compound (IIc) or a salt thereof can be prepared by dehydration of compound (IIb) or a salt thereof with an acid, and the olefine is then reduced by an appropriate reducing agent or catalytic hydrogenation.

An acid may for example be an inorganic acid such as hydrochloric acid, sulfuric acid, nitric acid and thionyl chloride, etc., and an ordinary organic acid such as formic acid, acetic acid, trifluoroacetic acid and methanesulfonic acid, etc. as well as a Lewis acid.

In dehydration step, 1 mole to excess of an acid is employed per 1 mole of compound (IIb) or a salt thereof or an acid may be employed as a solvent.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (IIb) or a salt thereof employed as well as other reaction conditions, it is 0 to 200° C., preferably 20 to 150° C. The reaction time is 5 minutes to 48 hours, preferably 5 minutes to 24 hours.

The thus obtained olefine can be isolated and purified by the known isolating and purifying methods, for example, concentration, concentration under reduced pressure, extraction with solvent, crystallization, recrystallization, transfer dissolution and chromatography.

In reduction step, a reducing agent is preferably sodium borohydride, lithium borohydride, sodium cyanoborohydride and sodium triacetoxyborohydride. Catalytic hydrogenation may be performed in this step. Examples of a catalyst include a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, and Raney nickel.

In this step, 1 to 20 moles, preferably 1 to 10 moles of a reducing agent are employed per 1 mole of the olefine or a salt thereof.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio.

While the reaction temperature may vary depending on the olefine or a salt thereof employed as well as other reaction conditions, it is 0 to 150° C., preferably 0 to 100° C. The reaction time is 5 minutes to 48 hours, preferably 5 minutes to 24 hours.

The thus obtained compound (IIc) can be isolated and purified by the known isolating and purifying methods, for example, concentration, concentration under reduced pressure, extraction with solvent, crystallization, recrystallization, transfer dissolution and chromatography.

(Scheme 3)

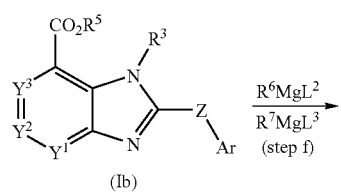

(Ib)

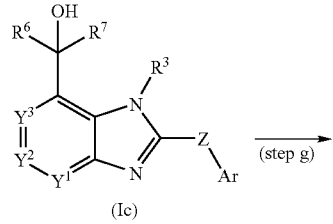

(Ic)

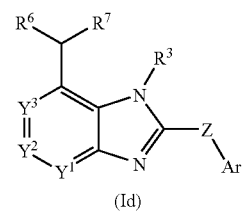

(Id)

wherein each symbol has a meaning defined above.

Preparation of compound (Ic) or a salt thereof, which is encompassed within compound (I) of the invention, from compound (Ib) or a salt thereof can be carried out similar to preparation of compound (IIb) in Scheme 2.

Preparation of compound (Id) or a salt thereof, which is encompassed within compound (I) of the invention, from compound (Ic) or a salt thereof can be carried out similar to preparation of compound (IIc) in Scheme 2.

(Scheme 4)

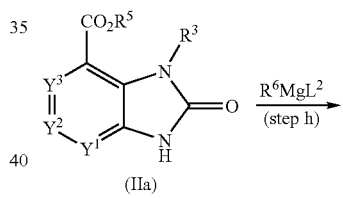

(IIa)

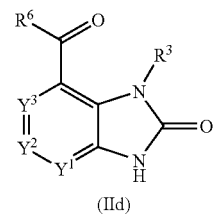

(IId)

wherein each symbol has a meaning defined above.

Preparation of compound (IId) or a salt thereof from compound (IIa) or a salt thereof can be carried out similar to preparation of compound (IIb) in Scheme 2.

(Scheme 5)

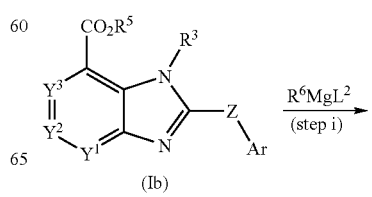

(Ib)

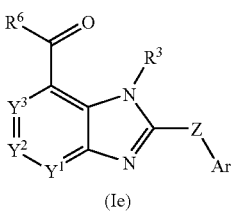

(Ie)

wherein each symbol has a meaning defined above.

Preparation of compound (Ie) or a salt thereof, which is encompassed within compound (I) of the invention, from compound (Ib) or a salt thereof can be carried out similar to preparation of compound (IIb) in Scheme 2.

(Scheme 6)

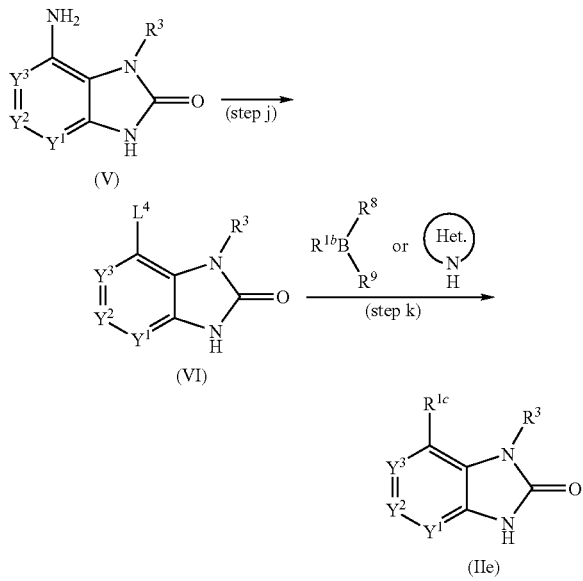

wherein $R^{1b}$ is an optionally substituted hydrocarbyl and an optionally substituted C-linked heterocyclic, $R^{1c}$ is an optionally substituted hydrocarbyl, an optionally substituted C-linked heterocyclic and an optionally substituted N-linked heteroaryl, $R^8$ and $R^9$ are independently hydrogen, optionally substituted hydrocarbyl, hydroxy and optionally substituted alkoxy and may be combined each other to form a ring,

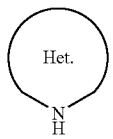

is a heteroaryl, $L^4$ is a halogen atom such as chlorine, bromine and iodine each of other symbols has a meaning defined above.

Compound (VI) or a salt thereof can be prepared by halogenation of compound (V) or a salt thereof with a halogenation agent.

Examples of a halogenation agent include chlorine, bromine, iodine, thionyl chloride, copper(I) chloride, copper(II) chloride, copper(I) bromide, copper(II) bromide, sodium chloride, sodium bromide, sodium iodide, potassium iodide, etc. The halogenation agent is employed in an amount of 0.5 moles to 10 moles, preferably 0.5 moles to 5 moles, per 1 mole of compound (V).

In this step, the diazonium type compound may be produced before introduction of a halogen atom. Examples of an agent to produce the diazonium type compound include sodium nitrite, potassium nitrite and tert-butyl nitrite, etc. The agent is employed in an amount of 1 mole to 10 moles, preferably 1 mole to 5 moles, per 1 mole of compound (V).

This reaction can be carried out under an acidic condition. Examples of an acid include an inorganic acid such as hydrochloric acid, hydrobromic acid, hydroiodic acid, sulfuric acid, a nitric acid and copper sulfate, etc., as well as Lewis acid. An acid is employed in an amount of 2 moles to excess per 1 mole of compound (V).

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio.

While the reaction temperature may vary depending on compound (V) or a salt thereof employed as well as other conditions, it is −20 to 150° C., preferably 0 to 100° C. The reaction time is 10 minutes to 24 hours, preferably 30 minutes to 12 hours.

The thus obtained compound (VI) can be isolated and purified by the known isolating and purifying methods, for example, concentration under reduced pressure, extraction with solvent, crystallization, recrystallization, transfer dissolution and chromatography.

When $R^{1c}$ is an optionally substituted hydrocarbyl, an optionally substituted C-linked heterocyclic in compound (IIe) or a salt thereof, compound (IIe) or a salt thereof can be prepared by reacting compound (VI) with $R^{1b}BR^8R^9$ or a salt thereof in the presence of a palladium catalyst, preferably tetrakis(triphenylphosphine)palladium(0) and tris(dibenzylideneacetate)dipalladium(0), a catalytic amount of a phosphine ligand, preferably 2-(dicyclohexylphosphino)biphenyl, 2-(dicyclohexylphosphino)-2',6'-dimethoxy-1,1'-biphenyl (S-Phos) and 2-(dicyclohexylphosphino)-2',4',6'-triisopropyl-1,1'-biphenyl (X-Phos) and a base according to the procedure of Suzuki coupling (Organic Synthesis via Boranes, vol. 3: Suzuki coupling, A. Suzuki and H. C. Brown, Aldrich, 2002) and the modified methods, or a trialkyl aryl tin such as aryl trimethyltin or aryl tributyltin, etc. or a salt thereof and optional additives according to the procedure of Stille coupling (Angew. Chem. Int. Ed. Engl., 25, 504 (1986)) and the modified methods.

When $R^{1c}$ is

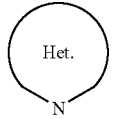

in compound (IIe), compound (IIe) or a salt thereof can be also prepared by reacting compound (VI) or a salt thereof with

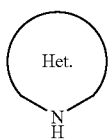

or a salt thereof in the presence of a palladium catalyst, preferably palladium (II) acetate or a copper agent, preferably copper(II) acetate. A catalytic amount of a phosphine ligand, preferably 2-(dicyclohexylphosphino)biphenyl, may be employed. This reaction can be carried out according to the procedure of Buchwald et al. (J. Am. Chem. Soc. 1998, 120, 9722) and Lam et. al. (Tetrahedron Lett., 1998, 39, 2941) and the modified methods.

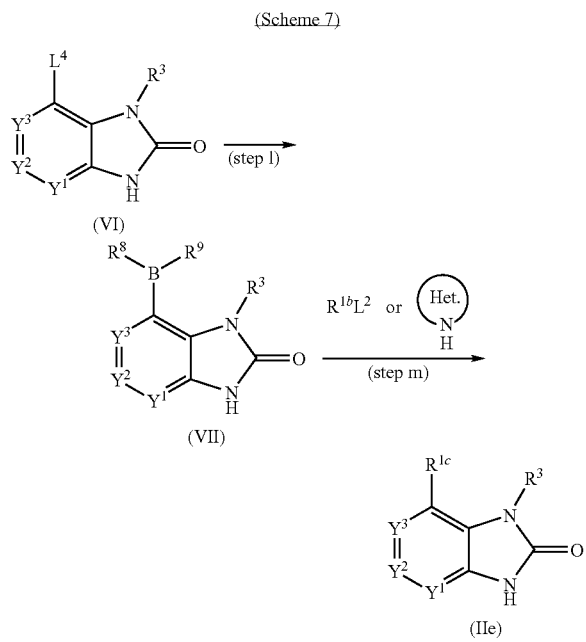

wherein each symbol has a meaning defined above.

Compound (VII) or a salt thereof can be prepared by reaction of compound (VI) or a salt thereof via lithiation or coupling reaction with a boron agent.

When the reaction is performed via lithiation, examples of a boron agent include trialkyl borate, preferably triisopropyl borate.

In this step, 1 to 10 moles, preferably 1 to 5 moles of a boron agent are employed per 1 mole of compound (VI) or a salt thereof.

A lithiation agent may for example be alkyl lithium, preferably n-butyl lithium, sec-butyl lithium and tert-butyl lithium and is employed in an amount of 1 to 5 moles, preferably 1 to 0.3 moles per 1 mole of compound (VI) or a salt thereof.

Examples of solvent having no adverse effect on the reaction include aromatic hydrocarbons such as benzene, toluene and xylene, ethers such as diethyl ether, dioxane and tetrahydrofuran, and halogenated hydrocarbon such as chloroform and dichloromethane. These solvents may be used by mixing at an appropriate ratio.

While the reaction temperature may vary depending on compound (VI) or a salt thereof employed as well as other conditions, it is −100 to 100° C., preferably −80 to 50° C. The reaction time is 10 minutes to 24 hours, preferably 30 minutes to 12 hours.

When the coupling reaction using a metal catalyst is carried out, examples of a boron agent include 4,4,5,5-tetramethyl-1,3,2-dioxaborolane and bis(pinacolato)diborane. In this step, 1 to 10 moles, preferably 1 to 5 moles of a boron agent are employed per 1 mole of compound (VI) or a salt thereof.

A palladium catalyst, preferably palladium(II) diacetate, a catalytic amount of a phosphine ligand, preferably 2-(dicyclohexylphosphino)biphenyl and a base can be employed according to the procedure described in J. Org. Chem., 62, 6458 (1997) and the modified methods.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (VI) or a salt thereof employed as well as other conditions, it is 0 to 200° C., preferably 20 to 150° C. The reaction time is 10 minutes to 48 hours, preferably 30 minutes to 24 hours.

The thus obtained compound (VII) can be isolated and purified by the known isolating and purifying methods, for example, concentration under reduced pressure, extraction with solvent, crystallization, recrystallization, transfer dissolution and chromatography.

Preparation of compound (IIe) or a salt thereof from compound (VII) or a salt thereof can be carried out similar to preparation of compound (IIe) in Scheme 6.

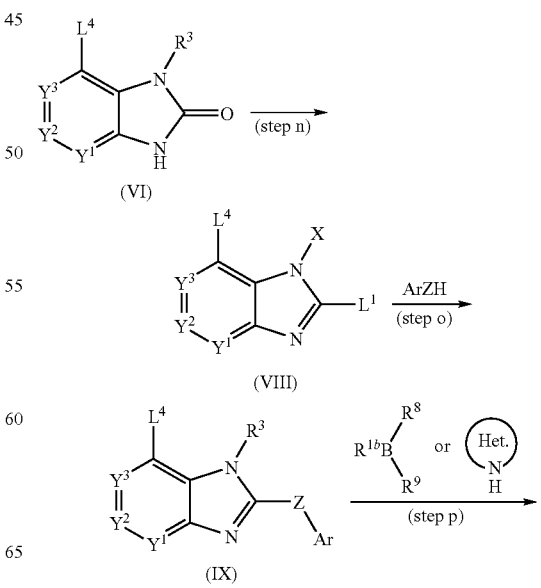

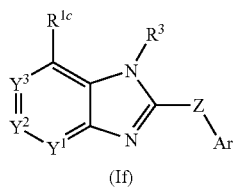

wherein each symbol has a meaning defined above.

Preparation of compound (VIII) or a salt thereof from compound (VI) or a salt thereof can be carried out similar to preparation of compound (III) or a salt thereof in Scheme 1.

Preparation of compound (IX) or a salt thereof from compound (VIII) or a salt thereof can be carried out similar to preparation of compound (Ia) or a salt thereof in Scheme 1.

Preparation of compound (If) or a salt thereof, which is encompassed within compound (I) of the invention, from compound (IX) or a salt thereof can be carried out similar to preparation of compound (IIe) or a salt thereof in Scheme 6.

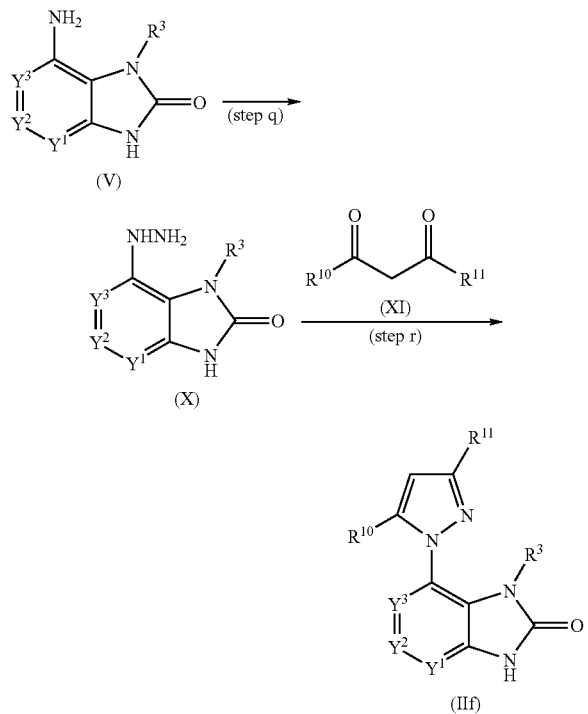

wherein $R^{10}$ and $R^{11}$ are hydrogen and optionally substituted hydrocarbyl and each of other symbols has a meaning defined above.

Compound (X) or a salt thereof can be prepared by reaction of compound (V) or a salt thereof with sodium nitrite, and the obtained diazonium salt is reduced by an appropriate reducing agent.

In this step, 1 to 5 moles, preferably 1 to 3 moles of sodium nitrite are employed per 1 mole of compound (V) or a salt thereof.

Examples of a reducing agent include alkaline metal borohydride, preferably sodium borohydride, lithium borohydride, sodium cyanoborohydride and sodium triacetoxyborohydride, metal, preferably Fe, Zn, Sn and $SnCl_2$ and metal catalyst, a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, and Raney nickel. The reducing agent is employed in an amount of catalytic amount to excess per 1 mole of compound (V).

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio, or may not be used.

While the reaction temperature may vary depending on compound (V) or a salt thereof employed as well as other conditions, it is −20 to 150° C., preferably 0 to 100° C. The reaction time is 10 minutes to 24 hours, preferably 30 minutes to 12 hours.

The thus obtained compound (X) can be isolated and purified by the known isolating and purifying methods, for example, concentration under reduced pressure, extraction with solvent, crystallization, recrystallization, transfer dissolution and chromatography.

Compound (IIf) or a salt thereof can be prepared by reaction of compound (X) or a salt thereof with compound (XI) or a salt thereof.

In this step, 1 to 5 moles, preferably 1 to 3 moles of compound (XI) or a salt thereof are employed per 1 mole of compound (X) or a salt thereof.

An acid may be used and for example be an inorganic acid such as hydrochloric acid, sulfuric acid and nitric acid, etc., and an ordinary organic acid such as formic acid, acetic acid, p-toluenesulfonic acid, trifluoroacetic acid and methanesulfonic acid, etc. as well as a Lewis acid.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, acids such as formic acid and acetic acid and sulfoxides such as dimethylsulfoxide. These solvents may be used by mixing at an appropriate ratio.

While the reaction temperature may vary depending on compound (V) or a salt thereof employed as well as other conditions, it is 0 to 200° C., preferably 20 to 150° C. The reaction time is 10 minutes to 24 hours, preferably 30 minutes to 12 hours.

The thus obtained compound (IIf) can be isolated and purified by the known isolating and purifying methods, for example, concentration under reduced pressure, extraction with solvent, crystallization, recrystallization, transfer dissolution and chromatography.

(Scheme 10)

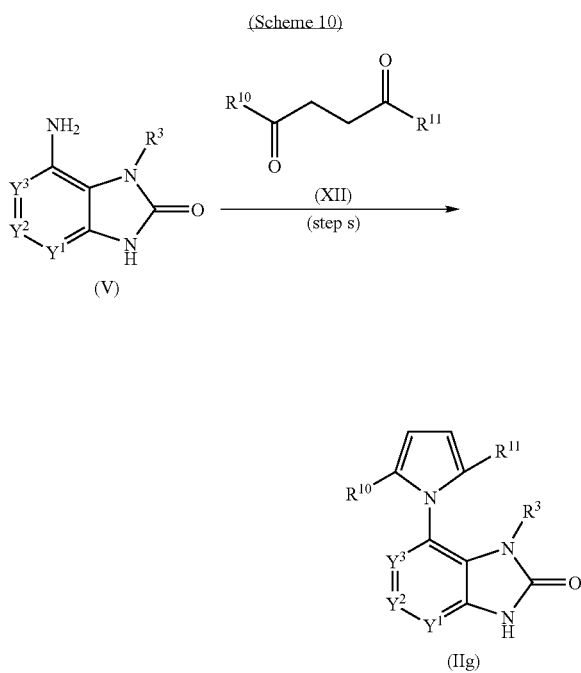

wherein each symbol has a meaning defined above.

Preparation of compound (IIg) or a salt thereof from compound (V) or a salt thereof can be carried out similar to preparation of compound (IIf) or a salt thereof in Scheme 9.

(Scheme 11)

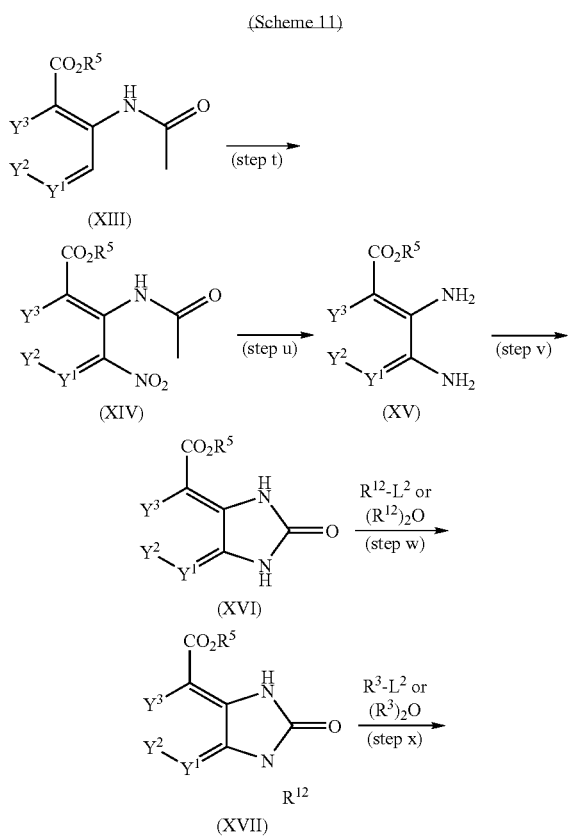

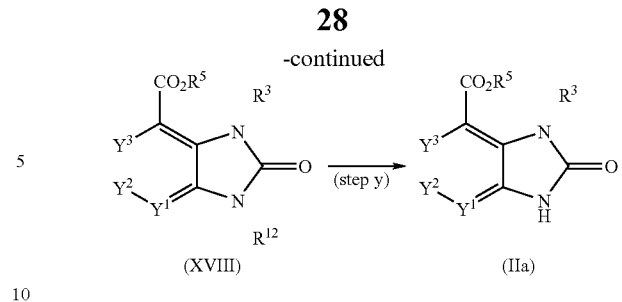

wherein $R^{12}$ is an optionally substituted $C_{1-6}$ alkylcarbonyl (for example. formyl, methylcarbonyl and ethylcarbonyl, etc.), phenylcarbonyl, a $C_{1-6}$ alkyloxycarbonyl (for example, methoxycarbonyl, ethoxycarbonyl and tert-butoxycarbonyl, etc.), phenyloxycarbonyl (for example, benzoxycarbonyl), $C_{7-10}$ aralkylcarbonyl (for example, benzyloxycarbonyl), $C_{7-10}$ aralkyl (for example, benzyl and 4-methoxybenzyl, etc.), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.) and a nitro group, and each of other symbols has a meaning defined above.

Compound (IIa) or a salt thereof can be also prepared by the procedure as shown in scheme 11.

Compound (XIV) or a salt thereof can be prepared by nitration of compound (XIII) or a salt thereof with a nitration agent. Compound (XIII) or a salt thereof is mainly commercially available or can be prepared from the aniline derivatives corresponded to compound (XIII) by a usual acetylation method.

Examples of a nitration agent include nitric acids (for example, fuming nitric acid, a solution of nitric acid and sulfuric acid etc.), nitrates (for example, sodium nitrate, potassium nitrate, silver nitrate, ammonium nitrate, benzoyl nitrate, benzyltriphenylphosphonium nitrate, bismuth subnitrate, etc). The nitration agent is employed in an amount of 0.5 moles to 50 moles, or may be employed as a solvent, preferably 0.5 moles to 30 moles, per 1 mole of compound (XIII).

This reaction is also carried out in the presence of additives. Examples of additives include anhydrides (for example, acetic anhydride, trifluoroacetic anhydride, methanesulfonic anhydride, etc), acid chlorides (for example, thionyl chloride, etc), acids
(for example, acetic acid, methanesulfonic acid, etc), metals (for example, iron, etc).

The additives are employed in an amount of 0.5 moles to 50 moles, preferably 0.5 moles to 30 moles, per 1 mole of compound (XIII).

Examples of solvent having no adverse effect on the reaction include water, acetic acid, halogenated hydrocarbons such as chloroform and dichloromethane, 1,2-dichloroethane, etc. These solvents may be used by mixing at an appropriate ratio, or may not be used. While the reaction temperature may vary depending on compound (XIII) or a salt thereof employed as well as other reaction conditions, it is −20 to 150° C., preferably 0 to 100° C. The reaction time is 5 minutes to 48 hours, preferably 5 minutes to 24 hours. The thus obtained compound (XIV) can be isolated and purified by the known isolating and purifying methods, for example, concentration, concentration under reduced pressure, extraction with solvent, crystallization, recrystallization, transfer dissolution and chromatography.

Compound (XV) or a salt thereof can be prepared by deacetylation of compound (XIV) or a salt thereof with an acid or base, and then reduction of the nitro group by an appropriate reducing agent or catalytic hydrogenation.

An acid may for example be an inorganic acid such as hydrochloric acid, sulfuric acid, nitric acid and thionyl chloride, etc., and an ordinary organic acid such as formic acid, acetic acid, trifluoroacetic acid and methanesulfonic acid, etc. as well as a Lewis acid.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc.

In deacetylation step, 1 mole to excess of an acid or base is employed per 1 mole of compound (XIV) or a salt thereof, or an acid may be employed as a solvent.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (XIV) or a salt thereof employed as well as other reaction conditions, it is 0 to 200° C., preferably 20 to 150° C. The reaction time is 5 minutes to 48 hours, preferably 5 minutes to 24 hours.

The thus obtained nitro compounds can be isolated and purified by the known isolating and purifying methods, for example, concentration, concentration under reduced pressure, extraction with solvent, crystallization, recrystallization, transfer dissolution and chromatography.

In reduction step, a reducing agent is preferably sodium borohydride, lithium borohydride, sodium cyanoborohydride and sodium triacetoxyborohydride. Catalytic hydrogenation may be performed in this step. Examples of a catalyst include a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, and Raney nickel.

In this step, 1 to 20 moles, preferably 1 to 10 moles of a reducing agent are employed per 1 mole of the nitro compounds or a salt thereof.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio.

While the reaction temperature may vary depending on compound (XIV) or a salt thereof employed as well as other reaction conditions, it is 0 to 150° C., preferably 0 to 100° C. The reaction time is 5 minutes to 48 hours, preferably 5 minutes to 24 hours.

The thus obtained compound (XV) can be isolated and purified by the known isolating and purifying methods, for example, concentration, concentration under reduced pressure, extraction with solvent, crystallization, recrystallization, transfer dissolution and chromatography.

Preparation of compound (XVI) or a salt thereof from compound (XV) or a salt thereof can be carried out similar to preparation of compound (IIa) in Scheme 2.

Compound (XVII) or a salt thereof can be prepared by reacting compound (XVI) with $R^{12}$-$L^2$ or anhydride$(R^{12})_2$O.

In this step, 1 to 10 moles, preferably 1 to 5 moles of a compound represented by $R^{12}$-$L^2$ or anhydride $(R^2)_2$O or a salt thereof are employed per 1 mole of compound (XVI) or a salt thereof.

This reaction may be performed under basic conditions. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, 4-dimethylaminopyridine, DBU, etc.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (XVI) or a salt thereof employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

The thus obtained compound (XVII) can be isolated and purified by the known isolating and purifying methods, for example, concentration, concentration under reduced pressure, extraction with solvent, crystallization, recrystallization, transfer dissolution and chromatography.

Preparation of compound (XVIII) or a salt thereof from compound (XVII) or a salt thereof can be carried out similar to preparation of compound (XVII).

Compound (IIa) or a salt thereof can be prepared by deprotection of compound (XVIII) or a salt thereof with an acid or a base, or catalytic hydrogenation.

An acid may for example be an inorganic acid such as hydrochloric acid, sulfuric acid, nitric acid and thionyl chloride, etc., and an ordinary organic acid such as formic acid, acetic acid, trifluoroacetic acid and methanesulfonic acid, etc. as well as a Lewis acid.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc.

Catalytic hydrogenation may be performed in this step. Examples of a catalyst include a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, and Raney nickel.

In this step, 1 mole to excess of an acid or a base is employed per 1 mole of compound (XVIII) or a salt thereof, or an acid may be employed as a solvent.

Examples of solvent having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (XVIII) or a salt thereof employed as well as other reaction conditions, it is 0 to 200° C., preferably 20 to 150° C. The reaction time is 5 minutes to 48 hours, preferably 5 minutes to 24 hours.

The thus obtained compounds can be isolated and purified by the known isolating and purifying methods, for example, concentration, concentration under reduced pressure, extraction with solvent, crystallization, recrystallization, transfer dissolution and chromatography.

A starting compound for compound (I) according to the invention may be in a form of a salt, including a salt with an inorganic acid (for example, hydrochloric acid, phosphoric acid, hydrobromic acid and sulfuric acid, etc.) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid and benzenesulfonic acid, etc.). When any of these compounds carries an acidic group such as —COOH, etc., a salt with an inorganic base (for example, an alkaline metal or an alkaline earth metal such as sodium, potassium, calcium and magnesium, ammonia, etc.) or with an organic base (for example, tri-$C_{1-3}$ alkylamine such as triethylamine, etc.) may be formed.

In each of the reactions described above, when a starting compound carries as a substituent an amino group, an amide group, a hydrozino group, a urea group, a carboxyl group or a hydroxyl group, then such group may be derivatized with a protective group employed ordinarily in peptide chemistry, which is cleaved after a reaction if desired to yield an intended compound.

A protective group for an amino group, an amide group and a urea group may for example be an optionally substituted $C_{1-6}$ alkylcarbonyl (for example. formyl, methylcarbonyl and ethylcarbonyl, etc.), phenylcarbonyl, a $C_{1-6}$ alkyloxycarbonyl (for example, methoxycarbonyl, ethoxycarbonyl and tert-butoxycarbonyl, etc.), phenyloxycarbonyl (for example, benzoxycarbonyl), $C_{7-10}$ aralkylcarbonyl (for example, benzyloxycarbonyl), $C_{7-10}$ aralkyl (for example, benzyl and 4-methoxybenzyl, etc.), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.) and a nitro group, which may occur 1 to about 3 times.

A protective group for a carboxyl group may for example be an optionally substituted $C_{1-6}$ alkyl (for example, methyl, ethyl, n-propyl, i-propyl, n-butyl and t-butyl, etc.), phenyl, trityl and silyl, etc. A substituent on each of the groups listed above may be a halogen atom (for example, fluorine, chlorine, bromine and iodine, etc.), a $C_{1-6}$ alkylcarbonyl (for example, formyl, methylcarbonyl, ethylcarbonyl and butylcarbonyl, etc.) and a nitro group, which may occur 1 to about 3 times.

A protective group for a hydroxyl group may for example be an optionally substituted $C_{1-6}$ alkyl (for example, methyl, ethyl, n-propyl, i-propyl, n-butyl and tert-butyl, etc.), phenyl, a $C_{7-10}$ aralkyl (for example, benzyl, etc.), a $C_{1-6}$ alkylcarbonyl (for example, formyl, methylcarbonyl and ethylcarbonyl, etc.), phenyloxycarbonyl (for example, benzoxycarbonyl, etc.), $C_{7-10}$ aralkylcarbonyl (for example, benzyloxycarbonyl, etc.), pyranyl, furanyl, silyl, etc. A substituent on each of the groups listed above may be a halogen atom (for example, fluorine, chlorine, bromine and iodine, etc.), a $C_{1-6}$ alkyl, phenyl, a $C_{7-10}$ aralkyl, nitro, etc., which may occur 1 to about 4 times.

A method for cleaving a protective group is a method known per se or an analogous method, such as a treatment for example with an acid, a base, a reduction, UV light, hydrazine, phenylhydrazine, sodium N-methyldithiocarbamate, tetrabutylammonium fluoride, palladium acetate, etc.

The pharmaceutical composition containing compound (I) or (I') of the present invention is expected to be useful in the treatment and prevention of diseases, in which CRF is involved, such as depression, major depression, bipolar depression, dysthymia, seasonal affective disorder, recurrent depression, postpartum depression, suppression symptom, mania, anxiety, generalized anxiety disorder, anxiety syndrome, panic disorder, phobia, social phobia, obsessive-compulsive disorder, posttraumatic stress disorder, stress-induced insomnia, post psychic trauma stress disorder, Tourette's syndrome, autism, passion disorder, adjustment disorder, dysthymic disorder, sleep disorder, insomnia, bipolar disorder, circulatory disease, neurosis, schizophrenia, digestive ulcer, irritable bowl syndrome, inflammatory bowel disease, ulcerative colitis, Crohn's disease, stress-induced gastrointestinal disorder, nervous emesis, peptic ulcer, diarrhea, constipation, postoperative ileus, gastrointestine dysfunction and nervous vomiting associated with stress, Alzheimer's disease, Alzheimer's type senile dementia, nervous degenerated disease such as Parkinson's disease and Huntington's disease, multi-infarct dementia, senile dementia, nervous orexia inactivity, eating disorder, anorexia nervosa, hyperphagia and other ingestion disorder, obesity, diabetes, alcohol dependency, pharmacophinia, drug withdrawal, migraine, stress headache, tension headache, ischemic nervous disorder, nervous disorder, cerebral paralysis, progressive supranuclear palsy, amyotrophic lateral sclerosis, multiple sclerosis, muscular convulsion, chronic fatigue syndrome, glaucoma, Meniere syndrome, autonomic imbalance, alopecia, hypertension, cardiovascular disorder, tachycardia, congestive heart attack, hyperplea, bronchial asthma, apnea, infant sudden death syndrome, inflammatory disorder, pain, allergic disorder, impotence, menopausal disorder, fertilization disorder, infertility, cancer, immune function abnormality at HIV infection, immune functional abnormality due to stress, cerebrospinal meningitis, acromegaly, incontinence or osteoporosis.

Compound (I) or (I') of the present invention can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The following examples and experiments describe the manner and process of making and using the present invention and are illustrative rather than limiting. It is to be understood that there may be other embodiments which fall within the spirit and scope of the present invention as defined by the claims appended hereto.

In the following examples, preparative HPLC was carried out under a condition described below.
Equipment: Gilson high through put purification system
Column: YMC CombiPrep ODS-A S-5 μm, 50×20 mm
Solvent: A; 0.1% aqueous trifluoroacetic acid, B; 0.1% trifluoroacetic acid in acetonitrile
Gradient cycle: 0.00 min (A/B=95/5), 1.00 min (A/B=95/5), 5.20 min (A/B=5/95), 6.40 min (A/B=5/95), 6.50 min (A/B=95/5), 6.60 min (A/B=95/5)
Flow rate: 20 mL/min
Detection: UV 220 nm Example 1

N-(4-Bromo-2-methoxy-6-methylphenyl)-1-methyl-7-(1-propylbutyl)-1H-benzimidazol-2-amine Hydrochloride

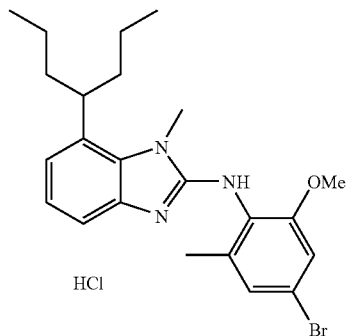

Methyl 2-chloro-3-nitrobenzoate

A slurry of 20 g (99 mmol) of 2-chloro-3-nitrobenzoic acid in 800 mL dichloromethane was cooled in an ice bath. Dimethylformamide (0.40 mL) was added to the reaction followed by drop wise addition of 13.85 g (109 mmol) of oxalyl chloride. The reaction was allowed to warm to room temperature and was stirred for 6 h. Methanol (200 mL) was added drop wise and the reaction was stirred overnight. The reaction was concentrated to a residue, dissolved in dichloromethane and passed through a plug of silica eluting with a 50% ethyl acetate/hexane mixture. The filtrate was concentrated in vacuo to give 21.5 g (100%) of the title compound.

$^1$H NMR (CDCl$_3$) δ 3.98 (s, 3H), 7.48 (t, J=7.8 Hz, 1H), 7.84 (d, J=8.2 Hz, 1H), 7.95 (d, J=7.8 Hz, 1H).

Methyl 2-Methylamino-3-nitrobenzoate

A solution of 21.5 g (99.5 mmol) of methyl 2-chloro-3-nitrobenzoate in 300 mL of tetrahydrofuran (THF) was treated with drop wise addition of 300 mL (597 mmol) of methylamine (2M solution in THF) and was stirred overnight at room temperature. The reaction was concentrated to dryness, dissolved in dichloromethane, and washed with aqueous sodium bicarbonate and water. The organics were dried over sodium sulfate, filtered, and concentrated in vacuo to give 20.8 g (100%) of the title compound.

$^1$H NMR (CDCl$_3$) δ 2.82 (d, J=5.5 Hz, 3H), 3.9 (s, 3H), 6.65 (t, J=7.8 Hz, 1H), 7.97 (d, J=8.2 Hz, 1H), 8.04 (J=7.8 Hz, 1H), 8.57 (s, 1H).

MS Calcd.: 210. Found: 211 (M+H).

Methyl 3-amino-2-methylaminobenzoate

A solution of 20.7 g (98 mmol) of methyl 2-methylamino-3-nitrobenzoate in 1200 mL of methanol was inerted with nitrogen. To this solution was added 5 g (2.3 mmol) 10% palladium on carbon (50% wet). The reaction was purged with hydrogen and stirred under balloon pressure hydrogen for 7 h. The catalyst was removed by filtration and the filtrate was concentrated in vacuo to give 17.5 g (99%) of the title compound.

MS Calcd.: 180. Found: 181 (M+H).

Methyl 1-methyl-2-oxo-1,3-dihydro-1H-benzimidazole-7-carboxylate

To a solution of 17.5 g (97 mmol) of Methy 3-amino-2-methylaminobenzoate in 550 mL of tetrahydrofuran was added 20.5 g (146 mmol) of 1,1'-carbonyldiimidazole and the reaction was stirred overnight at room temperature. The reaction was heated at 50° C. for 2 h and allowed to cool to room temperature overnight. The reaction was concentrated in vacuo and the residue was dissolved in 1 L ethyl acetate and washed with 400 mL of water. The organics were dried over sodium sulfate, filtered, and concentrated in vacuo to a residue. The residue was purified by flash chromatography eluting with a solution of 50% ethyl acetate/dichloromethane to give 7.22 g (78%) of the title compound.

$^1$H NMR (CDCl$_3$) δ 3.59 (s, 3H), 3.95 (s, 3H), 7.08 (t, J=7.8 Hz, 1H), 7.27 (d, J=7.8 Hz, 1H), 7.52 (d, J=8.2 Hz, 1H).

MS Calcd.: 206. Found: 207 (M+H).

1-Methyl-7-(1-propylbutyl)-1,3-dihydro-2H-benzimidazol-2-one

A solution of 8.5 mL (17 mmol) of propylmagnesium chloride (2M solution in diethyl ether) was diluted with 10 mL of diethyl ether and cooled in an ice bath. To this solution was slowly added 1.0 g (4.85 mmol) of methyl 1-methyl-2-oxo-1,3-dihydro-1H-benzimidazole-7-carboxylate and the reaction was stirred overnight at 35° C. The reaction was quenched with 50 mL of methanol, 100 mL of water, and 10 mL of 1N aqueous hydrochloric acid. The aqueous mixture was extracted with 50 mL of diethyl ether and twice with 50 mL of dichloromethane. The organics were combined, dried over sodium sulfate, filtered, and concentrated in vacuo to a residue. This residue was dissolved in 50 mL of ethanol and 10 mL of 6N aqueous hydrochloric acid was added. The mixture was heated at 75° C. for 2 h and then concentrated in vacuo. The resulting residue was dissolved in dichloromethane and washed with aqueous sodium bicarbonate. The organics were dried over sodium sulfate, filtered, and concentrated in vacuo to give 1.05 g of crude 1-methyl-7-(1-propylbut-1-enyl)-1,3-dihydro-2H-benzimidazol-2-one, which was used without further purification in the next step.

MS Calcd.: 244. Found: 245 (M+H). The crude material was dissolved in 50 mL of methanol and inerted with nitrogen. This solution was treated with 300 mg (2.16 mmol) of 10% palladium on carbon (50% wet), purged with hydrogen, and stirred under balloon pressure hydrogen for 36 h. The catalyst was removed by filtration and the filtrate concentrated in vacuo. The crude residue thus obtained was purified by flash chromatography eluting with a mixture of 5% methanol/dichloromethane. The resulting impure mixture was triturated with diethyl ether and filtered. The filtrate contained the title compound along with a small amount of an unidentified impurity, was concentrated in vacuo. The residue thus obtained (710 mg) was used in the next reaction without further purification.

MS Calcd.: 246. Found: 247 (M+H).

2-Chloro-1-methyl-7-(1-propylbutyl)-1H-benzimidazole

The crude 1-methyl-7-(1-propylbutyl)-1,3-dihydrobenzimidazol-2-one (710 mg, 2.88 mmol) was dissolved in 10 mL of phosphorous oxychloride and heated at 100° C. overnight. The reaction was allowed to cool to room temperature and concentrated in vacuo. The residue thus obtained was dissolved in ethyl acetate, washed with aqueous sodium bicarbonate, dried over sodium sulfate, filtered and concentrated in vacuo to give 655 mg (86%) of the title compound, which was used in the next step without further purification.

MS Calcd.: 264. Found: 265 (M+H).

N-(4-Bromo-2-methoxy-6-methylphenyl)-1-methyl-7-(1-propylbutyl)-1H-benzimidazol-2-amine Hydrochloride A neat mixture of 100 mg (0.38 mmol) of 2-chloro-1-methyl-7-(1-propylbutyl)-1H-benzimidazole and 163 mg (0.76 mmol) of 4-bromo-2-methoxy-6-methylphenylamine was heated at 100° C. overnight. The reaction was cooled to room temperature and the residue was dissolved in 10 mL of dichloromethane, washed with water, dried over sodium sulfate, filtered, and concentrated in vacuo. This residue thus obtained was purified by preparative HPLC to give the title compound as the trifluoroacetic acid salt. The salt was dissolved in methanol and treated with hydrochloric acid (1N solution in diethyl ether). The solution was concentrated in vacuo to give 40 mg (23%) of the title compound as the hydrochloric salt.

$^1$H NMR (CDCl$_3$) δ 0.87 (t, J=7.4 Hz, 6H), 1.26 (m, 4H), 1.71 (m, 4H), 2.12 (s, 3H), 3.40 (m, 1H), 3.82 (s, 3H), 3.89 (s, 3H), 6.93 (s, 1H), 6.97-6.99 (m, 1H), 7.03 (s, 1H), 7.09 (t, J=7.2 Hz, 1H), 7.34 (br s, 1H).

MS Calcd.: 443. Found: 444 (M+H).

Compounds described below were prepared in a similar method.

TABLE 1

| Example | Structure | Name | Physical Data |
|---|---|---|---|
| 2 | 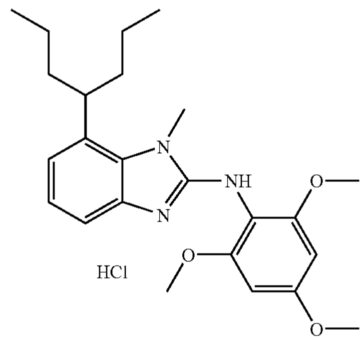 | 1-methyl-7-(1-propylbutyl)-N-(2,4,6-trimethoxyphenyl)-1H-benzimidazol-2-amine Hydrochloride | MS Calcd.: 411; Found: 412 (M + H). |
| 3 | 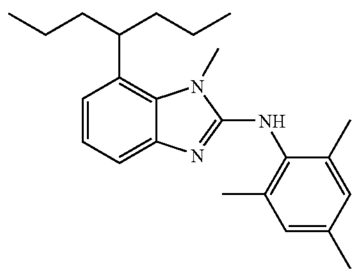 | N-mesityl-1-methyl-7-(1-propylbutyl)-1H-benzimidazol-2-amine | $^1$H NMR (CDCl$_3$) δ 0.87 (t, 6H, J = 7.0 Hz); 1.26 (br s, 6H); 1.67-1.70 (m, 4H); 2.19 (s, 4H); 2.28 (s, 3H); 3.35 (br s, 1H); 3.73 (s, 3H); 5.56 (br s, 1H); 6.92 (s, 3H); 7.07 (br s, 1H); 7.30 (br s, 1H); MS Calcd.: 363; Found: 364 (M + H). |
| 4 | 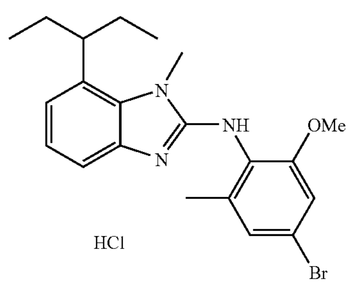 | N-(4-bromo-2-methoxy-6-methylphenyl)-7-(1-ethylpropyl)-1-methyl-1H-benzimidazol-2-amine Hydrochloride | $^1$H NMR (CDCl$_3$) δ 0.86 (t, J = 7.4 Hz, 6H), 1.70-1.83 (m, 4H), 2.12 (s, 3H), 3.21-3.27 (m, 1H), 3.82 (s, 3H), 3.89 s, 3H), 6.93 (s, 1H), 6.96 (d, J = 7.6 Hz, 1H), 7.03 (s, 1H), 7.07-7.11 (m, 1H), 7.35 (s, 1H). MS Calcd.: 415; Found: 416 (M + H). |
| 5 | 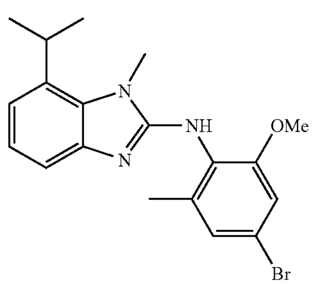 | N-(4-Bromo-2-methoxy-6-methylphenyl)-7-isopropyl-1-methyl-1H-benzimidazol-2-amine | $^1$H NMR (CDCl$_3$) δ 1.39 (d, J = 6.9 Hz, 6H), 2.12 (s, 3H), 3.82 (s, 3H), 3.86 (s, 1H), 3.93 (s, 3H), 5.87 (m, 1H), 6.92 (s, 1H), 7.00-7.10 (m, 3H), 7.36 (m, 1H). MS Calcd.: 387; Found: 388 (M + H). |
| 6 | 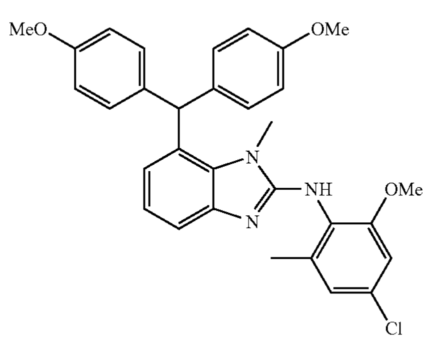 | 7-[bis(4-methoxyphenyl)methyl]-N-(4-chloro-2-methoxy-6-methylphenyl)-1-methyl-1H-benzimidazol-2-amine | $^1$H NMR (CDCl$_3$) δ 2.12 (s, 3H), 3.66 (s, 3H), 3.77 (s, 3H), 3.80 (s, 6H), 6.12 (m, 1H), 6.50 (d, J = 8.1 Hz ,1H), 6.75-6.88 (m, 6H), 6.95-7.00 (m, 5H), 7.41 (m, 1H). MS Calcd.: 529; Found: 530 (M + H). |

| Example | Structure | Name | Physical Data |
|---|---|---|---|
| 7 | 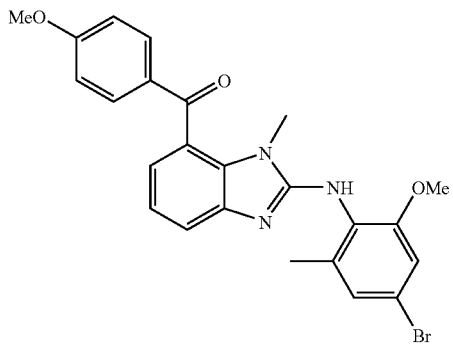 | N-(4-chloro-2-methoxy-6-methylphenyl)-7-[1-(4-methoxyphenyl)propyl]-1-methyl-1H-benzimidazol-2-amine | $^1$H NMR (CDCl$_3$) δ 0.99 (t, J = 7.2 Hz, 3H), 2.00-2.25 (m, 2H), 2.12 (s, 3H), 3.74 (s, 1H), 3.75 (s, 3H), 3.77 (s, 3H), 4.47 (t, J = 7.2 Hz, 1H), 6.76 (d, J = 2.4 Hz, 1H), 6.82(d, J = 8.7 Hz, 1H), 6.86 (d, J = 2.4 Hz, 1H), 7.05-7.20 (m, 4H), 7.37 (m, 1H). MS Calcd.: 449; Found: 450 (M + H). |

Example 8

{2-[(4-Bromo-2-methoxy-6-methylphenyl)amino]-1-methyl-1H-benzimidazol-7-yl}(4-methoxyphenyl)methanone

7-(4-Methoxybenzoyl)-1-methyl-1,3-dihydro-2H-benzimidazol-2-one

A solution of 12 mL (6.00 mmol) of 4-methoxymagnesium bromide (0.5M solution in THF) was diluted with 15 mL of THF and cooled in an ice bath. To this solution was slowly added 309 mg (1.50 mmol) of 1-methyl-2-oxo-2,3-dihydro-1H-benzimidazole-7-carboxylic acid methyl ester and the reaction was stirred for 24 h at 60° C. The reaction was quenched with water. The aqueous mixture was extracted with ethylacetate. The extract was washed with 1N aqueous hydrochloric acid and brine, dried over magnesium sulfate and concentrated in vacuo. The residue was purified by column chromatography eluting with 20-70% ethyl acetate/n-hexane to give the title compound (148 mg, 35%).

$^1$H NMR (DMSO-d$_6$) δ 3.00 (s, 3H), 3.87 (s, 3H), 6.98 (d, J=8.1 Hz, 1H), 7.00-7.15 (m, 3H), 7.19 (d, J=8.1 Hz, 1H), 7.81 (d, J=7.2 Hz, 2H).

MS Calcd.: 282. Found: 283 (M+H).

(2-Chloro-1-methyl-1H-benzimidazol-7-yl)(4-methoxyphenyl)-methanone

A mixture of 145 mg (0.514 mmol) of 7-(4-methoxybenzoyl)-1-methyl-1,3-dihydro-2H-benzimidazol-2-one was dissolved in 1.5 mL of phosphorous oxychloride and heated at 100° C. for 18 h. The reaction was allowed to cool to room temperature and concentrated in vacuo. The residue thus obtained was dissolved in ethyl acetate, washed with aqueous sodium bicarbonate, dried over magnesium sulfate, filtered and concentrated in vacuo to give 124 mg (80%) of the title compound, which was used in the next step without further purification.

MS Calcd.: 300. Found: 301 (M+H).

{2-[(4-bromo-2-methoxy-6-methylphenyl)amino]-1-methyl-1H-benzimidazol-7-yl}(4-methoxyphenyl)methanone A mixture of 120 mg (0.399 mmol) of (2-chloro-1-methyl-1H-benzimidazol-7-yl)(4-methoxyphenyl)-methanone and 216 mg (0.998 mmol) of 4-bromo-2-methoxy-6-methylphenylamine in 0.5 ml of 1-methyl-2-pyrrolidone was heated at 100° C. for 20 h. The reaction was cooled to room temperature and the residue was dissolved in dichloromethane, washed with water, dried over magnesium sulfate, filtered, and concentrated in vacuo. This residue thus obtained was purified by preparative HPLC to give the title compound as the trifluoroacetic acid salt. The salt was dissolved in ethyl acetate and washed with aqueous sodium bicarbonate, dried over magnesium sulfate, filtered and concentrated in vacuo to give 30 mg (16%) of the title compound.

$^1$H NMR (CDCl$_3$) δ 2.19 (s, 3H), 3.56 (s, 3H), 3.82 (s, 3H), 3.91 (s, 3H), 5.94 (m, 1H), 6.94 (d, J=1.8 Hz, 1H), 6.99 (d, J=8.7 Hz, 2H), 7.06 (d, J=1.8 Hz, 1H), 7.10-7.20 (m, 2H), 7.65 (d, J=6.9 Hz, 1H), 7.96 (d, J=8.7 Hz, 2H);

MS Calcd.: 481. Found: 482 (M+H).

Example 9

N-(4-Bromo-2-methoxy-6-methylphenyl)-4-(1-ethylbutyl)-3-methyl-3H-imidazo[4,5-c]pyridin-2-amine

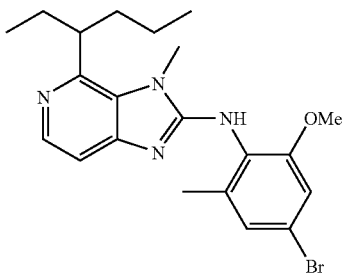

4-Bromo-3-methyl-1H-imidazo[4,5-c]pyridin-2(3H)-one

A solution of 20.0 g (103 mmol) 3-methyl-4-nitro-1H-imidazo[4,5-c]pyridin-2(3H)-one in 168 mL 48% hydrobromic acid was heated for 6 h at 135° C. An additional 33 mL of 48% hydrobromic acid was added and the reaction was stirred at 135° C. overnight. The reaction was cooled to room temperature and quenched into 1675 mL ice water. The resulting slurry was adjusted to pH 9 by the addition of 125 mL saturated aqueous ammonium hydroxide. The precipitate was filtered and washed with 200 mL water and dried in a vacuum oven at 50° C. overnight to give 17.58 g (75%) of the title product as a light yellow solids.

$^1$H NMR (DMSO-$d_6$) δ 3.54 (3H, s), 7.08 (1H, d, J=4.9 Hz), 7.94 (1H, d, J=4.9 Hz), 11.71 (1H, s).

MS Calcd.: 227. Found: 228 (M+H).

(E)-4-(Hex-3-en-3-yl)-3-methyl-1H-imidazo[4,5-c]pyridin-2(3H)-one

A mixture of 0.68 g (3.0 mmol) of 4-bromo-3-methyl-1H-imidazo[4,5-c]pyridin-2(3H)-one and 0.17 g (0.20 mmol) of PdCl$_2$dppf-dichloromethane complex was dissolved in 12 mL of toluene and treated with 3.8 mL (7.7 mmol) of 2N sodium carbonate and 0.72 g (3.6 mmol) of (Z)-2-(hex-3-en-3-yl)benzo[d][1,3,2]dioxaborole. The resulting mixture was heated to 90° C. for 5 h, partitioned between water and ethyl acetate, filtered to remove fine precipitates and extracted with ethyl acetate. The combined organic layers were washed with brine, dried over sodium sulfate, filtered and concentrated in vacuo. The brown oil thus obtained was purified by flash chromatography eluting with a 25% methanol/dichloromethane mixture to give 0.40 g (58%) of the title compound as a cream colored solid.

$^1$H NMR (CDCl$_3$) δ 1.01 (3H, t, J=7.6 Hz), 1.10 (3H, t, J=7.6 Hz), 2.29-2.36 (2H, m), 2.66 (2H, q, J=7.4 Hz), 3.46 (3H, s), 5.46 (1H, t, J=7.2 Hz), 6.98 (1H, d, J=5.3 Hz), 8.28 (1H, d, J=5.1 Hz), 10.83 (1H, br s).

MS Calcd.: 231. Found: 232 (M+H).

4-(Hexan-3-yl)-3-methyl-1H-imidazo[4,5-c]pyridin-2(3H)-one

To a solution of 0.36 g (1.6 mmol) of (E)-4-(hex-3-en-3-yl)-3-methyl-1H-imidazo[4,5-c]pyridin-2(3H)-one in 30 mL of ethanol was added 0.99 g (10 mol % Pd) of palladium on carbon (50% wet, Degussa type). The reaction was kept under a hydrogen atmosphere via a balloon and stirred at room temperature for 6 h. The catalyst was removed via filtration and the filtrate was concentrated in vacuo to give 0.33 g (91%) of the title compound as a grey oil that solidified upon standing.

$^1$H NMR (CDCl$_3$) δ 0.81 (3H, t, J=7.4 Hz), 0.87 (3H, t, J=7.4 Hz), 1.12-1.29 (2H, m), 1.66-1.82 (2H, m), 1.88-1.99 (2H, m), 3.21-3.28 (1H, m), 3.67 (3H, s), 6.94 (1H, d, J=5.2 Hz), 8.31 (1H, d, J=5.2 Hz), 10.25 (1H, br s).

MS Calcd.: 233. Found: 234 (M+H).

2-Chloro-4-(hexan-3-yl)-3-methyl-3H-imidazo[4,5-c]pyridine

Prepared from 4-(hexan-3-yl)-3-methyl-1H-imidazo[4,5-c]pyridin-2(3H)-one according to the method described previously for 2-chloro-1-methyl-7-(1-propylbutyl)-1H-benzimidazole in 68% isolated yield.

$^1$H NMR (CDCl$_3$) δ 0.80 (3H, t, J=7.4 Hz), 0.86 (3H, t, J=7.4 Hz), 1.06-1.31 (2H, m), 1.68-1.93 (2H, m), 1.95-2.04 (2H, m), 3.30-3.37 (1H, m), 4.05 (3H, s), 7.43 (1H, d, J=5.4 Hz), 8.43 (1H, d, J=5.4 Hz).

MS Calcd.: 251. Found: 252 (M+H).

N-(4-bromo-2-methoxy-6-methylphenyl)-4-(1-ethylbutyl)-3-methyl-3H-imidazo[4,5-c]pyridin-2-amine Prepared from according to the method described previously for 2-chloro-4-(hexan-3-yl)-3-methyl-3H-imidazo[4,5-c]pyridine in 47% isolated yield.

$^1$H NMR (CDCl$_3$) δ 0.84 (3H, t, J=7.4 Hz), 0.88 (3H, t, J=7.4 Hz), 1.14-1.32 (2H, m), 1.68-1.84 (2H, m), 1.93-2.02 (2H, m), 2.18 (3H, s), 3.24-3.31 (1H, m), 3.82 (3H, s), 3.90 (3H, s), 5.98 (1H, br s), 6.94 (1H, s), 7.06 (1H, s), 7.23 (1H, d, J=4.5 Hz), 8.29 (1H, d, J=5.3 Hz).

MS Calcd.: 430. Found: 431 (M+H).

Compounds described below were prepared in a similar method.

TABLE 2

| Example | Structure | Name | Physical Data |
|---|---|---|---|
| 10 | 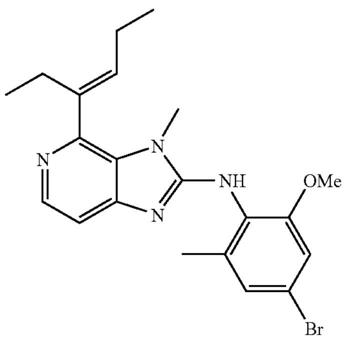 | N-(4-bromo-2-methoxy-6-methylphpenyl)-4[(1E)-1-ethylbut-1-enyl]-3-methyl-3H-imidazo[4,5-c]pyridin-2-amine | $^1$H NMR (CDCl$_3$) δ 1.04 (3H, t, J = 7.5 Hz), 1.12 (3H, t, J = 7.5 Hz), 2.22 (3H, s), 2.35 (2H, m), 2.71 (2H, q, J = 7.5 Hz), 3.71 (3H, s), 5.53 (1H, t, J = 7.5 Hz), 5.97 (1H, m), 6.94 (1H, d, J = 1.8 Hz), 7.07 (1H, d, J = 1.8 Hz), 7.28 (1H, d, J = 5.4 Hz), 8.25 (1H, d, J = 5.4 Hz). MS Calcd.: 428; Found: 429 (M + H). |
| 11 | 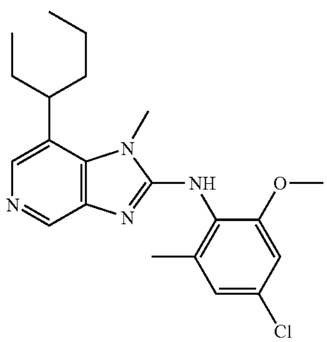 | N-(4-chloro-2-methoxy-6-methylphenyl)-7-(1-ethylbutyl-1-methyl-1H-imidazo[4,5-c]pyridin-2-amine | $^1$H NMR (CDCl$_3$) δ 0.90 (3H, t, J = 7.3 Hz) 0.89 (3H, t, J = 7.4 Hz) 1.23-1.36 (2H, m) 1.73-1.90 (4H, m) 2.18 (3H, s) 3.21-3.31 (1H, m) 3.83 (3H, s) 3.90 (3H, s) 5.93 (1H, s) 6.81 (1H, d, J = 2.2 Hz) 6.92 (1H, d, J = 1.7 Hz) 8.17 (1H, s) 8.62 (1H, s) MS Calcd.: 386; Found: 387 (M + H). |

Example 12

4-[2-[(2,4-Dimethylphenyl)amino]-1-(2-hydroxyethyl)-1H-benzimidazol-7-yl]heptan-4-ol

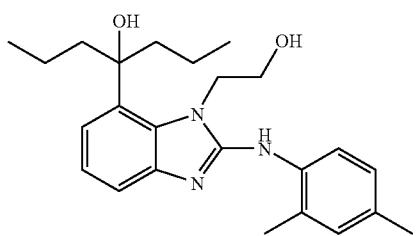

Methyl-2-chloro-3-nitrobenzoate

A slurry of 20 g (99 mmol) of 2-chloro-3-nitrobenzoic acid in 800 mL dichloromethane was cooled in an ice bath. Dimethylformamide (0.40 ml) was added to the reaction mixture followed by dropwise addition of 13.85 g (109 mmol) of oxalyl chloride. The reaction was allowed to warm to room temperature and was stirred for 6 h. Methanol (200 mL) was added dropwise and the reaction was stirred overnight. The solvent was evaporated in vacuo. The residue was triturated with n-hexane. The resulting solid was collected by filtration, washed with hexane and dried in vacuo to give 21.0 g (98%) of the title compound.

$^1$H NMR (CDCl$_3$) δ 3.98 (3H, s), 7.49 (1H, t, J=8.4 Hz), 7.84 (1H, dd, J=1.8, 8.4 Hz), 7.96 (1H, dd, J=1.8, 8.4 Hz).

Methyl 2-[(2-hydroxyethyl)amino]-3-nitrobenzoate

To a solution of 4.70 g (21.9 mmol) of methyl 2-chloro-3-nitrobenzoate in 300 mL of THF was added dropwise 300 mL of 2-ethanolamine (80 mmol) and the mixture was refluxed over night. The reaction was concentrated to dryness, dissolved in ethyl acetate, and washed aqueous sodium hydrogen carbonate and water. The organics were dried over magnesium sulfate, filtered, and concentrated in vacuo to give 5.00 g (20.8 mmol, 95%) of the title compound.

$^1$H NMR (CDCl$_3$) δ 1.68 (1H, br), 3.12 (2H, dd, J=4.8, 10.2 Hz), 3.85 (2H, t, J=4.8 Hz), 3.92 (1H, s), 6.69 (1H, t, J=8.1 Hz), 7.96 (1H, dd, J=1.8, 8.1 Hz), 8.09 (1H, dd, J=1.8, 8.1 Hz), 8.72 (1H, br).

MS Calcd.: 240. Found: 241 (M+H).

9-Nitro-2,3-dihydro-4,1-benzoxazepin-5(1H)-one

To a solution of 2.00 g (8.32 mmol) of methyl 2-[(2-hydroxyethyl)amino]-3-nitrobenzoate in 150 mL of THF was added dropwise 6N HCl (100 mL) at 0° C. and the mixture was stirred for 30 min. The reaction mixture was refluxed for 16 h. After being cooled to room temperature, the mixture was diluted with water (150 ml), and concentrated in vacuo. The residue was dissolved in ethyl acetate and washed with aqueous sodium hydrogen sulfate and water. The organics was dried over magnesium sulfate, filtered, and concentrated in vacuo to give 1.03 g (5.00 mmol, 60%) of the title compound.

$^1$H NMR (CDCl$_3$) δ: 3.91-3.95 (2H, m), 4.58-4.61 (2H, m), 6.79 (1H, t; J=8.4 Hz), 8.19 (1H, dd, J=1.8, 8.4 Hz), 8.43 (1H, dd, J=1.8, 8.4 Hz), 8.96 (1H, br).

MS Calcd.: 208. Found: 209 (M+H).

9-Amino-2,3-dihydro-4,1-benzoxazepin-5(1H)-one

A solution of 500 mg (2.42 mmol) of 9-nitro-2,3-dihydro-4,1-benzoxazepin-5(1H)-one in 500 mL of methanol was inerted with nitrogen. To this solution was added 100 mg of 10% palladium on carbon (50% wet) and the reaction was purged with hydrogen and stirred under balloon pressure hydrogen for 6 h. The catalyst was removed by filtration and the filtrate was concentrated in vacuo to give 430 mg (99%) of the title compound.

$^1$H NMR (CD$_3$OD) δ: 3.00-3.03 (2H, m), 3.77-3.80 (2H, m), 5.95 (1H, t, J=8.4 Hz), 6.25 (1H, dd, J=1.5, 8.4 Hz), 6.56 (1H, dd, J=1.5, 8.4 Hz).

MS Calcd.: 178. Found: 179 (M+H).

4,5-Dihydro-7H-imidazo[4,5,1-jk][4,1]benzoxazepine-2,7(1H)-dione

To a solution of 200 mg (1.13 mmol) of 9-amino-2,3-dihydro-4,1-benzoxazepin-5(1H)-one in 20 mL of THF was added 280 mg (2 mmol) of 1,1'-carbonyldiimidazole and the reaction mixture was stirred overnight at room temperature. The reaction mixture was heated at 50° C. for 4 h and allowed to cool to room temperature. The reaction was concentrated in vacuo and the residue was dissolved in a mixture of ethyl acetate/n-hexane (1:1) and washed with water. The organics were dried over sodium sulfate, filtered, and concentrated in vacuo to give 286 mg (1.40 mmol, 70%) of the title compound.

$^1$H NMR (CD$_3$OD) δ: 4.25-4.27 (2H, m), 4.75-4.77 (2H, m), 7.23 (1H, t, J=8.4 Hz), 7.37 (1H, dd, J=1.2, 8.4 Hz), 7.78 (1H, dd, J=1.5, 8.4 Hz).

MS Calcd.: 204. Found: 205 (M+H).

2-Chloro-4,5-dihydro-7H-imidaz[4,5,1-jk][4,1]benzoxazepin-7-one 4,5-Dihydro-7H-imidazo[4,5,1-jk][4,1]benzoxazepine-2,7(1H)-dione (1.00 g, 4.89 mmol) was dissolved in 15 mL of phosphorous oxychloride and heated at 110° C. for 6 h. The reaction allowed to cool to room temperature, poured into water with an ice, and stirred for 1 h. The aqueous solution was extracted with ethyl acetate. The extract was washed with aqueous sodium bicarbonate, dried over magnesium sulfate, filtered and concentrated in vacuo to give 1.06 g (98%) of the title compound, which was used in the next reaction without further purification.

MS Calcd.: 222. Found: 223 (M+H).

2-[(2,4-Dimethylphenyl)amino]-4,5-dihydro-7H-imidazo[4,5,1-jk][4,1]benzoxazepin-7-one A mixture of 2-chloro-4,5-dihydro-7H-imidaz[4,5,1-jk][4,1]benzoxazepin-7-one 1.06 g (4.77 mmol) and 2,4-methylaniline 1.73 g (14.3 mmol) in 0.1 ml of N-methyl-2-pyrrolidone was heated at 100° C. overnight. The reaction was cooled to room temperature and the residue was dissolved in dichloromethane, washed with sodium bicarbonate and water, dried over magnesium sulfate, filtered, and concentrated in vacuo. The residue was triturated with ethyl acetate/n-hexane (1:1) to give 0.96 g (66%) of the title compound.

$^1$H NMR (CDCl$_3$) δ: 2.14 (3H, s), 2.22 (3H, s), 4.35-4.37 (2H, m), 4.78-4.80 (2H, m), 5.98 (1H, br), 6.59 (1H, d, J=7.2 Hz), 6.84 (1H, d, J=7.2 Hz), 6.87 (1H, s), 7.24 (1H, t, J=7.8 Hz), 7.72 (1H, d, J=7.8 Hz), 7.86 (1H, d, J=7.8 Hz).

MS Calcd.: 307. Found: 308 (M+H).

4-[2-[(2,4-Dimethylphenyl)amino]-1-(2-hydroxyethyl)-1H-benzimidazol-7-yl]heptan-4-ol To a refluxing solution of 30 mL of n-propylmagnesium bromide (27% in tetrahydrofuran) was added 500 mg (1.63 mmol) of 2-[(2,4-dimethylphenyl)amino]-4,5-dihydro-7H-imidazo[4,5,1-jk][4,1]benzoxazepin-7-one and the mixture was refluxed for 1 h. The reaction mixture was cooled to room temperature and diluted with 50 mL of water and neutralization with 1N HCl. The aqueous solution was extracted with ethyl acetate. The extract was dried over magnesium sulfate, filtered, and concentrated in vacuo. The residue thus obtained was purified by preparative HPLC to give the title compound as the trifluoroacetic acid salt. The salt was dissolved in ethyl acetate and washed with aqueous sodium bicarbonate, dried over magnesium sulfate, filtered and concentrated in vacuo to give 161 mg (0.41 mmol, 25%) of the title compound.

$^1$H NMR (CDCl$_3$) δ: 0.92 (6H, t, J=7.5 Hz), 1.23-1.41 (4H, m), 1.81-1.91 (2H, m), 1.98-2.09 (2H, m), 2.13 (3H, s), 2.22 (3H, s), 4.21 (2H, t, J=4.8 Hz), 4.45 (2H, t, J=4.8 Hz), 6.59 (1H, d, J=7.2 Hz), 6.84 (1H, d, J=7.2 Hz), 6.87 (1H, s), 6.83 (1H, d, J=8.1 Hz), 7.03 (1H, t, J=8.1 Hz), 7.41 (1H, d, J=8.1 Hz).

MS Calcd.: 395. Found: 396 (M+H).

Compounds described below were prepared in a similar method.

TABLE 3

| Example | Structure | Name | Physical Data |
| --- | --- | --- | --- |
| 13 | 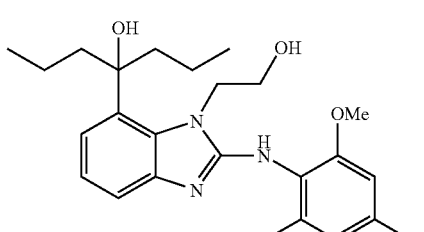 | 4-[2-[(4-chloro-2-methoxy-6-methylphenyl)amino]-1-(2-hydroxyethyl)-1H-benzimidazol-7-yl]heptan-4-ol | $^1$H NMR (CDCl$_3$) δ 0.92 (6H, t, J = 7.5 Hz), 1.23-1.41 (4H, m), 1.81-1.91 (2H, m), 1.98-2.09 (2H, m), 2.21 (3H, s), 3.81 (3H, s), 4.21 (2H, t, J = 4.8 Hz), 4.45 (2H, t, J = 4.8 Hz), 6.82 (1H, d, J = 2.1 Hz), 6.92 (1H, d, J = 2.1 Hz), 6.83 (1H, d, J = 8.1 Hz), 7.03 (1H, t, J = 8.1 Hz), 7.41 (1H, d, J = 8.1 Hz). MS Calcd.: 445; Found: 446 (M + H). |

Example 14

2-[2-[(2,4-Dimethylphenyl)amino]-7-(1-propylbutyl)-1H-benzimidazol-1-yl]ethanol

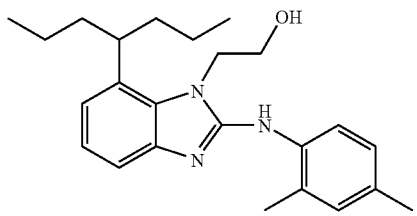

A solution of 100 mg (0.25 mmol) of 9-nitro-2,3-dihydro-4,1-benzoxazepin-5(1H)-one in 3 mL of ethanol was inerted with nitrogen. To this solution was added an ethanol solution of Raney nickel and the reaction was purged with hydrogen and stirred under balloon pressure hydrogen for 6 h. The catalyst was removed by filtration and the filtrate was concentrated in vacuo. The residue thus obtained was purified by preparative HPLC to give the title compound as the trifluoroacetic acid salt. The salt was dissolved in ethyl acetate and washed with aqueous sodium bicarbonate, dried over magnesium sulfate, filtered and concentrated in vacuo to give 27 mg (0.07 mmol, 28%) of the title compound.

$^1$H NMR (CDCl$_3$) δ: 0.92 (6H, t, J=7.5 Hz), 1.22-1.41 (4H, m), 1.79-1.89 (2H, m), 1.98-2.09 (2H, m), 2.12 (3H, s), 2.22 (3H, s), 2.87 (1H, q, J=7.2 Hz), 4.21 (2H, t, J=4.8 Hz), 4.45 (2H, t, J=4.8 Hz), 6.59 (1H, d, J=7.2 Hz), 6.84 (1H, d, J=7.2 Hz), 6.87 (1H, s), 6.85 (1H, d, J=8.1 Hz), 7.05 (1H, t, J=8.1 Hz), 7.45 (1H, d, J=8.1 Hz).

MS Calcd.: 379. Found: 380 (M+H).

Example 15

N-(4-Chloro-2-methoxy-6-methylphenyl)-7-(2-ethylphenyl)-1-methyl-1H-benzimidazol-2-amine

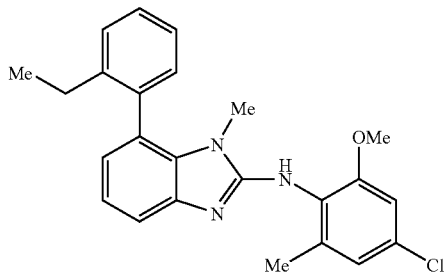

7-Bromo-2-chloro-1-methyl-1H-benzimidazole

7-Bromo-1-methyl-1,3-dihydro-2H-benzimidazol-2-one (2.20 g, 9.69 mmol) was dissolved in 30 mL of phosphorous oxychloride and the mixture was heated at 110° C. for 2 days. The reaction allowed to cool to room temperature, poured into water with an ice, and stirred for 1 h. The aqueous solution was extracted with ethyl acetate. The extract was washed with aqueous sodium bicarbonate, dried over magnesium sulfate, filtered and concentrated in vacuo to give 2.32 g of the title compound, which was used in the next reaction without further purification.

MS Calcd.: 243. Found: 244 (M+H).

7-Bromo-N-(4-chloro-2-methoxy-6-methylphenyl)-1-methyl-1H-benzimidazol-2-amine

To a mixture of 7-bromo-1-methyl-1,3-dihydro-2H-benzimidazol-2-one 2.32 g (9.69 mmol) and 4-chloro-2-methoxy-6-methylaniline 4.98 g (29.1 mmol) in 0.5 mL of N-methyl-2-pyrrolidone was heated at 110° C. for 2 days. The reaction was cooled to room temperature and diluted with dichloromethane. The mixture was washed with sodium bicarbonate and water, dried over magnesium sulfate, filtered, and concentrated in vacuo. The residue was triturated with ethyl acetate/hexane (1:1) to give 3.13 g (8.23 mmol, 85%) of the title compound.

$^1$H NMR (CDCl$_3$) δ: 2.17 (3H, s), 3.82 (3H, s), 4.04 (3H, s), 6.80 (1H, d, J=2.4 Hz), 6.89 (1H, d, J=2.4 Hz), 6.56 (1H, t, J=8.1 Hz), 7.21 (1H, d, J=8.1 Hz), 7.42 (1H, d, J=8.1 Hz).

MS Calcd.: 379. Found: 380 (M+H).

N-(4-Chloro-2-methoxy-6-methylphenyl)-7-(2-ethylphenyl)-1-methyl-1H-benzimidazol-2-amine trifluoroacetic acid salt To a mixture of 25 mg (65.6 μmol) of 7-bromo-N-(4-chloro-2-methoxy-6-methylphenyl)-1-methyl-1H-benzimidazol-2-amine, 11.8 mg (78.7 μmol) of 2-ethylphenylboronic acid, 12.0 mg (13.1 μmol) of tris(dibenzylideneacetone)dipalladium and 12.5 mg (26.2 μmol) of 2-(dicyclohexylphosphino)-2',4',6'-tri-1-propyl-1,1'-biphenyl in 1 mL of 1,2-dimethoxyethane was added 131 μl of 1M aqueous potassium phosphate tribasic solution. The reaction mixture was heated by microwave irradiation at 130° C. for 10 min, and allowed to cool to room temperature. The reaction mixture was diluted with dichloromethane and water, separated with a filter tube (made by Wattmann) and concentrated in vacuo. The residue was purified by preparative HPLC to give 2.5 mg (9.8%) of the title compound as a trifluoroacetic acid salt.

$^1$H NMR (CDCl$_3$) δ: 1.05 (3H, t, J=7.5 Hz), 2.17 (3H, s), 2.40-2.54 (2H, m), 3.07 (3H, s), 3.80 (3H, s), 6.78 (1H, d, J=2.4 Hz), 6.89 (1H, d, J=2.4 Hz), 6.89 (1H, d, J=7.8 Hz), 7.13 (1H, t, J=7.8 Hz), 7.23-7.41 (4H, m), 7.51 (1H, d, J=7.8 Hz).

MS Calcd.: 405. Found: 406 (M+H).

Example 16-60

Examples 16-54 in Table 4 were prepared as trifluoroacetic acid salt and examples 55-60 were prepared as free base in the similar method described in Example 15.

TABLE 4

| Example | Structure | Name | Physical Data |
| --- | --- | --- | --- |
| 16 | 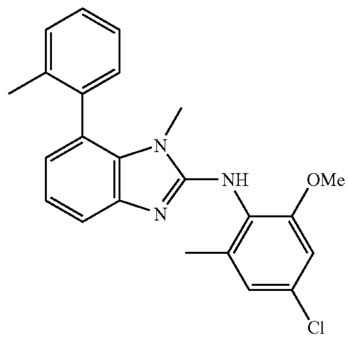 | N-(4-chloro-2-methoxy-6-methylphenyl)-1-methyl-7-(2-methylphenyl)-1H-benzimidazol-2-amine | MS Calcd.: 391; Found: 392 (M + H). |
| 17 | 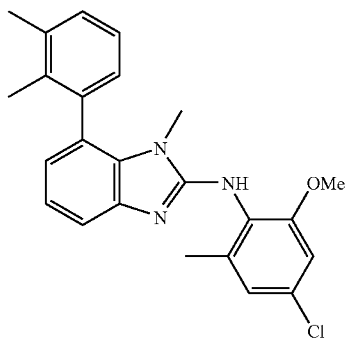 | N-(4-chloro-2-methoxy-6-methylphenyl)-7-(2,3-dimethylphenyl)-1-methyl-1H-benzimidazol-2-amine | MS Calcd.: 405; Found: 406 (M + H). |
| 18 | 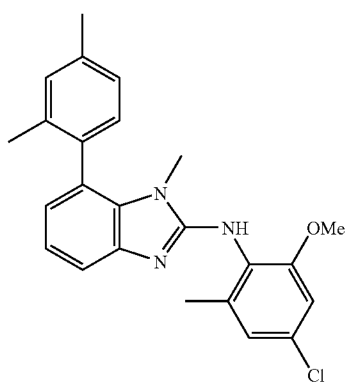 | N-(4-chloro-2-methoxy-6-methylphenyl)-7-(2,4-dimethylphenyl)-1-methyl-1H-benzimidazol-2-amine | MS Calcd.: 405; Found: 406 (M + H). |
| 19 | 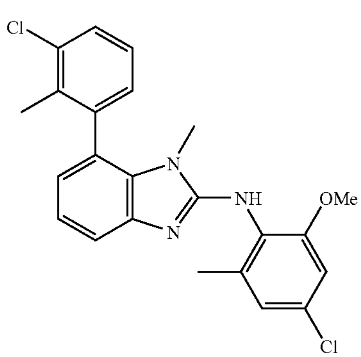 | N-(4-chloro-2-methoxy-6-methylphenyl)-7-(3-chloro-2-methylphenyl)-1-methyl-1H-benzimidazol-2-amine | MS Calcd.: 425; Found: 426 (M + H). |

TABLE 4-continued

| Example | Structure | Name | Physical Data |
|---|---|---|---|
| 20 | 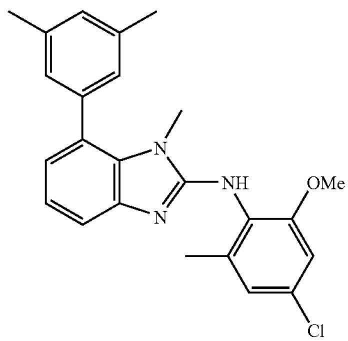 | N-(4-chloro-2-methoxy-6-methylphenyl)-7-(3,5-dimethylphenyl)-1-methyl-1H-benzimidazol-2-amine | MS Calcd.: 405; Found: 406 (M + H). |
| 21 | 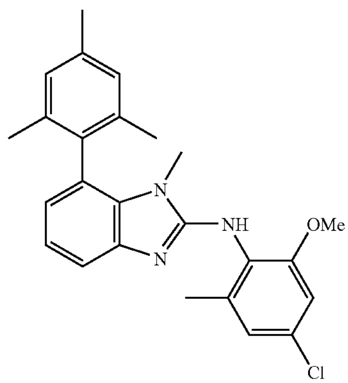 | N-(4-chloro-2-methoxy-6-methylphenyl)-7-mesityl-1-methyl-1H-benzimidazol-2-amine | MS Calcd.: 419; Found: 420 (M + H). |
| 22 | 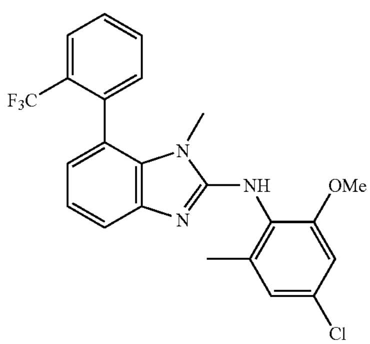 | N-(4-chloro-2-methoxy-6-methylphenyl)-1-methyl-7-[2-(trifluoromethyl)phenyl]-1H-benzimidazol-2-amine | MS Calcd.: 445; Found: 446 (M + H). |
| 23 | 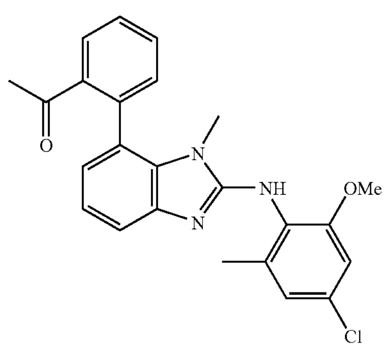 | 1-(2-{2-[(4-chloro-2-methoxy-6-methylphenyl)amino]-1-methyl-1H-benzimidazol-7-yl}phenyl)ethanone | MS Calcd.: 419; Found: 420 (M + H). |

TABLE 4-continued

| Example | Structure | Name | Physical Data |
|---|---|---|---|
| 24 | 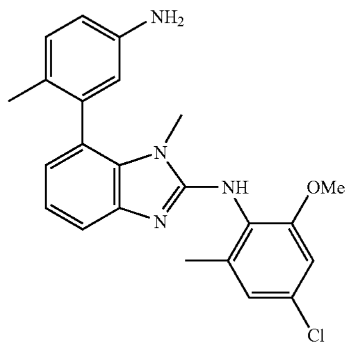 | 7-(5-amino-2-methylphenyl)-N-(4-chloro-2-methoxy-6-methylphenyl)-1-methyl-1H-benzimidazol-2-amine | MS Calcd.: 406; Found: 407 (M + H). |
| 25 | 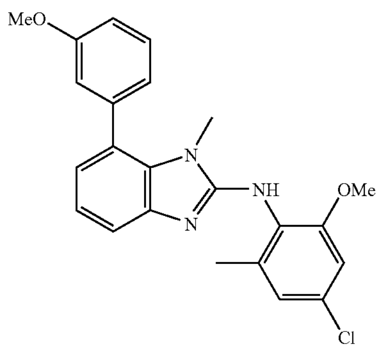 | N-(4-chloro-2-methoxy-6-methylphenyl)-7-(3-methoxyphenyl)-1-methyl-1H-benzimidazol-2-amine | MS Calcd.: 407; Found: 408 (M + H). |
| 26 | 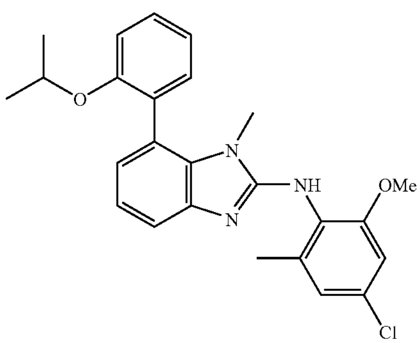 | N-(4-chloro-2-methoxy-6-methylphenyl)-7-(2-isopropoxyphenyl)-1-methyl-1H-benzimidazol-2-amine | MS Calcd.: 435; Found: 436 (M + H). |
| 27 | 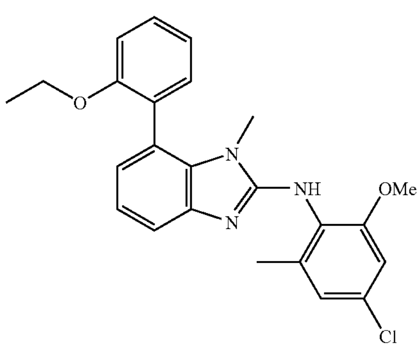 | N-(4-chloro-2-methoxy-6-methylphenyl)-7-(2-ethoxyphenyl)-1-methyl-1H-benzimidazol-2-amine | MS Calcd.: 421; Found: 422 (M + H). |

TABLE 4-continued

| Example | Structure | Name | Physical Data |
|---|---|---|---|
| 28 | 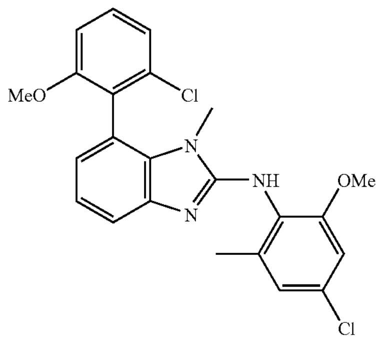 | N-(4-chloro-2-methoxy-6-methylphenyl)-7-(2-chloro-6-methoxyphenyl)-1-methyl-1H-benzimidazol-2-amine | MS Calcd.: 441; Found: 442 (M + H). |
| 29 | 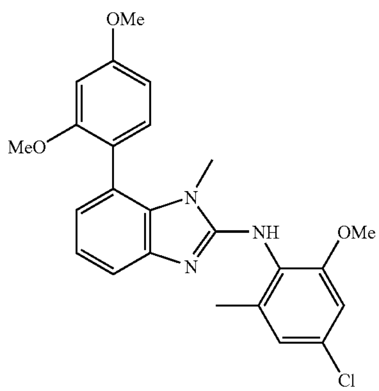 | N-(4-chloro-2-methoxy-6-methylphenyl)-7-(2,4-dimethoxyphenyl)-1-methyl-1H-benzimidazol-2-amine | MS Calcd.: 437; Found: 438 (M + H). |
| 30 | 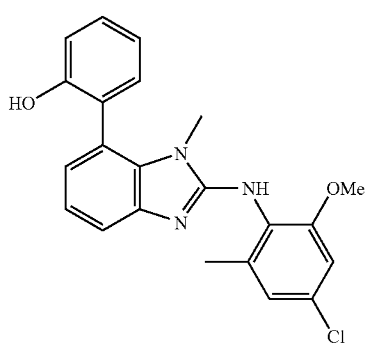 | 2-{2-[(4-chloro-2-methoxy-6-methylphenyl)amino]-1-methyl-1H-benzimidazol-7-yl}phenol | MS Calcd.: 393; Found: 394 (M + H). |
| 31 | 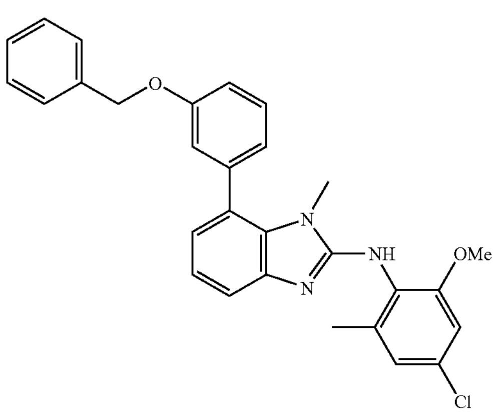 | 7-[3-(benzyloxy)phenyl]-N-(4-chloro-2-methoxy-6-methylphenyl)-1-methyl-1H-benzimidazol-2-amine | MS Calcd.: 483; Found: 484 (M + H). |

TABLE 4-continued

| Example | Structure | Name | Physical Data |
|---|---|---|---|
| 32 | 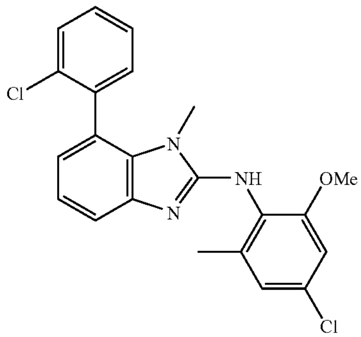 | N-(4-chloro-2-methoxy-6-methylphenyl)-7-(2-chlorophenyl)-1-methyl-1H-benzimidazol-2-amine | MS Calcd.: 411; Found: 412 (M + H). |
| 33 | 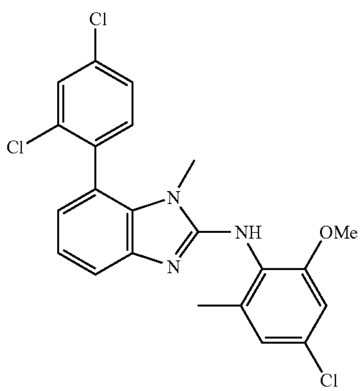 | N-(4-chloro-2-methoxy-6-methylphenyl)-7-(2,4-dichlorophenyl)-1-methyl-1H-benzimidazol-2-amine | MS Calcd.: 445; Found: 446 (M + H). |
| 34 | 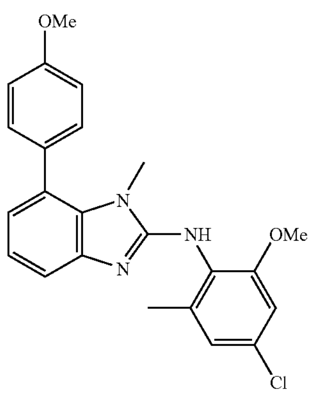 | N-(4-chloro-2-methoxy-6-methylphenyl)-7-(4-methoxyphenyl)-1-methyl-1H-benzimidazol-2-amine | MS Calcd.: 407; Found: 408 (M + H). |
| 35 | 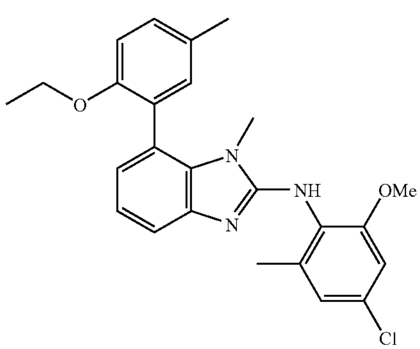 | N-(4-chloro-2-methoxy-6-methylphenyl)-7-(2-ethoxy-5-methylphenyl)-1-methyl-1H-benzimidazol-2-amine | MS Calcd.: 435; Found: 436 (M + H). |

TABLE 4-continued

| Example | Structure | Name | Physical Data |
|---|---|---|---|
| 36 | 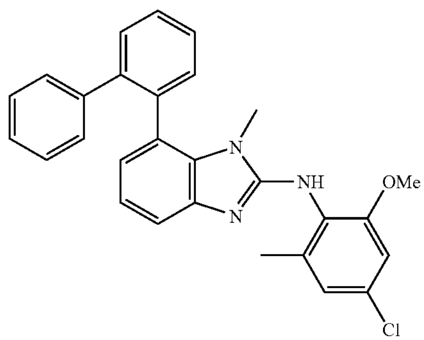 | 7-(1,1'-biphenyl-2-yl)-N-(4-chloro-2-methoxy-6-methylphenyl)-1-methyl-1H-benzimidazol-2-amine | MS Calcd.: 453; Found: 454 (M + H). |
| 37 | 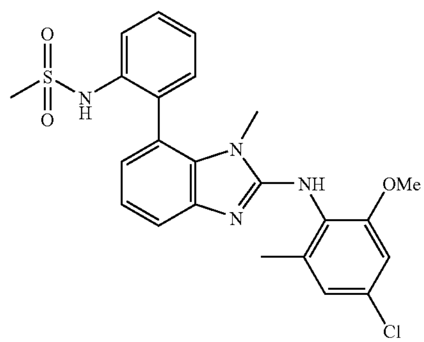 | N-(2-{2-[(4-chloro-2-methoxy-6-methylphenyl)amino]-1-methyl-1H-benzimidazol-7-yl}phenyl)methanesulfonamide | MS Calcd.: 470; Found: 471 (M + H). |
| 38 | 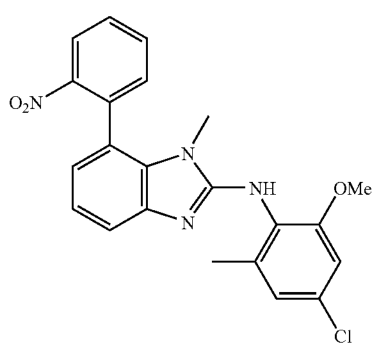 | N-(4-chloro-2-methoxy-6-methylphenyl)-1-methyl-7-(2-nitrophenyl)-1H-benzimidazol-2-amide | MS Calcd.: 422; Found: 423 (M + H). |
| 39 | 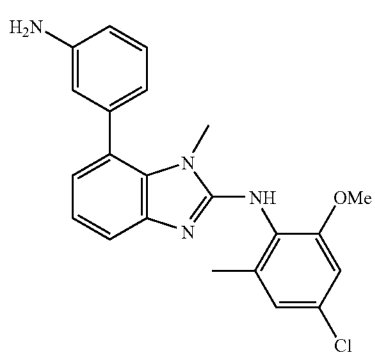 | 7-(3-aminophenyl)-N-(4-chloro-2-methoxy-6-methylphenyl)-1-methyl-1H-benzimidazol-2-amine | MS Calcd.: 392; Found: 393 (M + H). |

TABLE 4-continued

| Example | Structure | Name | Physical Data |
| --- | --- | --- | --- |
| 40 | 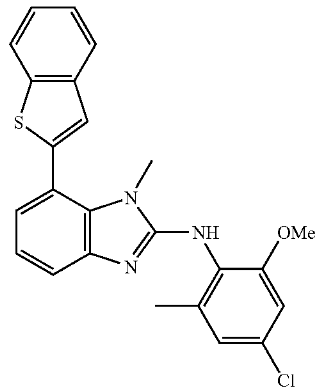 | 7-(1-benzothien-2-yl)-N-(4-chloro-2-methoxy-6-methylphenyl)-1-methyl-1H-benzimidazol-2-amine | MS Calcd.: 433; Found: 434 (M + H). |
| 41 | 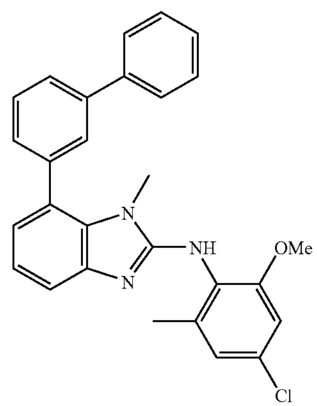 | 7-(1,1'-biphenyl-3-yl)-N-(4-chloro-2-methoxy-6-methylphenyl)-1-methyl-1H-benzimidazol-2-amine | MS Calcd.: 453; Found: 454 (M + H). |
| 42 | 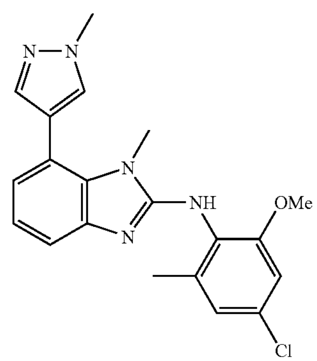 | N-(4-chloro-2-methoxy-6-methylphenyl)-1-methyl-7-(1-methyl-1H-pyrazol-4-yl)-1H-benzimidazol-2-amine | MS Calcd.: 381; Found: 382 (M + H). |
| 43 | 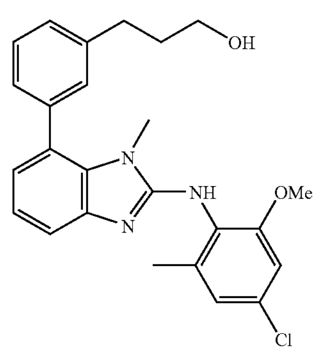 | 3-(3-{2-[(4-chloro-2-methoxy-6-methylphenyl)amino]-1-methyl-1H-benzimidazol-7-yl}phenyl)propan-1-ol | MS Calcd.: 435; Found: 436 (M + H). |

TABLE 4-continued

| Example | Structure | Name | Physical Data |
| --- | --- | --- | --- |
| 44 | 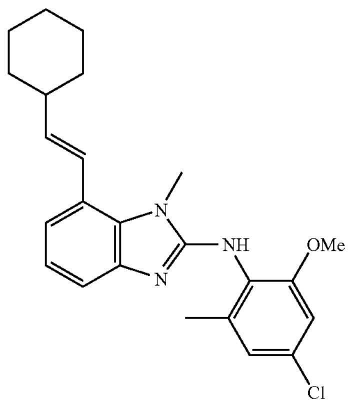 | N-(4-chloro-2-methoxy-6-methylphenyl)-7-[(E)-2-cyclohexylvinyl]-1-methyl-1H-benzimidazol-2-amine | MS Calcd.: 409; Found: 410 (M + H). |
| 45 | 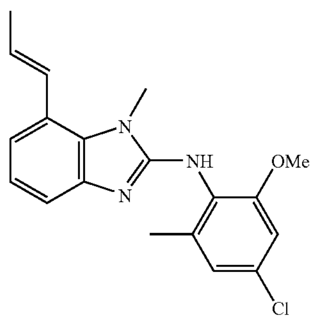 | N-(4-chloro-2-methoxy-6-methylphenyl)-1-methyl-7-[(1E)-prop-1-enyl]-1H-benzimidazol-2-amine | MS Calcd.: 341; Found: 342 (M + H). |
| 46 | 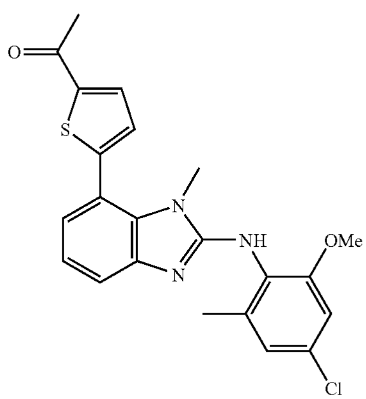 | 1-(5-{2-[(4-chloro-2-methoxy-6-methylphenyl)amino]-1-methyl-1H-benzimidazol-7-yl}thien-2-yl)ethanone | MS Calcd.: 425; Found: 426 (M + H). |
| 47 | 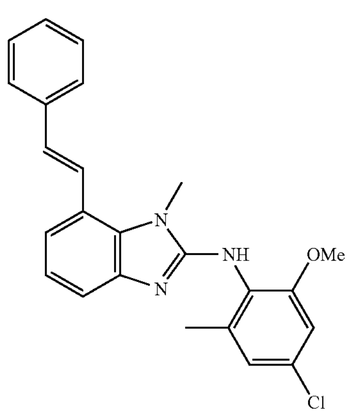 | N-(4-chloro-2-methoxy-6-methylphenyl)-1-methyl-7-[(E)-2-phenylvinyl]-1H-benzimidazol-2-amine | MS Calcd.: 403; Found: 404 (M + H). |

TABLE 4-continued

| Example | Structure | Name | Physical Data |
|---------|-----------|------|---------------|
| 48 | 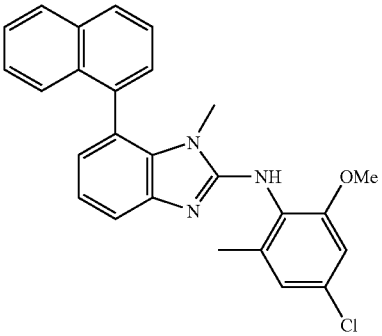 | N-(4-chloro-2-methoxy-6-methylphenyl)-1-methyl-7-(1-naphthyl)-1H-benzimidazol-2-amine | MS Calcd.: 427; Found: 428 (M + H). |
| 49 | 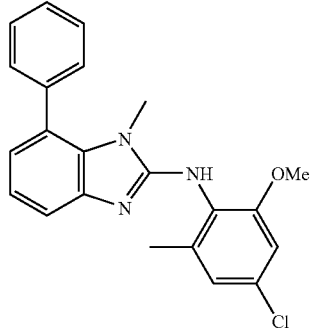 | N-(4-chloro-2-methoxy-6-methylphenyl)-1-methyl-7-phenyl-1H-benzimidazol-2-amine | MS Calcd.: 377; Found: 378 (M + H). |
| 50 | 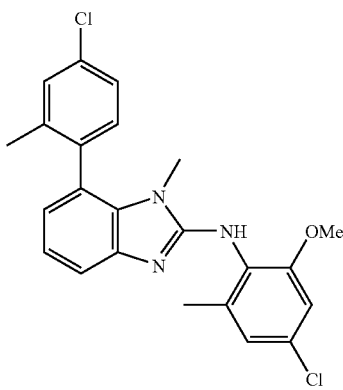 | N-(4-chloro-2-methoxy-6-methylphenyl)-7-(4-chloro-2-methylphenyl)-1-methyl-1H-benzimidazol-2-amine | MS Calcd.: 425; Found: 426 (M + H). |
| 51 | 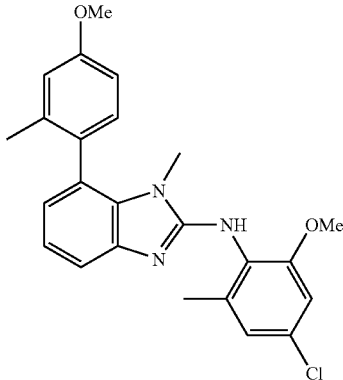 | N-(4-chloro-2-methoxy-6-methylphenyl)-7-(4-methoxy-2-methylphenyl)-1-methyl-1H-benzimidazol-2-amine | MS Calcd.: 421; Found: 422 (M + H). |

TABLE 4-continued

| Example | Structure | Name | Physical Data |
|---|---|---|---|
| 52 | 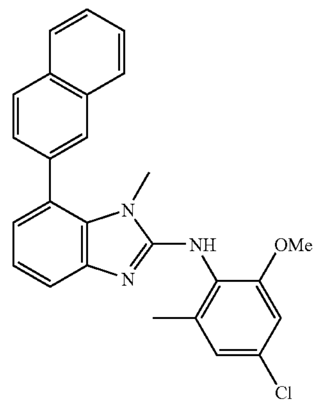 | N-(4-chloro-2-methoxy-6-methylphenyl)-1-methyl-7-(2-naphthyl)-1H-benzimidazol-2-amine | MS Calcd.: 427; Found: 428 (M + H). |
| 53 | 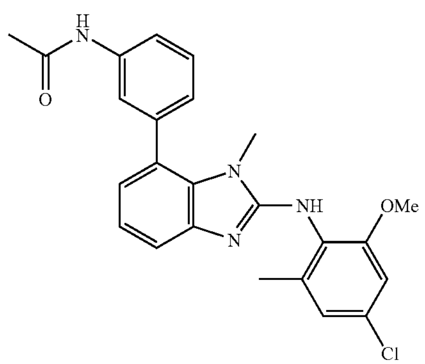 | N-(3-{2-[(4-chloro-2-methoxy-6-methylphenyl)amino]-1-methyl-1H-benzimidazol-7-yl}phenyl)acetamide | MS Calcd.: 434; Found: 435 (M + H). |
| 54 | 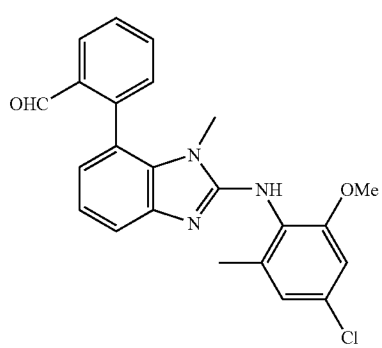 | 2-{2-[(4-chloro-2-methoxy-6-methylphenyl)amino]-1-methyl-1H-benzimidazol-7-yl}benzaldehyde | MS Calcd.: 405; Found: 406 (M + H). |
| 55 | 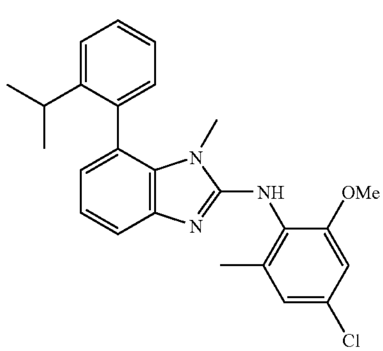 | N-(4-chloro-2-methoxy-6-methylphenyl)-7-(2-isopropylphenyl)-1-methyl-1H-benzimidazol-2-amine | $^1$H NMR (CDCl$_3$) δ 1.11 (3H, d, J = 6.9 Hz), 1.15 (3H, d, J = 6.9 Hz), 2.18 (3H, s), 2.80-2.95 (1H, m), 3.09 (3H, s), 3.81 (3H, s), 5.79 (1H, s), 6.78 (1H, d, J = 2.1 Hz), 6.87-6.89 (2H, m), 7.12 1H, t, J = 7.5 Hz), 7.20-7.30 (2H, m), 7.42-7.43 (2H, m), 7.52 (1H, d, J = 7.5 Hz). MS Calcd.: 419; Found: 420 (M + H). |

TABLE 4-continued

| Example | Structure | Name | Physical Data |
|---------|-----------|------|---------------|
| 56 | 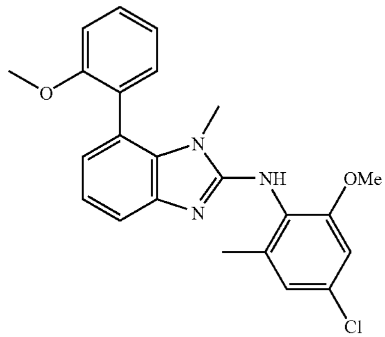 | N-(4-chloro-2-methoxy-6-methylphenyl)-7-(2-methoxyphenyl-1-methyl-1H-benzimidazol-2-amine | $^1$H NMR (DMSO-$d_6$) δ 2.09 (3H, s), 3.15 (3H, s), 3.74 (3H, s), 3.76 (3H, s), 6.68 (1H, d, J = 7.8 Hz), 6.96-7.14 (6H, m), 7.28 (1H, d, J = 7.8 Hz), 7.44 (1H, t, J = 7.8 Hz), 7.90 (1H, s). MS Calcd.: 407; Found: 408 (M + H). |
| 57 | 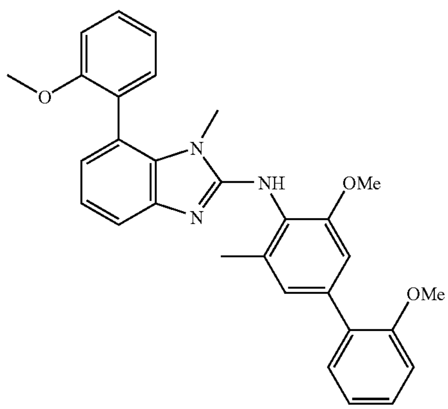 | N-2',3-dimethoxy-5-methyl-1,1'-biphenyl-4-yl)-7-(2-methoxyphenyl)-1-methyl-1H-benzimidazol-2-amine | $^1$H NMR (DMSO-$d_6$) δ 2.13 (3H, s), 3.15 (3H, s), 3.75 (6H, s), 3.81 (3H, s), 6.67 (1H, dd, J = 7.5, 1.2 Hz), 6.94-7.15 (8H, m), 7.27-7.47 (4H, m), 7.86 (1H, s). MS Calcd.: 479; Found: 480 (M + H). |
| 58 | 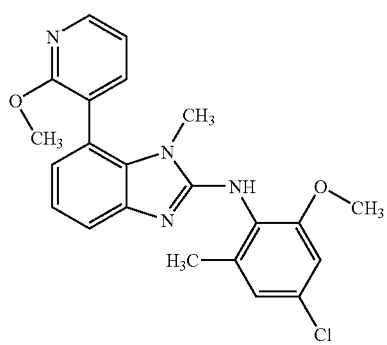 | N-(4-chloro-2-methoxy-6-methylphenyl)-7-(2-methoxypyridin-3-yl)-1-methyl-1H-benzimidazol-2-amine | $^1$H NMR (CDCl$_3$-CD$_3$OD) δ 2.19 (3H, s), 3.27 (3H, s), 3.81 (3H, s), 3.94 (3H, s), 6.84-6.90 (3H, m), 7.07-7.14 (2H, m), 7.33 (1H, d, J = 8.4 Hz), 7.70 (1H, d, J = 7.5, 1.8 Hz), 8.23 (1H, dd, J = 5.4, 1.8 Hz). MS Calcd.: 408; Found: 409 (M + H). |
| 59 | 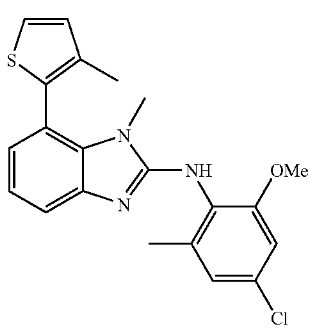 | N-(4-chloro-2-methoxy-6-methylphenyl)-1-methyl-7-(3-methyl-2-thienyl)-1H-benzimidazol-2-amine | $^1$H NMR (CDCl$_3$-CD$_3$OD) δ 2.07 (3H, s), 2.17 (3H, s), 3.21 (3H, s), 3.81 (3H, s), 5.81 (1H, s), 6.78 (1H, d, J = 2.1 Hz), 6.88-6.91 (2H, m), 7.05-7.14 (2H, m), 7.22 (1H, d, J = 3.0 Hz), 7.51 (1H, d, J = 8.1 Hz). MS Calcd.: 397; Found: 398 (M + H). |

TABLE 4-continued

| Example | Structure | Name | Physical Data |
|---|---|---|---|
| 60 | 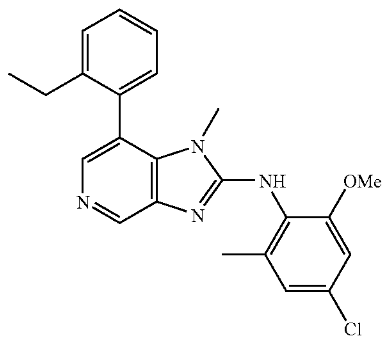 | N-(4-chloro-2-methoxy-6-methylphenyl)-7-(2-ethylphenyl)-1-methyl-1H-imidazo[4,5-c]pyridin-2-amine | $^1$H NMR (CDCl$_3$) δ 1.07 (3H, t, J = 7.6 Hz), 2.23 (3H, s), 2.40-2.59 (2H, m), 3.17 (3H, s), 3.82 (3H, s), 5.88 (1H, s), 6.81 (1H, d, J = 1.5 Hz), 6.93 (1H, d, J = 1.5 Hz), 7.20-7.51 (4H, m), 8.09 (1H, s), 8.77 (1H, s). MS Calcd.: 406; Found: 407 (M + H). |

Example 61

N-(4-Bromo-2-methoxy-6-methylphenyl)-7-(2-ethylphenyl)-1-methyl-1H-benzimidazol-2-amine

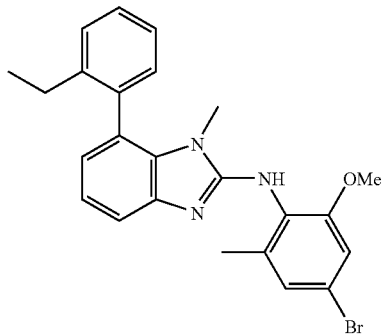

7-(2-Ethylphenyl)-1-methyl-1,3-dihydro-2H-benzimidazol-2-one

A mixture of 280 mg (1.23 mmol) of 7-bromo-1-methyl-1,3-dihydro-2H-benzimidazol-2-one, 222 mg (1.48 mmol) of 2-ethylphenylboronic acid, 113 mg (0.0123 mmol) of tris(dibenzylideneacetone)dipalladium, 29 mg (0.0615 mmol) of X-Phos and 522 mg (2.46 mmol) of potassium phosphate in 9 mL of toluene was stirred at 100° C. for 4 hours. After cooling, the reaction mixture was diluted with water and ethyl acetate and passed through celite. The filtrate was extracted with ethyl acetate (X2). The combined organic layer was washed with brine (X1), dried over sodium sulfate and concentrated in vacuo. The residue was purified by silica gel column chromatography eluting with a 25-65% ethylacetate/n-hexane gradient mixture to give 200 mg (64%) of the title compound.

$^1$H NMR (CDCl$_3$) δ 1.04 (3H, t, J=7.7 Hz), 2.34-2.52 (2H, m), 2.84 (3H, s), 6.86-6.98 (2H, m), 7.05-7.08 (2H, m), 7.18-7.39 (3H, m), 8.58 (1H, br s).

MS Calcd.: 252. Found: 253 (M+H).

2-Chloro-7-(2-ethylphenyl)-1-methyl-1H-benzimidazole

A mixture of 190 mg (0.753 mmol) of 7-(2-ethylphenyl)-1-methyl-1,3-dihydro-2H-benzimidazol-2-one and 1.5 mL of phosphorus oxychloride was stirred at 80° C. for 5 hours. After cooling, the reaction mixture was poured into ice and neutralized by 12 N sodium hydroxide. The aqueous suspension was extracted with ethyl acetate (X2). The combined organic layer was washed with brine (X1), dried over sodium sulfate and concentrated in vacuo. The residue was purified by silica gel column chromatography eluting with a 3-10% ethylacetate/n-hexane gradient mixture to give 123 mg (60%) of the title compound.

$^1$H NMR (CDCl$_3$) δ 1.02 (3H, t, J=7.5 Hz), 2.30-2.48 (2H, m), 3.19 (3H, s), 7.05-7.15 (1H, m), 7.26-7.45 (5H, m), 7.60 (1H, m).

MS Calcd.: 270, 272. Found: 271, 273 (M+H).

N-(4-Bromo-2-methoxy-6-methylphenyl)-7-(2-ethylphenyl)-1-methyl-1H-benzimidazol-2-amine A mixture of 100 mg (0.369 mmol) of 2-chloro-7-(2-ethylphenyl)-1-methyl-1H-benzimidazole and 239 mg (1.11 mmol) of 4-bromo-2-methoxy-6-methylaniline was stirred at 120° C. for 15 hours. After cooling, the reaction mixture was neutralized by saturated aqueous sodium hydrogen carbonate, followed by addition of ethyl acetate. The resulting crystals were collected by filtration and washed with water and ethyl acetate, and suspended in hot ethyl acetate. After cooling to room temperature, the crystals were collected by filtration and washed with ethyl acetate and a 50% dimethylsulfoxide/methanol mixture to give 90 mg (54%) of the title compound.

$^1$H NMR (CDCl$_3$) δ 1.05 (3H, t, J=7.4 Hz), 2.16 (3H, s), 2.40-2.55 (2H, m), 3.09 (3H, s), 3.81 (3H, s), 5.79 (1H, br s), 6.88-6.92 (2H, m), 7.04 (1H, d, J=1.5 Hz), 7.12 (1H, t, J=7.8 Hz), 7.26-7.41 (4H, m), 7.52 (1H, d, J=7.8 Hz).

MS Calcd.: 449, 451. Found: 450, 452 (M+H).

Compounds described below were prepared in a similar method.

TABLE 5

| Example | Structure | Name | Physical Data |
|---|---|---|---|
| 62 | 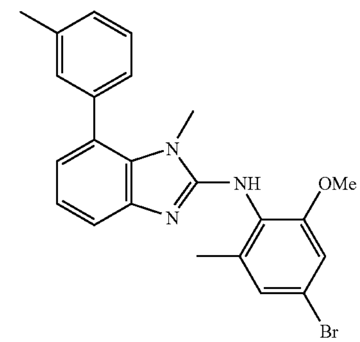 | N-(4-bromo-2-methoxy-6-methylphenyl)-1-methyl-7-(3-methylphenyl)-1H-benzimidazol-2-amine | $^1$H NMR (CDCl$_3$) δ 2.16 (3H, s), 2.43 (3H, s), 3.25 (3H, s), 3.82 (3H, s), 5.80 (1H, br s), 6.93-7.53 (9H, m). MS Calcd.: 435, 437; Found: 436, 438 (M + H). |
| 63 | 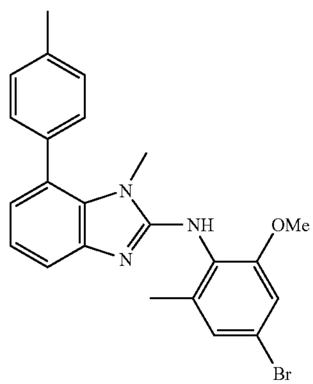 | N-(4-bromo-2-methoxy-6-methylphenyl)-1-methyl-7-(4-methylphenyl)-1H-benzimidazol-2-amine | $^1$H NMR (CDCl$_3$) δ 2.16 (3H, s), 2.44 (3H, s), 3.26 (3H, s), 3.82 (3H, s), 5.83 (1H, s), 6.92 (1H, d, J = 1.0 Hz), 6.94 (1H, d, J = 7.5 Hz), 7.04 (1H, d, J = 1.0 Hz), 7.13 (1H, t, J = 7.5 Hz), 7.25 (2H, d, J = 7.8 Hz), 7.35 (2H, d, J = 7.8 Hz), 7.50 (1H, d, J = 7.5 Hz). MS Calcd.: 435, 437; Found: 436, 438 (M + H). |

Example 64

N-(4-Chloro-2-methoxy-6-methylphenyl)-1-methyl-7-{2-[(methylamino) methyl]phenyl}-1H-benzimidazol-2-amine

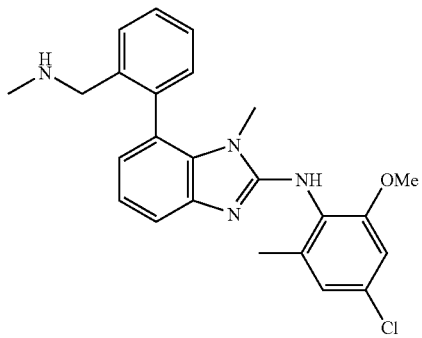

A mixture of 33 mg (0.0813 mmol) of 2-[2-[(4-chloro-2-methoxy-6-methylphenyl)amino]-1-methyl-1H-benzimidazol-7-yl]benzaldehyde, 0.033 mL (0.325 mmol) of 40% methanol solution of methyl amine and 1 mL of ethanol was refluxed for 4 hours. After cooling, 9.2 mg (0.244 mmol) of sodium borohydride was added. The mixture was stirred at room temperature for 4 hours, and 15 mg (0.407 mmol) of sodium borohydride was added. After stirring at room temperature for 15 hours, the reaction mixture was diluted with water and extracted with ethyl acetate (X2). The combined organic layer was washed with brine (X1), dried over sodium sulfate and concentrated in vacuo. The residue was purified by preparative HPLC and basic silica gel column chromatography eluting with a 50-100% ethylacetate/n-hexane gradient mixture to give 5 mg (17%) of the title compound.

$^1$H NMR (CDCl$_3$) δ 2.18 (3H, s), 2.27 (3H, s), 3.08 (3H, s), 3.57 (2H, s), 3.81 (3H, s), 6.79 (1H, s), 6.87-6.89 (2H, m), 7.10-7.15 (1H, m), 7.33-7.53 (5H, m).

Example 65

N-(4-Bromo-2-methoxy-6-methylphenyl)-1-methyl-7-(3-methyl-1H-pyrazol-1-yl)-1H-benzimidazol-2-amine

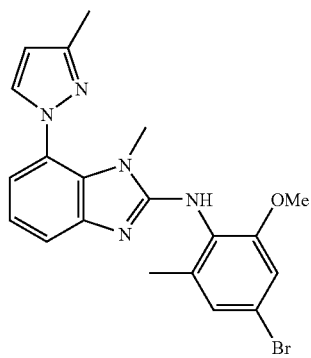

1-Methyl-7-(3-methyl-1H-pyrazol-1-yl)-1,3-dihydro-2H-benzimidazol-2-one

A suspension of 50 mg (0.220 mmol) of 7-bromo-1-methyl-1,3-dihydro-2H-benzimidazol-2-one, 0.035 mL (0.440 mmol) of 3-methylpyrazole, 42 mg (0.0220 mmol) of copper (I) iodide and 61 mg (0.440 mmol) of potassium carbonate in 1 mL of 1-methyl-2-pyrrolidinone was stirred by microwave irradiation at 190° C. for 2 hours. After cooling, the reaction mixture was diluted with water and extracted with ethyl acetate (X2). The combined organic layer was washed with brine (X1), dried over sodium sulfate and concentrated in vacuo. The residue was purified by silica gel column chromatography eluting with a 25% ethylacetate/n-hexane mixture to give 57 mg of a mixture containing the title compound.

$^1$H NMR (CDCl$_3$) δ 2.34 (3H, s), 2.98 (3H, s), 6.26 (1H, d, J=2.2 Hz), 6.97-7.18 (3H, m), 7.57 (1H, d, J=2.2 Hz), 9.60 (1H, br s).

MS Calcd.: 228. Found: 229 (M+H).

N-(4-Bromo-2-methoxy-6-methylphenyl)-1-methyl-7-(3-methyl-1H-pyrazol-1-yl)-1H-benzimidazol-2-amine A mixture of 17 mg (0.0745 mmol) of 1-methyl-7-(3-methyl-1H-pyrazol-1-yl)-1,3-dihydro-2H-benzimidazol-2-one in 0.5 mL of phosphorus oxychloride was stirred at 80° C. for 5 days. After cooling, phosphorus oxychloride was evaporated in vacuo. The residue was neutralized by 12 N aqueous sodium hydroxide. The aqueous suspension was extracted with ethyl acetate (X2). The combined organic layer was washed with water (X1) and brine (X1), dried over sodium sulfate and concentrated in vacuo. The residue was purified by preparative TLC eluting with a 30% ethylacetate/n-hexane mixture to give 2-chloro-1-methyl-7-(3-methyl-1H-pyrazol-1-yl)-1H-benzimidazole. A mixture 2-chloro-1-methyl-7-(3-methyl-1H-pyrazol-1-yl)-1H-benzimidazole obtained above, 48 mg (0.223 mmol) of 4-bromo-2-methoxy-6-methylaniline and 0.15 mL of 1-methyl-2-pyrrolidinone was stirred at 120° C. for 3 days. After cooling, the reaction mixture was neutralized by saturated aqueous sodium hydrogen carbonate. The aqueous suspension was extracted with ethyl acetate (X2). The combined organic layer was washed with water (X1) and brine (X1), dried over sodium sulfate and concentrated in vacuo. The residue was purified by preparative TLC eluting with a 75% ethylacetate/n-hexane mixture to give 5.7 mg (18%) of the title compound.

$^1$H NMR (CDCl$_3$) δ 2.17 (3H, s), 2.40 (3H, s), 3.23 (3H, s), 3.80 (3H, s), 5.87 (1H, br s), 6.28 (1H, d, J=2.1 Hz), 6.92 (1H, d, J=2.4 Hz), 7.00-7.13 (3H, m), 7.53 (1H, d, J=7.8 Hz), 7.63 (1H, d, J=2.1 Hz).

MS Calcd.: 425, 427. Found: 426, 428 (M+H).

Example 66

N-(4-Bromo-2-methoxy-6-methylphenyl)-7-(3,5-diethyl-1H-pyrazol-1-yl)-1-methyl-1H-benzimidazol-2-amine

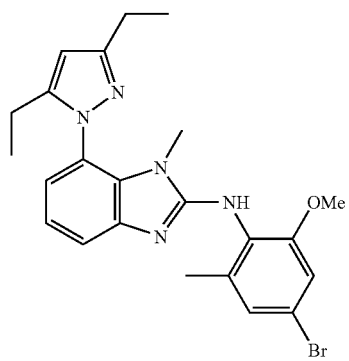

7-Hydrazino-1-methyl-1,3-dihydro-2H-benzimidazol-2-one

To a suspension of 5.0 g (30.6 mmol) of 7-amino-1-methyl-1,3-dihydro-2H-benzimidazol-2-one in 16 mL of concentrated hydrochloric acid was added 8 mL of an aqueous solution of 2.18 g (31.6 mmol) of sodium nitrite, the mixture was stirred at 0° C. for 30 minutes. Tin(II) chloride (18.0 g, 94.9 mmol) was dissolved in 10 mL of concentrated hydrochloric acid, and the solution was added to the reaction mixture at 0° C. After one hour, the mixture was alkalified by 12 N sodium hydroxide, followed by addition of ethyl acetate to the suspension. After addition of 24.6 mL of di-tert-butyl dicarbonate (107 mmol), the mixture was stirred at room temperature for 15 hours. The aqueous layer was separated and extracted with ethyl acetate (X1). The organic layer was washed with brine (X1), dried over sodium sulfate and concentrated in vacuo. The residual solids were washed with hexane to give 8.53 g of the Boc derivative of the title compound as yellow crystals. A suspension of 8.53 g (17.8 mmol) of the Boc derivative of the title compound in 100 mL of 4 N hydrogen chloride in methanol was stirred at room temperature for 12 hours. The resulting crystals were collected by filtration and washed with methanol to give 3.17 g (52%) of the title compound.

$^1$H NMR (DMSO-d$_6$) δ 3.52 (3H, s), 6.79-6.82 (2H, m), 6.98 (1H, t, J=8.0 Hz), 8.02 (1H, s), 10.03 (2H, s), 11.00 (1H, s).

7-(2,4-Diethyl-1H-pyrazol-1-yl)-1-methyl-1,3-dihydro-2H-benzimidazol-2-one

To a suspension of 211 mg (0.986 mmol) of 7-hydrazino-1-methyl-1,3-dihydro-2H-benzimidazol-2-one in 2 mL of acetic acid was added 0.13 mL (0.986 mmol) of 3,5-heptanedione, the mixture was stirred at 100° C. for 2 hours. After cooling, the reaction mixture was neutralized by saturated aqueous sodium hydrogen carbonate and extracted with ethyl acetate (X2). The combined organic layer was washed with brine (X1), dried over sodium sulfate and concentrated in vacuo. The residue was purified by silica gel column chromatography eluting with a 50-80% ethylacetate/n-hexane gradient mixture to give 221 mg (83%) of the title compound.

$^1$H NMR (CDCl$_3$) δ 1.16 (3H, t, J=7.5 Hz), 1.29 (3H, t, J=7.8 Hz), 2.35-2.53 (2H, br), 2.69 (2H, q, J=7.8 Hz), 2.85 (3H, s), 6.06 (1H, s), 7.01 (1H, dd, J=7.8, 1.5 Hz), 7.08 (1H, t, J=7.8 Hz), 7.14 (1H, dd, J=7.8, 1.5 Hz), 9.49 (1H, br s).

2-Chloro-7-(3,5-diethyl-1H-pyrazol-1-yl)-1-methyl-1H-benzimidazole

A mixture of 220 mg (0.814 mmol) of 7-(2,4-diethyl-1H-pyrazol-1-yl)-1-methyl-1,3-dihydro-2H-benzimidazol-2-one in 2 mL of phosphorus oxychloride was stirred at 85° C. for 4 hours. After cooling, phosphorus oxychloride was evaporated in vacuo. The residue was diluted with ice-cold water and neutralized by aqueous sodium hydroxide. The aqueous suspension was extracted with ethyl acetate (X2). The combined organic layer was washed with water (X1) and brine (X1), dried over sodium sulfate and concentrated in vacuo. The residue was purified by silica gel column chromatography eluting with a 25-50% ethylacetate/n-hexane gradient mixture to give 181 mg (77%) of the title compound.

¹H NMR (CDCl₃) δ 1.15 (3H, t, J=7.5 Hz), 1.30 (3H, t, J=7.5 Hz), 2.44 (2H, q, J=7.5 Hz), 2.70 (2H, q, J=7.5 Hz), 3.20 (3H, s), 6.10 (1H, s), 7.21 (1H, dd, J=7.8, 1.2 Hz), 7.30 (1H, t, J=7.8 Hz), 7.76 (1H, dd, J=7.8, 1.2 Hz).

MS Calcd.: 288, 290. Found: 289, 291 (M+H).

N-(4-Bromo-2-methoxy-6-methylphenyl)-7-(3,5-diethyl-1H-pyrazol-1-yl)-1-methyl-1H-benzimidazol-2-amine A mixture of 83 mg (0.287 mmol) of 2-chloro-7-(3,5-diethyl-1H-pyrazol-1-yl)-1-methyl-1H-benzimidazole, 186 mg (0.862 mmol) of 4-bromo-2-methoxy-6-methylaniline and 0.15 mL of 1-methyl-2-pyrrolidinone was stirred at 110° C. for 20 hours. After cooling, the reaction mixture was neutralized with saturated aqueous sodium hydrogen carbonate, followed by addition of ethyl acetate. The resulting crystals were collected by filtration and washed with water and ethyl acetate to give 112 mg (83%) of the title compound.

¹H NMR (CDCl₃) δ 1.18 (3H, t, J=7.4 Hz), 1.31 (3H, t, J=7.6 Hz), 2.17 (3H, s), 2.49 (2H, q, J=7.4 Hz), 2.72 (2H, q, J=7.6 Hz), 3.07 (3H, s), 3.81 (3H, s), 5.81 (1H, br s), 6.09 (1H, s), 6.93-7.16 (4H, m), 7.54 (1H, d, J=8.8 Hz).

MS Calcd.: 467, 469. Found: 468, 470 (M+H).

Compounds described below were prepared in a similar method.

TABLE 6

| Example | Structure | Name | Physical Data |
|---|---|---|---|
| 67 | 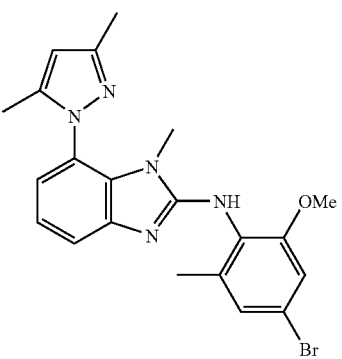 | N-(4-bromo-2-methoxy-6-methylphenyl)-7-(3,5-dimethyl-1H-pyrazol-1-yl)-1-methyl-1H-benzimidazol-2-amine | ¹H NMR (CDCl₃) δ 2.16 (3H, s), 2.18 (3H, s), 2.32 (3H, s), 3.10 (3H, s), 3.80 (3H, s), 6.04 (1H, s), 6.29 (1H, br s), 6.93-6.97 (2H, m), 7.03 (1H, s), 7.10 (1H, t, J = 7.5 Hz), 7.50 (1H, d, J = 7.5 Hz). MS Calcd.: 439, 441; Found: 440, 442 (M + H). |
| 68 | 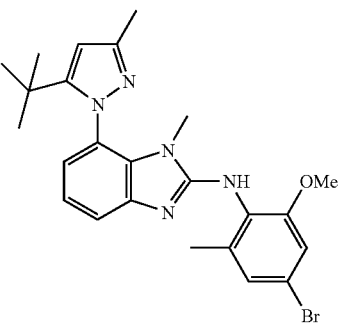 | N-(4-bromo-2-methoxy-6-methylphenyl)-7-(5-tert-butyl-3-methyl-1H-pyrazol-1-yl)-1-methyl-1H-benzimidazol-2-amine | ¹H NMR (CDCl₃) δ 1.18 (9H, s), 2.14 (3H, s), 2.31 (3H, s), 3.02 (3H, s), 3.80 (3H, s), 5.79 (1H, s), 6.06 (1H, s), 6.91 (1H, d, J = 2.1 Hz), 7.03 (1H, d, J = 2.1 Hz), 7.10 (2H, t, J = 4.5 Hz), 7.54 (1H, d, J = 4.5 Hz). MS Calcd.: 481, 483; Found: 482, 484 (M + H). |

Example 69

N-(4-Bromo-2-methoxy-6-methylphenyl)-7-(2,5-dimethyl-1H-pyrrol-1-yl)-1-methyl-1H-benzimidazol-2-amine

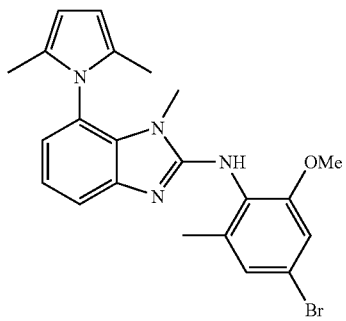

7-(2,5-Dimethyl-1H-pyrrol-1-yl)-1-methyl-1,3-dihydro-2H-benzimidazol-2-one

To a suspension of 257 mg (1.57 mmol) of 7-amino-1-methyl-1,3-dihydro-2H-benzimidazol-2-one in 2 mL of acetic acid was added 0.18 mL (1.57 mmol) of 2,5-hexanedione, the mixture was stirred at 90° C. for 1 hour. After cooling, the reaction mixture was neutralized by saturated aqueous sodium hydrogen carbonate and extracted with ethyl acetate (X2). The combined organic layer was washed with brine (X1), dried over sodium sulfate and concentrated in vacuo. The residue was purified by silica gel column chromatography eluting with a 25-50% ethylacetate/n-hexane gradient mixture to give 258 mg (68%) of the title compound.

$^1$H NMR (CDCl$_3$) δ 1.97 (6H, s), 2.79 (3H, s), 5.92 (2H, s), 6.93 (1H, dd, J=7.5, 1.5 Hz), 7.08-7.16 (2H, m), 9.45 (1H, s).

2-Chloro-7-(2,5-dimethyl-1H-pyrrol-1-yl)-1-methyl-1H-benzimidazole

A mixture of 239 mg (0.991 mmol) of 7-(2,5-dimethyl-1H-pyrrol-1-yl)-1-methyl-1,3-dihydro-2H-benzimidazol-2-one in 2 mL of phosphorus oxychloride was stirred at 85° C. for 4 hours. After cooling, phosphorus oxychloride was evaporated in vacuo. The residue was diluted with ice and neutralized by aqueous sodium hydroxide. The aqueous suspension was extracted with ethyl acetate (X2). The combined organic layer was washed with water (X1) and brine (X1), dried over sodium sulfate and concentrated in vacuo. The residue was purified by silica gel column chromatography eluting with a 10-20% ethylacetate/n-hexane gradient mixture to give 185 mg (72%) of the title compound.

$^1$H NMR (CDCl$_3$) δ 1.94 (6H, s), 3.09 (3H, s), 5.95 (2H, s), 7.15 (1H, dd, J=7.8, 1.0 Hz), 7.32 (1H, t, J=7.8 Hz), 7.75 (1H, dd, J=7.8, 1.0 Hz).

MS Calcd.: 259. Found: 260 (M+H).

N-(4-Bromo-2-methoxy-6-methylphenyl)-7-(2,5-dimethyl-1H-pyrrol-1-yl)-1-methyl-1H-benzimidazol-2-amine A mixture of 90 mg (0.347 mmol) of 2-chloro-7-(2,5-dimethyl-1H-pyrrol-1-yl)-1-methyl-1H-benzimidazole and 225 mg (1.04 mmol) of 4-bromo-2-methoxy-6-methylaniline was stirred at 110° C. for 15 hours. After cooling, the reaction mixture was neutralized by saturated aqueous sodium hydrogen carbonate and extracted with ethyl acetate (X2). The combined organic layer was washed with brine (X1), dried over sodium sulfate and concentrated in vacuo. The residue was purified by silica gel column chromatography eluting with a 60-90% ethylacetate/n-hexane gradient mixture. The desired fractions were collected and evaporated in vacuo, the residual solids were washed with diethyl ether to give 53.4 mg (35%) of the title compound.

$^1$H NMR (CDCl$_3$) δ 1.99 (6H, s), 2.19 (3H, s), 2.96 (3H, s), 3.81 (3H, s), 5.94 (2H, s), 6.92-6.96 (2H, m), 7.05 (1H, d, J=1.8 Hz), 7.15 (1H, t, J=7.5 Hz), 7.54 (1H, d, J=7.5 Hz).
MS Calcd.: 438, 440. Found: 439, 441 (M+H).

Example 70-71

Example 70 and 71 in Table 7 were prepared in the similar method described in Example 15.

TABLE 7

| Example | Structure | Name | Physical Data |
|---|---|---|---|
| 70 | 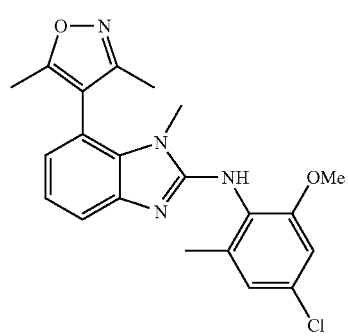 | N-(4-chloro-2-methoxy-6-methylphenyl)-7-(3,5-dimethylisoxazol-4-yl)-1-methyl-1H-benzimidazol-2-amine | $^1$H NMR (CDCl$_3$) δ: 2.17 (3H, s), 2.19 (3H, s), 2.33 (3H, s), 3.37 (3H, s), 3.82 (3H, s), 5.90 (1H, br s), 6.80-7.60 (5H, m). MS Calcd.: 396; Found: 397 (M + H). |

| Example | Structure | Name | Physical Data |
| --- | --- | --- | --- |
| 71 | 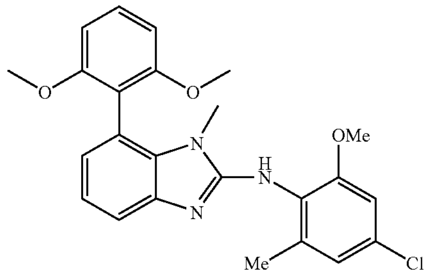 | N-(4-chloro-2-methoxy-6-methylphenyl)-7-(2,6-dimethoxyphenyl)-1-methyl-1H-benzimidazol-2-amine Trifluoroacetic acid salt | $^1$H NMR (CDCl$_3$) δ: 2.17 (3H, s), 3.07 (3H, s), 3.80 (3H, s), 3.82-4.12 (6H, m), 6.78 (1H, d, J = 2.4 Hz), 6.89 (1H, d, J = 2.4 Hz), 6.89 (1H, d, J = 7.8 Hz), 7.13 (1H, t, J = 7.8 Hz), 7.22-7.40 (3H, m), 7.51 (1H, d, J = 7.8 Hz). MS Calcd.: 437; Found: 438 (M + H). mp 288-289° C. |

Example 72

N-(4-Bromo-2-methoxy-6-methylphenyl)-1-methyl-7-(3-methyl-5-phenyl-1H-pyrazol-1-yl)-1H-benzimidazol-2-amine

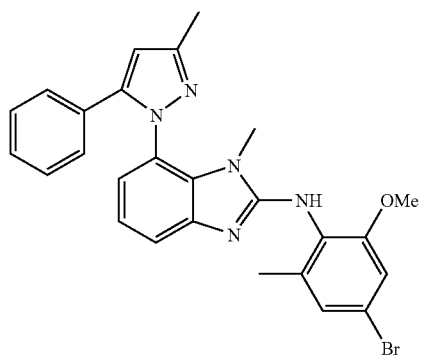

This compound was prepared in a similar manner described in Example 66.

$^1$H NMR (CDCl$_3$) δ: 2.13 (3H, s), 2.42 (3H, s), 3.19 (3H, s), 3.79 (3H, s), 5.81 (1H, br s), 6.45 (1H, s), 6.91-6.96 (2H, m), 7.03-7.08 (2H, m), 7.23 (5H, s), 7.51 (1H, d, J=8.4 Hz). MS Calcd.: 501, 503. Found: 502±504 (M+H).

Example 73

4-[1-(2-Hydroxyethyl)-2-(mesitylamino)-1H-benzimidazol-7-yl]heptan-4-ol

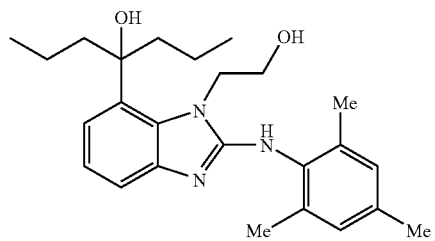

This compound was prepared in a similar manner described in Example 12.

mp 267-270° C.

$^1$H NMR (CD$_3$OD) δ: 1.24 (6H, t, J=7.5 Hz), 1.60-1.74 (4H, m), 2.16-2.40 (4H, m), 2.52 (6H, s), 2.63 (3H, s), 4.47 (2H, t, J=4.8 Hz), 5.19 (2H, t, J=4.8 Hz), 7.22 (1H, dd, J=7.8, 1.2 Hz), 7.28 (2H, s), 7.32 (1H, t, J=7.8 Hz), 7.47 (1H, dd, J=7.8, 1.2 Hz). MS Calcd.: 409. Found: 410 (M+H).

Example 74

2-[2-(Mesitylamino)-7-(1-propylbutyl)-1H-benzimidazol-1-yl]ethanol

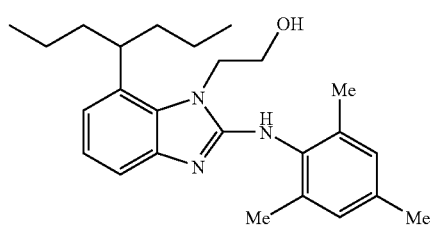

This compound was prepared in a similar manner described previously in Example 14.

$^1$H NMR (CDCl$_3$) δ: 0.92 (6H, t, J=7.5 Hz), 1.20-1.40 (4H, m), 1.77-1.88 (2H, m), 1.98-2.09 (2H, m), 2.53 (6H, s), 2.63 (3H, s), 2.87 (1H, m), 4.21 (2H, t, J=4.8 Hz), 4.45 (2H, t, J=4.8 Hz), 7.22 (1H, dd, J=7.8, 1.2 Hz), 7.27 (2H, s), 7.32 (1H, t, J=7.8 Hz), 7.46 (1H, dd, J=7.8, 1.2 Hz).

MS Calcd.: 393. Found: 394 (M+H).

Example 75

2-[2-[(4-Chloro-2-methoxy-6-methylphenyl)amino]-7-(1-hydroxy-1-propylbutyl)-1H-benzimidazol-1-yl]ethyl acetate

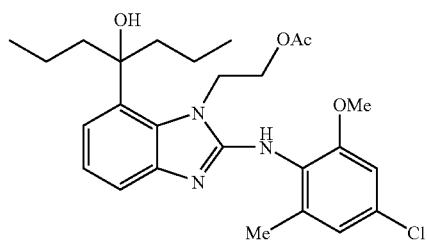

A solution of 4-[2-[(4-chloro-2-methoxy-6-methylphenyl)amino]-1-(2-hydroxyethyl)-1H-benzimidazol-7-yl]heptan-4-ol (100 mg, 0.22 mmol) in pyridine (5 mL) was treated with acetic anhydride (1 mL) and stirred at room temperature overnight. The reaction mixture was concentrated to dryness, diluted with aqueous sodium hydrogen carbonate, and extracted with ethyl acetate. The organics were dried over magnesium sulfate, filtered, and concentrated in vacuo. The residue was chromatographed on a silica gel to give 97 mg (0.20 mmol, 89%) of the title compound.

$^1$H NMR (CDCl$_3$) δ: 0.92 (6H, t, J=7.5 Hz), 1.23-1.41 (4H, m), 1.81-1.91 (2H, m), 1.98-2.09 (2H, m), 2.12 (3H, s), 2.15 (3H, s), 3.80 (3H, s), 4.56 (2H, t, J=4.8 Hz), 4.85 (2H, t, J=4.8 Hz), 6.80 (1H, d, J=2.1 Hz), 6.83 (1H, d, J=8.1 Hz), 6.88 (1H, d, J=2.1 Hz), 7.03 (1H, t, J=8.1 Hz), 7.41 (1H, d, J=8.1 Hz). MS Calcd.: 487. Found: 488 (M+H).

Example 76

2-{2-[(4-Chloro-2-methoxy-6-methylphenyl)amino]-7-[(1E)-1-propylbut-1-en-1-yl]-1H-benzimidazol-1-yl}ethyl acetate and 2-{2-[(4-Chloro-2-methoxy-6-methylphenyl)amino]-7-[(1Z)-1-propylbut-1-en-1-yl]-1H-benzimidazol-1-yl}ethyl acetate

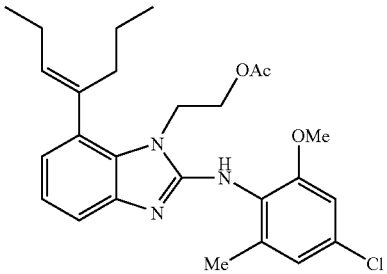

A solution of 2-[2-[(4-chloro-2-methoxy-6-methylphenyl)amino]-7-(1-hydroxy-1-propylbutyl)-1H-benzimidazol-1-yl]ethyl acetate (50 mg, 0.10 mmol) and triethylsilane (1 mL) in diethyl ether (10 mL) was stirred at room temperature for 14 h. The reaction mixture was diluted with aqueous sodium hydrogen carbonate, and extracted with ethyl acetate. The organics were dried over magnesium sulfate, filtered, and concentrated in vacuo. The residue was chromatographed on a silica gel to give 11 mg (0.023 mmol, 23%) of the title compounds.

$^1$H NMR (CDCl$_3$) δ: 0.92 (6H, t, J=7.5 Hz), 1.28-1.49 (4H, m), 1.78-1.91 (2H, m), 2.08 (3H, s), 2.17 (3H, s), 3.79 (3H, s), 4.20-4.41 (4H, m), 5.57 (0.8H, t, J=7.2 Hz), 5.65 (0.2H, t, J=7.2 Hz), 6.75 (1H, d, J=7.2 Hz), 6.80 (1H, d, J=2.1 Hz), 6.89 (1H, d, J=2.1 Hz), 7.04 (1H, t, J=7.2 Hz), 7.41 (1H, d, J=7.2 Hz). MS Calcd.: 469. Found: 470 (M+H).

Example 77

N-(4-Bromo-2-methoxy-6-methylphenyl)-4-chloro-7-(1-ethylpropyl)-1-methyl-1H-benzimidazol-2-amine

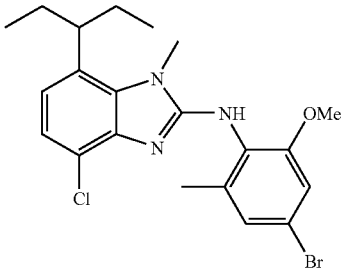

7-(1-Ethyl-1-hydroxypropyl)-1-methyl-1,3-dihydro-2H-benzimidazol-2-one

A solution of ethylmagnesium bromide (3M solution in diethyl ether; 32 mL, 96 mmol) was added dropwise to a suspension of methyl 3-methyl-2-oxo-2,3-dihydro-1H-benzimidazole-4-carboxylate (5.00 g, 24.2 mmol) in tetrahydrofuran (50 mL) at 0° C. The mixture was stirred at 40° C. overnight. The reaction was quenched with water and 1N HCl, extracted with ethyl acetate, washed with brine. The organic layer was dried over magnesium sulfate, filtered, and concentrated in vacuo. The residue was crystallized from ethanol/diethylether to afford the title compound as colorless crystals (3.39 g, 70%). mp 199-201° C.

$^1$H NMR (CDCl$_3$) δ 0.90 (t, J=7.5 Hz, 6H), 1.90-2.20 (m, 5H), 3.84 (s, 3H), 6.90-7.05 (m, 3H), 9.10-9.30 (m, 1H).

MS Calcd.: 234. Found: 235 (M+H).

7-(1-Ethylpropyl)-1-methyl-1,3-dihydro-2H-benzimidazol-2-one

A mixture of 7-(1-ethyl-1-hydroxypropyl)-1-methyl-1,3-dihydro-2H-benzimidazol-2-one (6.00 g, 25.6 mmol) and 6N HCl (20 mL) in ethanol (100 mL) was stirred at 50° C. for 3 h. The mixture was concentrated in vacuo, and the resulting residue was dissolved in ethyl acetate, washed with aqueous potassium carbonate. The organic layer was dried over magnesium sulfate, filtered, and concentrated in vacuo to give pale yellow oil, which was used in the next reaction without further purification. MS Calcd.: 216. Found: 217 (M+H). The crude material was dissolved in ethanol (150 mL). This solution was treated with 10% palladium on carbon (50% wet; 1.00 g), purged with hydrogen, and stirred under 5 atoms hydrogen for 7 h. The catalyst was removed by filtration and the filtrate was concentrated in vacuo. The residue was crystallized from ethanol/diethylether to afford the title compound as colorless crystals (3.02 g, 54%). mp 130-132° C.

$^1$H NMR (CDCl$_3$) δ 0.82 (t, J=6.6 Hz, 6H), 1.60-1.85 (m, 4H), 3.15-3.25 (m, 1H), 3.65 (s, 3H), 6.85-6.98 (m, 2H), 7.00-7.10 (m, 1H), 10.2-10.5 (m, 1H).

MS Calcd.: 218. Found: 219 (M+H).

4-Chloro-7-(1-ethylpropyl)-1-methyl-1,3-dihydro-2H-benzimidazol-2-one 2,2'-Azobisisobutyronitrile (AIBN) (94 mg, 0.57 mmol) was added to a mixture of 7-(1-ethylpropyl)-1-methyl-1,3-dihydro-2H-benzimidazol-2-one (2.90 g, 13.3 mmol) and N-chlorosuccinimide (1.95 g, 14.6 mmol) in carbon tetrachloride (250 mL). The mixture was stirred at 70° C. for 2 days. The reaction was concentrated in vacuo, extracted with ethyl acetate and washed with brine. The organic layer was dried over magnesium sulfate, filtered, and concentrated in vacuo to give residue. The residue was crystallized from ethanol/iso-propanol to afford the title compound as colorless crystals (2.28 g, 68%). mp 165-166° C.

$^1$H NMR (CDCl$_3$) δ 0.81 (t, J=7.2 Hz, 6H), 1.60-1.85 (m, 4H), 3.10-3.20 (m, 1H), 3.64 (s, 3H), 6.87 (d, J=8.7 Hz, 1H), 7.03 (d, J=8.7 Hz, 1H), 8.55 (s, 1H). MS Calcd.: 251. Found: 252 (M+H).

2,4-Dichloro-7-(1-ethylpropyl)-1-methyl-1H-benzimidazole

A mixture of 4-chloro-7-(1-ethylpropyl)-1-methyl-1,3-dihydro-2H-benzimidazol-2-one (1.17 g, 4.63 mmol) in phosphorous oxychloride (28 g) was stirred at 90° C. for 3 h. The reaction was allowed to cool to room temperature and concentrated in vacuo. The residue was dissolved in ethyl acetate, washed with aqueous sodium bicarbonate and brine. The organic layer was dried over magnesium sulfate, filtered, and concentrated in vacuo. The residue was subjected to chromatography on silica gel (n-hexane/ethyl acetate=10:1-1:1) and crystallized from ethyl acetate-hexane to afford the title compound as colorless crystals (1.03 g, 82%). mp 94-95° C.

$^1$H NMR (CDCl$_3$) δ 0.82 (t, J=7.5 Hz, 6H), 1.60-1.90 (m, 4H), 3.20-3.30 (m, 1H), 4.01 (s, 3H), 7.05 (d, J=8.4 Hz, 1H), 7.26 (d, J=8.4 Hz, 1H). MS Calcd.: 270. Found: 271 (M+H).

N-(4-Bromo-2-methoxy-6-methylphenyl)-4-chloro-7-(1-ethylpropyl)-1-methyl-1H-benzimidazol-2-amine A mixture of 2,4-dichloro-7-(1-ethylpropyl)-1-methyl-1H-benzimidazole (140 mg, 0.52 mmol), 4-bromo-2-methoxy-6-methylaniline (335 mg, 1.55 mmol) and 1-methyl-2-pyrrolidone (5 drops) was stirred at 130° C. for 2 days under nitrogen atmosphere. The mixture was dissolved in ethyl acetate/water, extracted with ethyl acetate and washed with brine. The organic layer was dried over magnesium sulfate, and concentrated to give a brown oil. The oil was subjected to chromatography on a silica gel (n-hexane/ethyl acetate=10:1-1:1) and crystallized from iso-propanol to afford the title compound as colorless crystals (115 mg, 49%). mp. 218-220° C.

$^1$H NMR (CDCl$_3$) δ 0.83 (t, J=7.2 Hz, 6H), 1.60-1.85 (m, 4H), 2.15 (s, 3H), 3.10-3.25 (m, 1H), 3.76 (s, 3H), 3.79 (s, 3H), 6.08 (s, 1H), 6.86 (d, J=8.4 Hz, 1H), 6.91 (s, 1H), 7.03 (s, 1H), 7.10-7.20 (m, 1H). MS Calcd.: 449. Found: 450 (M+H).

Examples 78-96 were prepared in the similar method described in Example 77.

Example 78

4-Chloro-N-(4-chloro-2-methoxy-6-methylphenyl)-7-(1-ethylpropyl)-1-methyl-1H-benzimidazol-2-amine

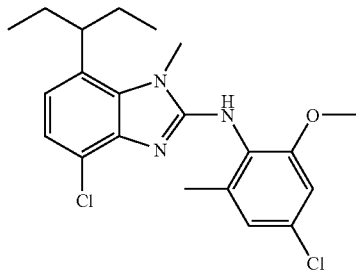

mp 219-221° C.

$^1$H NMR (CDCl$_3$) δ 0.83 (t, J=7.2 Hz, 6H), 1.60-1.85 (m, 4H), 2.16 (s, 3H), 3.10-3.20 (m, 1H), 3.75 (s, 3H), 3.79 (s, 3H), 6.07 (s, 1H), 6.77 (d, J=2.1 Hz, 1H), 6.80-6.90 (m, 2H), 7.05-7.20 (m, 1H).

MS Calcd.: 405. Found: 406 (M+H).

Example 79

4-Chloro-N-[2,6-dichloro-4-(trifluoromethoxy)phenyl]-7-(1-ethylpropyl)-1-methyl-1H-benzimidazol-2-amine

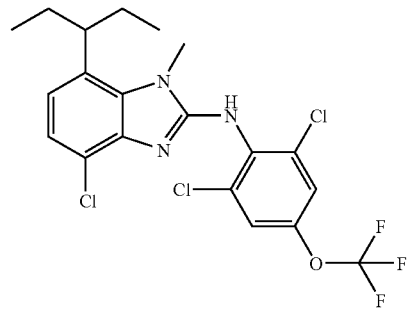

mp 147-149° C.

$^1$H NMR (CDCl$_3$) δ 0.85 (t, J=7.2 Hz, 6H), 1.60-1.85 (m, 4H), 3.10-3.20 (m, 1H), 3.87 (s, 3H), 6.75-6.90 (m, 1H), 6.98 (d, J=8.4 Hz, 1H), 7.20-7.45 (m, 2H), 8.30-8.40 (m, 1H).

MS Calcd.: 479. Found: 480 (M+H).

Example 80

4-Chloro-N-(2,4-dichlorophenyl)-7-(1-ethylpropyl)-1-methyl-1H-benzimidazol-2-amine

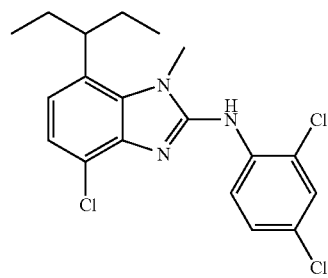

mp 130-132° C.

$^1$H NMR (CDCl$_3$) δ 0.84 (t, J=7.5 Hz, 6H), 1.60-1.85 (m, 4H), 3.15-3.25 (m, 1H), 3.84 (s, 3H), 6.72 (s, 1H), 6.96 (d, J=8.4 Hz, 1H), 7.21 (d, J=8.4 Hz, 1H), 7.29 (d, J=2.4 Hz, 1H), 7.41 (d, J=2.4 Hz, 1H), 8.09 (d, J=8.4 Hz, 1H).

MS Calcd.: 395. Found: 396 (M+H).

Example 81

4-Chloro-N-[4-chloro-2-(trifluoromethoxy)phenyl]-7-(1-ethylpropyl)-1-methyl-1H-benzimidazol-2-amine

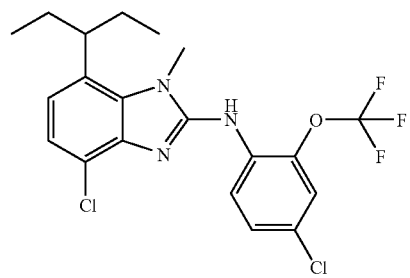

mp 126-128° C.

$^1$H NMR (CDCl$_3$) δ 0.84 (t, J=7.5 Hz, 6H), 1.60-1.85 (m, 4H), 3.15-3.30 (m, 1H), 3.87 (s, 3H), 6.81 (s, 1H), 6.98 (d, J=8.4 Hz, 1H), 7.20-7.40 (m, 3H), 8.30-8.40 (m, 1H). MS Calcd.: 445. Found: 446 (M+H).

Example 82

N-(4-Bromo-2,6-dimethylphenyl)-4-chloro-7-(1-ethylpropyl)-1-methyl-1H-benzimidazol-2-amine

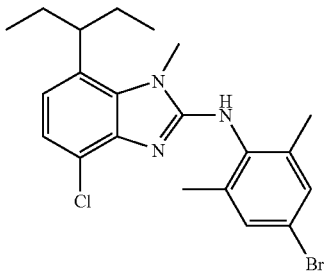

mp 247-249° C.
$^1$H NMR (CDCl$_3$) δ 0.82 (t, J=7.5 Hz, 6H), 1.55-1.80 (m, 4H), 2.17 (s, 6H), 3.00-3.20 (m, 1H), 3.40-3.65 (m, 3H), 5.90-6.00 (m, 1H), 6.70-6.90 (m, 2H), 7.00-7.20 (m, 1H), 7.20-7.30 (m, 1H). MS Calcd.: 434. Found: 435 (M+H).

Example 83

4-Chloro-N-(4-chloro-2,6-dimethylphenyl)-7-(1-ethylpropyl)-1-methyl-1H-benzimidazol-2-amine

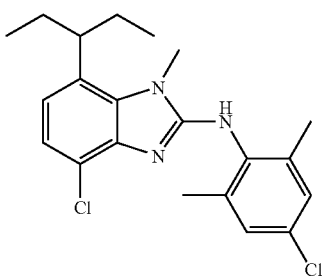

mp 247-249° C.
$^1$H NMR (CDCl$_3$) δ 0.82 (t, J=7.5 Hz, 6H), 1.55-1.80 (m, 4H), 2.18 (s, 6H), 3.00-3.20 (m, 1H), 3.40-3.65 (m, 3H), 5.90-6.00 (m, 1H), 6.70-6.90 (m, 2H), 7.05-7.20 (m, 2H). MS Calcd.: 389. Found: 390 (M+H).

Example 84

N-(2-Bromo-4-chlorophenyl)-4-chloro-7-(1-ethylpropyl)-1-methyl-1H-benzimidazol-2-amine

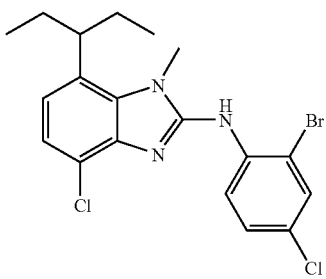

mp 136-138° C.
$^1$H NMR (CDCl$_3$) δ 0.84 (t, J=7.5 Hz, 6H), 1.60-1.85 (m, 4H), 3.15-3.25 (m, 1H), 3.84 (s, 3H), 6.81 (s, 1H), 6.96 (d, J=8.4 Hz, 1H), 7.21 (d, J=8.4 Hz, 1H), 7.32 (dd, J=8.4, 2.4 Hz, 1H), 7.56 (d, J=2.4 Hz, 1H), 8.06 (d, J=8.4 Hz, 1H). MS Calcd.: 440. Found: 441 (M+H).

Example 85

N-(4-Bromo-2-chlorophenyl)-4-chloro-7-(1-ethylpropyl)-1-methyl-1H-benzimidazol-2-amine

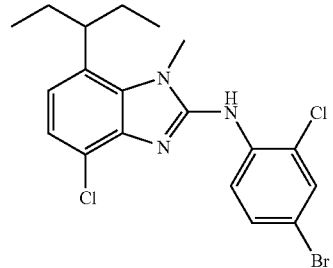

mp 127-129° C.
$^1$H NMR (CDCl$_3$) δ 0.84 (t, J=7.5 Hz, 6H), 1.60-1.85 (m, 4H), 3.15-3.25 (m, 1H), 3.85 (s, 3H), 6.80 (s, 1H), 6.96 (d, J=8.4 Hz, 1H), 7.22 (d, J=8.4 Hz, 1H), 7.42 (dd, J=8.8, 2.4 Hz, 1H), 7.55 (d, J=2.4 Hz, 1H), 8.03 (d, J=8.8 Hz, 1H). MS Calcd.: 440. Found: 441 (M+H).

Example 86

N-(2-Bromo-4-methylphenyl)-4-chloro-7-(1-ethylpropyl)-1-methyl-1H-benzimidazol-2-amine

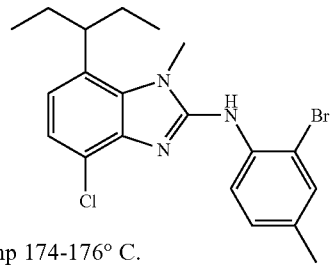

mp 174-176° C.
$^1$H NMR (CDCl$_3$) δ 0.84 (t, J=7.5 Hz, 6H), 1.60-1.85 (m, 4H), 2.30 (s, 3H), 3.15-3.25 (m, 1H), 3.80 (s, 3H), 6.74 (s, 1H), 6.94 (d, J=8.4 Hz, 1H), 7.10-7.15 (m, 1H), 7.20 (d, J=8.4 Hz, 1H), 7.38 (d, J=1.2 Hz, 1H)-7.77 (d, J=8.4 Hz, 1H). MS Calcd.: 420. Found: 421 (M+H).

Example 87

4-Chloro-N-[2-chloro-4-(trifluoromethoxy)phenyl]-7-(1-ethylpropyl)-1-methyl-1H-benzimidazol-2-amine

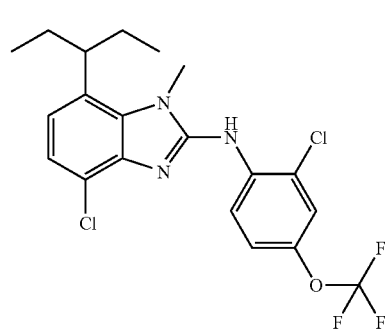

mp 122-123° C.
$^1$H NMR (CDCl$_3$) δ 0.84 (t, J=7.5 Hz, 6H), 1.60-1.85 (m, 4H), 3.15-3.25 (m, 1H), 3.87 (s, 3H), 6.81 (s, 1H), 6.96 (d, J=8.4 Hz, 1H), 7.21 (d, J=8.4 Hz, 2H), 7.31 (s, 1H), 8.21 (d, J=8.4 Hz, 1H). MS Calcd.: 445. Found: 446 (M+H).

Example 88

N[5]-[4-Chloro-7-(1-ethylpropyl)-1-methyl-1H-benzimidazol-2-yl]-N[2],N[2],4-trimethylpyridine-2,5-diamine

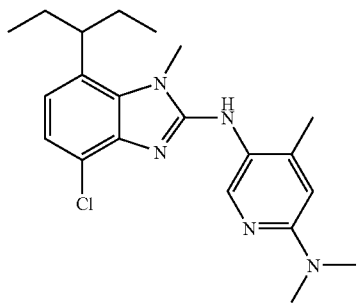

mp 224-226° C.
$^1$H NMR (CDCl$_3$) δ 0.82 (t, J=7.2 Hz, 6H), 1.60-1.85 (m, 4H), 2.26 (s, 3H), 3.00-3.20 (m, 1H), 3.07 (s, 6H), 3.59 (s, 3H), 5.90 (s, 1H), 6.41 (s, 1H), 6.87 (d, J=8.4 Hz, 1H), 7.15 (d, J=8.4 Hz, 1H), 7.91 (s, 1H). MS Calcd.: 385. Found: 386 (M+H).

Example 89

N-(4-Bromo-2-methoxy-6-methylphenyl)-4-chloro-1-methyl-7-(1-propylbutyl)-1H-benzimidazol-2-amine

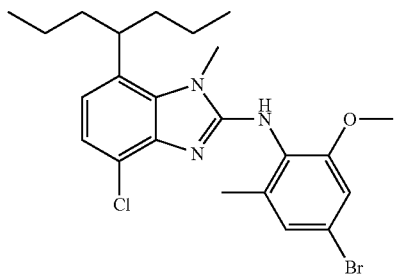

mp 210-211° C.
$^1$H NMR (CDCl$_3$) δ 0.86 (t, J=7.5 Hz, 6H), 1.15-1.35 (m, 4H), 1.60-1.80 (m, 4H), 2.15 (s, 3H), 3.25-3.40 (m, 1H), 3.75 (s, 3H), 3.79 (s, 3H), 6.07 (s, 1H), 6.85-6.95 (m, 2H), 7.00-7.20 (m, 2H). MS Calcd.: 477. Found: 478 (M+H).

Example 90

4-Chloro-N-(4-chloro-2-methoxy-6-methylphenyl)-1-methyl-7-(1-propylbutyl)-1H-benzimidazol-2-amine

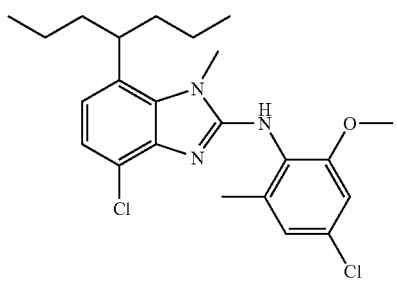

mp 204-206° C.

$^1$H NMR (CDCl$_3$) δ 0.86 (t, J=7.2 Hz, 6H), 1.10-1.30 (m, 4H), 1.55-1.75 (m, 4H), 2.15 (s, 3H), 3.25-3.40 (m, 1H), 3.75 (s, 3H), 3.79 (s, 3H), 6.08 (s, 1H), 6.77 (d, J=2.1 Hz, 1H), 6.80-6.90 (m, 2H), 7.10 (d, J=8.4 Hz, 1H). MS Calcd.: 433. Found: 434 (M+H).

Example 91

4-Chloro-N-(2,4-dichlorophenyl)-1-methyl-7-(1-propylbutyl)-1H-benzimidazol-2-amine

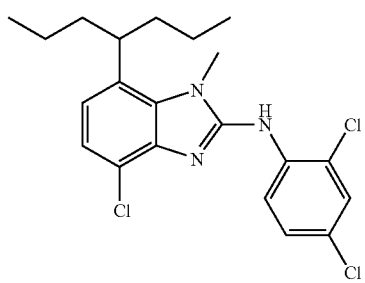

mp 146-148° C.
$^1$H NMR (CDCl$_3$) δ 0.86 (t, J=7.2 Hz, 6H), 1.10-1.30 (m, 4H), 1.55-1.80 (m, 4H), 3.30-3.45 (m, 1H), 3.84 (s, 3H), 6.79 (s, 1H), 6.97 (d, J=8.1 Hz, 1H), 7.21 (d, J=8.1 Hz, 1H), 7.29 (d, J=2.4 Hz, 1H), 7.41 (d, J=2.4 Hz, 1H), 8.09 (d, J=8.4 Hz, 1H). MS Calcd.: 423. Found: 424 (M+H).

Example 92

N-(2-Bromo-4-chlorophenyl)-4-chloro-1-methyl-7-(1-propylbutyl)-1H-benzimidazol-2-amine

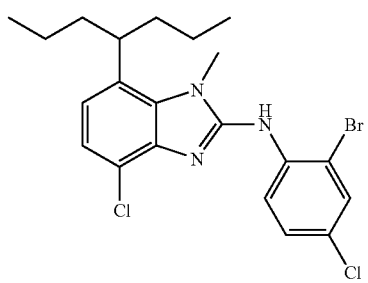

mp 145-147° C.
$^1$H NMR (CDCl$_3$) δ 0.86 (t, J=7.5 Hz, 6H), 1.10-1.30 (m, 4H), 1.55-1.80 (m, 4H), 3.30-3.45 (m, 1H), 3.84 (s, 3H), 6.80 (s, 1H), 7.00 (d, J=8.1 Hz, 1H), 7.20 (d, J=8.1 Hz, 1H), 7.31 (dd, J=8.7, 2.4 Hz, 1H), 7.55 (d, J=2.4 Hz, 1H), 8.04 (d, J=8.7 Hz, 1H). MS Calcd.: 469. Found: 470 (M+H).

Example 93

N-(4-Bromo-2-chlorophenyl)-4-chloro-1-methyl-7-(1-propylbutyl)-1H-benzimidazol-2-amine

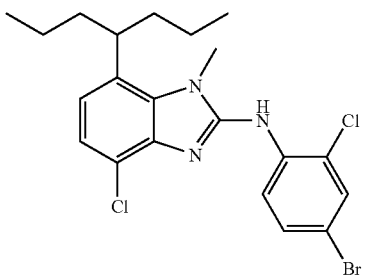

mp 145-147° C.
$^1$H NMR (CDCl$_3$) δ 0.86 (t, J=7.5 Hz, 6H), 1.10-1.30 (m, 4H), 1.55-1.80 (m, 4H), 3.30-3.45 (m, 1H), 3.84 (s, 3H), 6.79 (s, 1H), 7.00 (d, J=8.1 Hz, 1H), 7.21 (d, J=8.1 Hz, 1H), 7.41 (dd, J=9.0, 2.4 Hz, 1H), 7.54 (d, J=2.4 Hz, 1H), 8.03 (d, J=9.0 Hz, 1H). MS Calcd.: 469. Found: 470 (M+H).

Example 94

4-Chloro-N-[4-chloro-2-(trifluoromethoxy)phenyl]-1-methyl-7-(1-propylbutyl)-1H-benzimidazol-2-amine

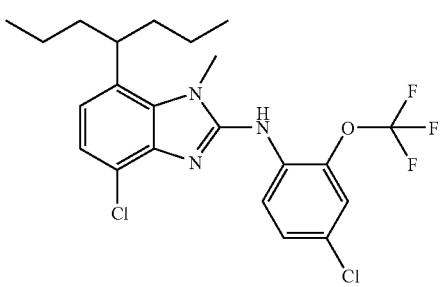

mp 130-132° C.
$^1$H NMR (CDCl$_3$) δ 0.86 (t, J=7.5 Hz, 6H), 1.10-1.30 (m, 4H), 1.55-1.80 (m, 4H), 3.30-3.40 (m, 1H), 3.81 (s, 3H), 6.56 (s, 1H), 6.97 (d, J=8.1 Hz, 1H), 7.20 (d, J=8.1 Hz, 1H), 7.25-7.30 (m, 2H), 8.00-8.20 (m, 1H). MS Calcd.: 473. Found: 474 (M+H).

Example 95

4-Chloro-N-[2-chloro-4-(trifluoromethyl)phenyl]-7-(1-ethylpropyl)-1-methyl-1H-benzimidazol-2-amine

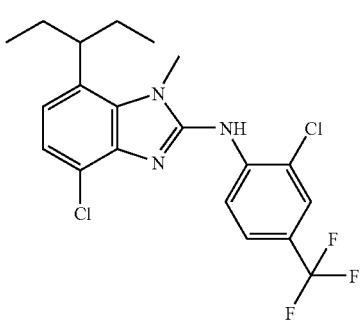

mp 128-129° C.

$^1$H NMR (CDCl$_3$) δ 0.84 (6H, t, J=7.4 Hz) 1.65-1.88 (4H, m) 3.14-3.27 (1H, m) 3.88 (3H, s) 6.94-7.04 (2H, m) 7.20-7.28 (1H, m) 7.55 (1H, dd, J=8.8, 1.9 Hz) 7.66 (1H, d, J=1.9 Hz) 8.20 (1H, d, J=9.9 Hz)
MS Calcd.: 429. Found: 430 (M+H).

Example 96

4-Bromo-N-(4-chloro-2-methoxy-6-methylphenyl)-7-(1-ethylpropyl)-1-methyl-1H-benzimidazol-2-amine

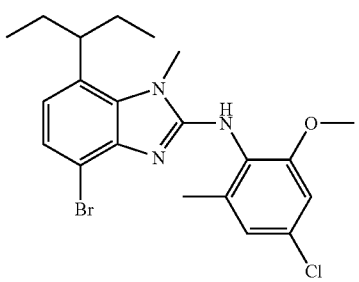

mp 198-199° C.
$^1$H NMR (CDCl$_3$) δ 0.83 (t, J=7.2 Hz, 6H), 1.60-1.80 (m, 4H), 2.17 (s, 3H), 3.15 (m, 1H), 3.72 (s, 3H), 3.78 (s, 3H), 6.11 (bs, 1H), 6.77 (s, 1H), 6.81 (d, J=8.4 Hz, 1H), 6.87 (s, 1H), 7.20-7.30 (m, 1H).
MS Calcd.: 449. Found: 450 (M+H).

Example 97

4-Chloro-2-(2,4-dichloro-6-methylphenoxy)-7-(1-ethylpropyl)-1-methyl-1H-benzimidazole

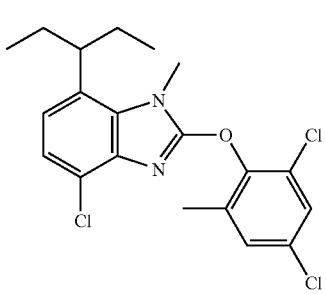

A solution of 2,4-dichloro-7-(1-ethylpropyl)-1-methyl-1H-benzimidazole (5.5 g, 20.2 mmol), 2,4-dichloro-6-methylphenol (10 g, 56.5 mmol) and potassium carbonate (8.4 g, 60.8 mmol) in N,N-dimethylformamide (55 mL) was heated at 100° C. for 9 h. To the mixture was added 2,4-dichloro-6-methylphenol (5 g, 28.3 mmol) and potassium carbonate (4.2 g, 30.4 mmol) and heated at 100° C. for 16 h. Additional 2,4-dichloro-6-methylphenol (5 g, 28.3 mmol) and potassium carbonate (4.2 g, 30.4 mmol) were added and heated at 100° C. for 9 h. After cooling, the mixture was diluted with water and extracted with ethyl acetate. The extract was washed with brine, dried over magnesium sulfate, filtered and concentrated in vacuo. The residue was purified by column chromatography on NH silica gel eluting with a 12.5% ethyl acetate/n-hexane. The resulting solids were recrystallized from a 10% ethyl acetate/n-hexane to give 5.3 g (64%) of the title compound as a colorless crystal.

mp 155-157° C.

$^1$H NMR (CDCl$_3$) δ 0.86 (t, J=7.2 Hz, 6H), 1.64-1.86 (m, 4H), 2.31 (s, 3H), 3.17-3.28 (m, 1H), 3.99 (s, 3H), 6.93 (d, J=8.4 Hz, 1H), 7.14 (d, J=8.4 Hz, 1H), 7.20 (d, J=2.4 Hz, 1H), 7.31 (d, J=2.4 Hz, 1H).

MS Calcd.: 410. Found: 411 (M+H).

Examples 98-99 were prepared in the similar method described in Example 97.

Examples 98

4-Chloro-2-(2,4-dichlorophenoxy)-7-(1-ethylpropyl)-1-methyl-1H-benzimidazole

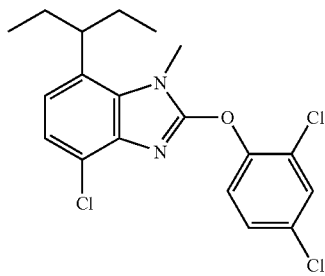

mp 87-89° C.

$^1$H NMR (CDCl$_3$) δ 0.84 (6H, t, J=7.3 Hz) 1.63-1.88 (4H, m) 3.16-3.28 (1H, m) 3.97 (3H, s) 6.96 (1H, d, J=8.2 Hz) 7.18 (1H, d, J=8.2 Hz) 7.32 (1H, dd, J=8.8, 2.5 Hz) 7.47 (1H, d, J=2.5 Hz) 7.74 (1H, d, J=8.8 Hz).

MS Calcd.: 396. Found: 397 (M+H).

Examples 99

4-Chloro-7-(1-ethylpropyl)-2-(mesityloxy)-1-methyl-1H-benzimidazole

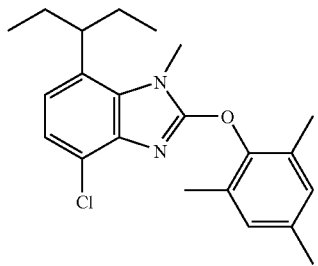

mp 137-139° C.

$^1$H NMR (CDCl$_3$) δ 0.87 (6H, t, J=7.4 Hz) 1.65-1.87 (4H, m) 2.17 (6H, s) 2.30 (3H, s) 3.17-3.29 (1H, m) 3.97 (3H, s) 6.87-6.95 (3H, m) 7.12 (1H, d, J=8.2 Hz).

MS Calcd.: 370. Found: 371 (M+H).

Examples 100

N-(4-Chloro-2-methoxy-6-methylphenyl)-7-(1-ethylpropyl)-4-methoxy-1-methyl-1H-benzimidazol-2-amine

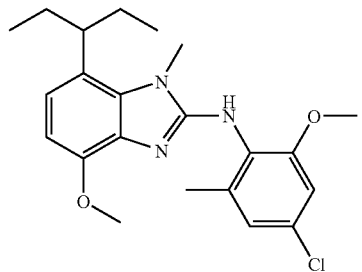

7-(1-Ethylpropyl)-4-methoxy-1-methyl-1,3-dihydro-2H-benzimidazol-2-one

A solution of 4-bromo-7-(1-ethylpropyl)-1-methyl-1,3-dihydro-2H-benzimidazol-2-one (250 mg, 0.841 mmol), anhydrous cuprus iodide (192 mg, 1.01 mmol) and 28% sodium methoxide in methanol (5.2 mL) in N,N-dimethylformamide (5 mL) was heated at 100° C. for 1 h. After cooling, the mixture was diluted with water and extracted with ethyl acetate. The organics were dried over magnesium sulfate, filtered and concentrated in vacuo to give the title compound (190 mg, 0.765 mmol, 91%).

$^1$H NMR (CDCl$_3$) δ 0.81 (6H, t, J=7.5 Hz), 1.65-1.80 (4H, m), 3.05-3.15 (1H, m), 3.63 (3H, s), 3.90 (3H, s), 6.63 (1H, d, J=8.4 Hz), 6.85 (1H, d, J=8.4 Hz), 8.39 (1H, br).

MS Calcd.: 248. Found: 249 (M+H).

2-Chloro-7-(1-ethylpropyl)-4-methoxy-1-methyl-1H-benzimidazole

A mixture of 7-(1-ethylpropyl)-4-methoxy-1-methyl-1,3-dihydro-2H-benzimidazol-2-one (190 mg, 0.765 mmol) in phosphorous oxychloride (2.14 mL) was stirred at 110° C. for 6 h. The reaction was allowed to cool to room temperature and concentrated in vacuo. The residue was dissolved in ethyl acetate and washed with aqueous sodium bicarbonate and brine. The organic layer was dried over magnesium sulfate, filtered, and concentrated in vacuo. The residue was purified by column chromatography on silica gel (n-hexane/ethyl acetate 10:1-1:1) and crystallized from ethyl acetate/n-hexane to afford the title compound as colorless crystals (123 mg, 60%).

MS Calcd.: 266. Found: 267 (M+H).

N-(4-Chloro-2-methoxy-6-methylphenyl)-7-(1-ethylpropyl)-4-methoxy-1-methyl-1H-benzimidazol-2-amine A mixture of 2-chloro-7-(1-ethylpropyl)-4-methoxy-1-methyl-1H-benzimidazole (120 mg, 0.450 mmol), 4-chloro-2-methoxy-6-methylaniline (231 mg, 1.35 mmol) and 1-methyl-2-pyrrolidone (0.5 mL) was stirred at 130° C. for 2 days under nitrogen atmosphere. The mixture was diluted with water, extracted with ethyl acetate and washed with brine.

95

The organic layer was dried over magnesium sulfate, and concentrated in vacuo. The residue was purified by column chromatography on silica gel (n-hexane/ethyl acetate=10:1-1:1) and crystallized from iso-propanol to afford the title compound as colorless crystals (100 mg, 55%).

mp 188-189° C.

$^1$H NMR (CDCl$_3$) δ 0.85 (t, J=7.2 Hz, 6H), 1.60-1.80 (m, 4H), 2.08 (s, 3H), 3.10-3.20 (m, 1H), 3.79 (s, 3H), 3.82 (s, 3H), 3.90 (s, 3H), 5.89 (m, 1H), 6.61 (d, J=8.7 Hz, 1H), 6.75 (d, J=1.8 Hz, 1H), 6.83 (d, J=1.8 Hz, 1H), 6.86 (d, J=8.7 Hz, 1H). MS Calcd.: 401. Found: 402 (M+H).

Examples 101

N-(4-Chloro-2-methoxy-6-methylphenyl)-7-(1-ethylpropyl)-1,4-dimethyl-1H-benzimidazol-2-amine

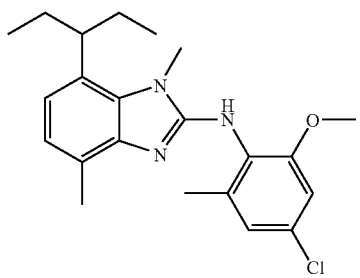

7-(1-Ethylpropyl)-1,4-dimethyl-1,3-dihydro-2H-benzimidazol-2-one

A solution of 4-bromo-7-(1-ethylpropyl)-1-methyl-1,3-dihydro-2H-benzimidazol-2-one (250 mg, 0.84 mmol), tetrakis(triphenylphosphine)palladium (194 mg, 0.168 mmol), tetramethyltin (1.16 mL, 8.4 mmol) in hexamethylphosphoric triamide (5 mL) was refluxed for 18 h. After cooling, the mixture was diluted with water and extracted with dichloromethane. The organics were dried over magnesium sulfate, filtered and concentrated in vacuo. The residue was purified by column chromatography on a silica gel (n-hexane/ethyl acetate=90:10-50:50) to give the title compound (111 mg, 0.48 mmol, 57%).

$^1$H NMR (CDCl$_3$) δ 0.82 (6H, t, J=7.5 Hz), 1.55-1.80 (4H, m), 2.38 (3H, s), 3.10-3.20 (1H, m), 3.65 (3H, s), 6.84 (1H, d, J=8.4 Hz), 6.87 (1H, d, J=8.4 Hz), 10.15 (1H, br).

MS Calcd.: 232. Found: 233 (M+H).

2-Chloro-7-(1-ethylpropyl)-1,4-dimethyl-1H-benzimidazole

A mixture of 7-(1-ethylpropyl)-1,4-dimethyl-1,3-dihydro-2H-benzimidazol-2-one (105 mg, 0.452 mmol) in phosphorous oxychloride (1.23 mL) was stirred at 110° C. for 3 h. The reaction was allowed to cool to room temperature and concentrated in vacuo. The residue was dissolved in ethyl acetate, washed with aqueous sodium bicarbonate and brine. The organic layer was dried over magnesium sulfate, filtered, and concentrated in vacuo. The residue was purified by column chromatography on silica gel (n-hexane/ethyl acetate=10:1-1:1) and crystallized from ethyl acetate/n-hexane to afford the title compound as colorless crystals (100 mg, 88%).

MS Calcd.: 250. Found: 251 (M+H).

96

N-(4-Chloro-2-methoxy-6-methylphenyl)-7-(1-ethylpropyl)-1,4-dimethyl-1H-benzimidazol-2-amine A mixture of 2-chloro-7-(1-ethylpropyl)-1,4-dimethyl-1H-benzimidazole (100 mg, 0.399 mmol), 4-chloro-2-methoxy-6-methylaniline (205 mg, 1.20 mmol) and 1-methyl-2-pyrrolidone (0.2 mL) was stirred at 120° C. for 2 days under nitrogen atmosphere. The mixture was diluted with water and extracted with ethyl acetate, washed with brine. The organic layer was dried over magnesium sulfate, and concentrated in vacuo. The residue was purified by column chromatography on silica gel (n-hexane:ethyl acetate=10:1-1:1) and crystallized from iso-propanol to afford the title compound as colorless crystals (53 mg, 34%).

mp 201-202° C.

$^1$H NMR (CDCl$_3$) δ 0.85 (t, J=7.2 Hz, 6H), 1.60-1.80 (m, 4H), 2.11 (s, 3H), 2.45 (s, 3H), 3.10-3.20 (m, 1H), 3.78 (s, 3H), 3.81 (s, 3H), 6.00 (m, 1H), 6.78 (d, J=2.1 Hz, 1H), 6.80-6.95 (m, 3H). MS Calcd.: 385. Found: 386 (M+H).

Example 102

Isopropyl[4-chloro-2-[(4-chloro-2-methoxy-6-methylphenyl)amino]-7-(1-ethylpropyl)-1H-benzimidazol-1-yl]acetate

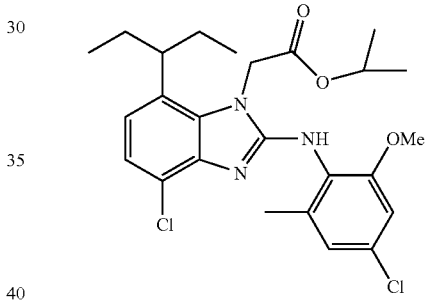

Methyl 2,3-diaminobenzoate

To a suspension of methyl 2-amino-3-nitrobenzoate (15 g, 76.5 mmol) in methanol (800 mL) was added 10% palladium on carbon (50% wet; 6.5 g), and the mixture was stirred at room temperature for 20 hours under hydrogen atmosphere. The catalyst was removed by filtration, and the filtrate was concentrated in vacuo. The residual solid was crystallized from diisopropyl ether-hexane to give 11.57 g (69.6 mmol, 91.0%) of the title compound as a dark yellow needle.

$^1$H NMR (CDCl$_3$) δ: 3.33 (2H, br s), 3.07 (3H, s), 5.56 (2H, br s), 6.60 (1H, dd, J=8.1, 7.5 Hz), 6.85 (1H, dd, J=7.5, 1.5 Hz), 7.47 (1H, dd, J=8.1, 1.5 Hz).

MS Calcd.: 166. Found: 167 (M+H).

Methyl 2-oxo-2,3-dihydro-1H-benzimidazole-4-carboxylate

To a solution of methyl 2,3-diaminobenzoate (10.5 g, 63.2 mmol) in tetrahydrofuran (100 mL) was added N,N'carbonyldiimidazole (10.2 g, 63.2 mmol), and the mixture was stirred at room temperature for 60 hours. The resulting solid was collected by filtration and washed with ethyl acetate to give 10.2 g (53.1 mmol, 84.0%) of the title compound as a colorless crystal.

¹H NMR (DMSO-d₆) δ: 3.87 (3H, s), 7.03 (1H, dd, J=8.1, 7.5 Hz), 6.85 (1H, dd, J=7.5, 1.2 Hz), 7.48 (1H, dd, J=8.1, 1.2 Hz), 10.82 (2H, br s).
MS Calcd.: 192. Found: 193 (M+H).

4-(1-Ethyl-1-hydroxypropyl)-1,3-dihydro-2H-benzimidazol-2-one

To a suspension of methyl 2-oxo-2,3-dihydro-1H-benzimidazole-4-carboxylate (513 mg, 2.67 mmol) in tetrahydrofuran (5 mL) was added 3M solution of ethyl magnesium bromide in diethyl ether (3.6 ml, 10.7 mmol), and the mixture was stirred at room temperature for 1 hour and refluxed for 20 hours. Addition of 3M solution of ethyl magnesium bromide in diethyl ether (5.3 mL, 16.0 mmol) was followed by refluxing for 30 hours. The reaction mixture was acidified with 6 N hydrochloric acid and extracted with ethyl acetate (X2). The combined organic layer was washed with brine (X1), dried over sodium sulfate and concentrated in vacuo. The resulting solid was washed with diisopropyl ether to give 440 mg (2.00 mmol, 74.8%) of the title compound.
¹H NMR (CDCl₃) δ: 0.83 (6H, t, J=7.5 Hz), 1.76-1.98 (4H, m), 2.19 (1H, br s), 6.72 (1H, d, J=7.8 Hz), 6.92-7.02 (2H, m), 9.16 (1H, br s), 9.44 (1H, br s).
MS Calcd.: 220. Found: 203 (M−H₂O+H).

4-[(1E)-1-Ethylprop-1-en-1-yl]-1,3-dihydro-2H-benzimidazol-2-one and 4-[(1Z)-1-Ethylprop-1-en-1-yl]-1,3-dihydro-2H-benzimidazol-2-one To a solution of 4-(1-ethyl-1-hydroxypropyl)-1,3-dihydro-2H-benzimidazol-2-one (410 mg, 1.86 mmol) in ethanol (6 mL) was added 6N hydrochloric acid (1.2 mL), and the mixture was stirred at 75° C. for 2 hours. After cooling, the reaction mixture was diluted with saturated aqueous sodium hydrogen carbonate and extracted with ethyl acetate (X2). The combined organic layer was washed with water (X1) and brine (X1), dried over sodium sulfate, passed through silica gel and concentrated in vacuo to give 364 mg (1.80 mmol, 96.8%) of the title compound as a pale yellow solid.
¹H NMR (CDCl₃) δ: 0.95 (3H, t, J=7.5 Hz), 1.49 (0.75H, d, J=6.9 Hz), 1.84 (2.25H, d, J=6.9 Hz), 2.36 (0.5H, q, J=7.5 Hz), 2.50 (1.5H, q, J=7.5 Hz), 5.62-5.75 (1H, m), 6.82-7.08 (3H, m), 8.29 (0.25H, s), 8.42 (0.75H, s), 9.30 (1H, s).
MS Calcd.: 202. Found: 203 (M+H).

4-(1-Ethylpropyl)-1,3-dihydro-2H-benzimidazol-2-one

To a suspension of a mixture of 4-[(1E)-1-ethylprop-1-en-1-yl]-1,3-dihydro-2H-benzimidazol-2-one and 4-[(1Z)-1-ethylprop-1-en-1-yl]-1,3-dihydro-2H-benzimidazol-2-one (329 mg, 1.63 mmol) and ammonium formate (820 mg, 13.0 mmol) in ethanol (3 mL) was added 10% palladium on carbon (50% wet; 120 mg), and the mixture was stirred at room temperature for 15 hours. The catalyst was removed by filtration, and the filtrate was concentrated in vacuo. The residue was diluted with water and extracted with ethyl acetate (X1). The organic layer was washed with brine (X1), dried over sodium sulfate and concentrated in vacuo to give 354 mg (>99%) of the title compound as a colorless solid.
¹H NMR (CDCl₃) δ: 0.80 (6H, t, J=7.2 Hz), 1.57-1.82 (4H, m), 2.50-2.62 (1H, m), 6.88 (1H, d, J=7.8 Hz), 6.92 (1H, d, J=7.8 Hz), 7.03 (1H, t, J=7.8 Hz), 9.44 (1H, s), 9.54 (1H, s).
MS Calcd.: 204. Found: 205 (M+H).

tert-Butyl 4-(1-ethylpropyl)-2-oxo-2,3-dihydro-1H-benzimidazole-1-carboxylate

To a suspension of 4-(1-ethylpropyl)-1,3-dihydro-2H-benzimidazol-2-one (7.25 g, 35.5 mmol) in 1,2-dichloroethane (5 mL) was added N,N-dimethylaminopyridine (4.34 g, 35.5 mmol) and di-tert-butyl dicarbonate (8.16 ml, 35.5 mmol) at 0° C., and the mixture was stirred at 0° C. for 30 minutes. The reaction mixture was diluted with water and extracted with dichloromethane (X2). The combined organic layer was washed with brine (X2), dried over sodium sulfate and concentrated in vacuo. The residue was purified by silica gel column chromatography eluting with a 5-40% ethyl acetate/hexane gradient mixture to give 7.87 g (25.9 mmol, 72.8%) of the title compound as a colorless solid.
¹H NMR (CDCl₃) δ: 0.79 (6H, t, J=7.4 Hz), 1.55-1.83 (4H, m), 1.6.8 (9H, s), 2.40-2.60 (1H, m), 6.97 (1H, d, J=8.0 Hz), 7.09 (1H, t, J=8.0 Hz), 7.65 (1H, d, J=8.0 Hz), 8.93 (1H, s).

tert-Butyl 4-(1-ethylpropyl)-3-(2-isopropoxy-2-oxoethyl)-2-oxo-2,3-dihydro-1H-benzimidazole-1-carboxylate To a suspension of tert-butyl 4-(1-ethylpropyl)-2-oxo-2,3-dihydro-1H-benzimidazole-1-carboxylate (7.70 g, 25.3 mmol) in N,N-dimethylformamide (50 mL) was added potassium carbonate (3.84 g, 27.8 mmol) and isopropyl bromoacetate (3.60 ml, 27.8 mmol), and the mixture was stirred at room temperature for 5 hours. The reaction mixture was diluted with water and extracted with ethyl acetate (X2). The combined organic layer was washed with aqueous sodium chloride (X2) and brine (X1), dried over sodium sulfate and concentrated in vacuo. The residue was purified by silica gel column, chromatography eluting with a 5-20% ethyl acetate/hexane gradient mixture to give 8.95 g (22.1 mmol, 87.5%) of the title compound as a colorless oil.
¹H NMR (CDCl₃) δ: 0.82 (6H, t, J=7.5 Hz), 1.26 (6H, d, J=6.3 Hz), 1.53-1.76 (4H, m), 1.67 (9H, s), 2.57-2.68 (1H, m), 4.80 (2H, s), 5.02-5.14 (1H, m), 7.03 (1H, dd, J=8.1, 1.5 Hz), 7.11 (1H, t, J=8.1 Hz), 7.79 (1H, dd, J=8.1, 1.5 Hz).

Isopropyl[7-(1-ethylpropyl)-2-oxo-2,3-dihydro-1H-benzimidazol-1-yl]acetate

To a solution of tert-butyl 4-(1-ethylpropyl)-3-(2-isopropoxy-2-oxoethyl)-2-oxo-2,3-dihydro-1H-benzimidazole-1-carboxylate (8.95 g, 22.1 mmol) in ethyl acetate (10 ml) was added a 4N solution of hydrogen chloride in ethyl acetate (20 ml), and the mixture was stirred at room temperature for 1 hour. The reaction mixture was diluted with saturated aqueous sodium hydrogen carbonate and extracted with ethyl acetate (X2). The combined organic layer was washed with brine (X1), dried over sodium sulfate and concentrated in vacuo. The residue was purified by silica gel column chromatography eluting with a 5-20% ethyl acetate/hexane gradient mixture. The residual solid was washed with hexane to give 5.76 g (18.9 mmol, 85.6%) of the title compound as a colorless solid.
¹H NMR (CDCl₃) δ: 0.81 (6H, t, J=7.5 Hz), 1.26 (6H, d, J=6.3 Hz), 1.55-1.79 (4H, m), 2.62-2.73 (1H, m), 4.82 (2H, s), 5.05-5.15 (1H, m), 6.90-6.94 (2H, m), 7.04 (1H, d, J=7.8 Hz), 9.12 (1H, s).
MS Calcd.: 304. Found: 305 (M+H).

Isopropyl[4-chloro-7-(1-ethylpropyl)-2-oxo-2,3-dihydro-1H-benzimidazol-1-yl]acetate To a solution of isopropyl[7-(1-ethylpropyl)-2-oxo-2,3-dihydro-1H-benzimidazol-1-yl]acetate (5.29 g, 17.4 mmol) in carbon tetrachloride (350 mL) was added N-chlorosuccinimide (2.55 g, 19.1 mmol) and 2,2'-azobisisobutyronitrile (86 mg, 0.522 mmol), and the mixture was stirred at 70° C. for 3 days. The reaction mixture was diluted with saturated aqueous sodium hydrogen carbonate and extracted with dichloromethane (X2). The combined organic layer was washed with water (X1) and brine (X1), dried over sodium sulfate and concentrated in vacuo. The residue was purified by silica gel column chromatography eluting with a 10-50% ethyl acetate/hexane gradient mixture to give 3.83 g (11.3 mmol, 65.0%) of the title compound as a colorless solid.

$^1$H NMR (CDCl$_3$) δ: 0.83 (6H, t, J=7.5 Hz), 1.27 (6H, d, J=6.3 Hz), 1.57-1.78 (4H, m), 2.59-2.68 (1H, m), 4.80 (2H, s), 5.02-5.14 (1H, m), 6.86 (1H, d, J=8.7 Hz), 7.04 (1H, d, J=8.7 Hz), 8.67 (1H, s).

MS Calcd.: 338. Found: 339 (M+H).

Isopropyl[2,4-dichloro-7-(1-ethylpropyl)-1H-benzimidazol-1-yl]acetate

A mixture of isopropyl[4-chloro-7-(1-ethylpropyl)-2-oxo-2,3-dihydro-1H-benzimidazol-1-yl]acetate (3.73 g, 11.0 mmol) and phosphorus oxychloride (20 mL) was stirred at 100° C. for 48 hours. After cooling, phosphorus oxychloride was evaporated in vacuo. The residue was neutralized with saturated aqueous sodium hydrogen carbonate and extracted with ethyl acetate (X2). The combined organic layer was washed with brine (X1), dried over sodium sulfate and concentrated in vacuo. The residue was purified by silica gel column chromatography eluting with a 5-15% ethyl acetate/hexane gradient mixture to give 3.82 g (10.7 mmol, 97.2%) of the title compound as an oil.

$^1$H NMR (CDCl$_3$) δ: 0.81 (6H, t, J=7.5 Hz), 1.28 (6H, d, J=6.3 Hz), 1.62-1.83 (4H, m), 2.72-2.82 (1H, m), 5.06-5.21 (1H, m), 5.08 (2H, s), 7.05 (1H, d, J=8.0 Hz), 7.28 (1H, d, J=8.0 Hz)

MS Calcd.: 356, 358. Found: 357, 359 (M+H).

Isopropyl[4-chloro-2-[(4-chloro-2-methoxy-6-methylphenyl)amino]-7-(1-ethylpropyl)-1H-benzimidazol-1-yl]acetate A mixture of isopropyl[2,4-dichloro-7-(1-ethylpropyl)-1H-benzimidazol-1-yl]acetate (1.60 g, 4.48 mmol), (4-chloro-2-methoxy-6-methyl)aniline (3.18 g, 18.6 mmol) and N-methyl-2-pyrrolidinone (1 mL) was stirred at 110° C. for 4.5 days. After cooling, the reaction mixture was diluted with saturated aqueous sodium hydrogen carbonate and extracted with ethyl acetate (X1). The organic layer was washed with brine (X1), dried over sodium sulfate and concentrated in vacuo. The residue was purified by silica gel column chromatography eluting with a 5-20% ethyl acetate/hexane gradient mixture. The residual solid was washed with ethyl acetate/diisopropyl ether and n-hexane to give 1.18 g (2.40 mmol, 53.5%) of the title compound as a colorless solid. The filtrate was purified by preparative HPLC to give 204 mg (0.414 mmol, 9.2%) of the title compound as a solid. mp 205-207° C.

$^1$H NMR (CDCl$_3$) δ: 0.82 (6H, t, J=7.4 Hz), 1.30 (6H, d, J=6.3 Hz), 1.58-1.81 (4H, m), 2.11 (3H, s), 2.80-2.92 (1H, m), 3.83 (3H, s), 4.89 (2H, s), 5.09-5.20 (1H, m), 6.56 (1H, s), 6.78 (1H, s), 6.87 (1H, d, J=7.6 Hz), 6.87 (1H, s), 7.14 (1H, d, J=7.6 Hz).

MS Calcd.: 491, 493. Found: 492, 494 (M+H).

Example 103

2-[4-Chloro-2-[(4-chloro-2-methoxy-6-methylphenyl)amino]-7-(1-ethylpropyl)-1H-benzimidazol-1-yl]ethanol

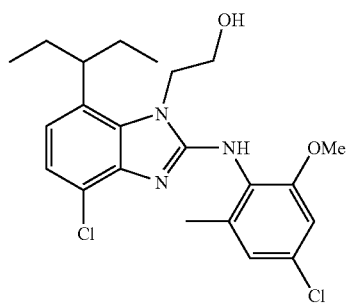

To a solution of isopropyl[4-chloro-2-[(4-chloro-2-methoxy-6-methylphenyl)amino]-7-(1-ethylpropyl)-1H-benzimidazol-1-yl]acetate (453 mg, 0.920 mmol) in tetrahydrofuran (5 mL) was added lithium tetrahydroborate (60 mg, 2.76 mmol), and the mixture was refluxed for 2 hours. After cooling, the reaction mixture was diluted with water and extracted with ethyl acetate (X2). The combined organic layer was washed with brine (X1), dried over sodium sulfate and concentrated in vacuo. The residual solid was recrystallized with ethyl acetate-n-hexane to give 250 mg (0.573 mmol, 62.3%) of the title compound as a colorless crystal. The filtrate was concentrated in vacuo, and the residual solid was recrystallized with ethyl acetate-hexane to give 91 mg (0.209 mmol, 22.7%) of the title compound as a colorless crystal.

$^1$H NMR (CDCl$_3$) δ: 0.85 (6H, t, J=7.2 Hz), 1.65-1.83 (4H, m), 2.16 (3H, s), 2.45-2.60 (1H, br), 2.79-2.87 (1H, m), 3.76 (3H, s), 4.14 (2H, t, J=4.5 Hz), 4.43 (2H, t, J=4.5 Hz), 6.76 (1H, d, J=1.8 Hz), 6.83 (1H, d, J=7.8 Hz), 6.87 (1H, d, J=1.8 Hz), 6.99 (1H, d, J=7.8 Hz), 7.50-7.70 (1H, br).

MS Calcd.: 435, 437. Found: 436, 438 (M+H).

Example 104

[4-Chloro-2-[(4-chloro-2-methoxy-6-methylphenyl)amino]-7-(1-ethylpropyl)-1H-benzimidazol-1-yl]acetic acid

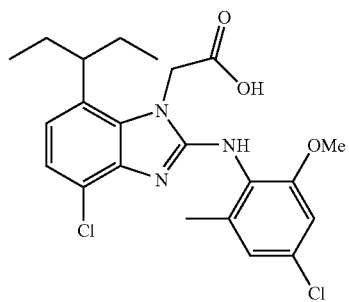

To a solution of 2-[4-chloro-2-[(4-chloro-2-methoxy-6-methylphenyl)amino]-7-(1-ethylpropyl)-1H-benzimidazol-1-yl]ethanol (861 mg, 1.75 mmol) in methanol (5 mL) was added 8N aqueous sodium hydroxide (1.5 mL), and the mixture was stirred at room temperature for 15 hours. Water was added to the reaction mixture, followed by neutralization with 6N hydrochloric acid. The mixture was concentrated in vacuo, and the residue was dissolved in methanol. The precipitate was removed by filtration, and the filtrate was concentrated in vacuo to give 781 mg (1.73 mmol, 99.1%) of the title compound as an amorphous.

$^1$H NMR (CDCl$_3$) δ: 0.76 (6H, t, J=7.2 Hz), 1.52-1.73 (4H, m), 2.07 (3H, s), 3.06-3.15 (1H, m), 3.76 (3H, s), 4.77 (2H, s), 6.77 (1H, d, J=8.4 Hz), 6.93-6.99 (3H, m), 8.64 (1H, s).

MS Calcd.: 449, 451. Found: 450, 452 (M+H).

Example 105

1-{4-Chloro-2-[(4-chloro-2-methoxy-6-methylphenyl)amino]-1-methyl-1H-benzimidazol-7-yl}-2,2-dimethylpropan-1-one

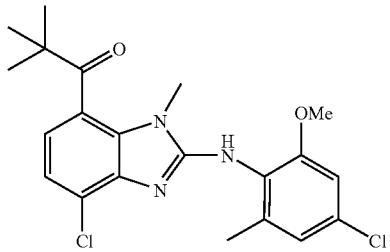

Methyl 7-chloro-3-methyl-2-oxo-2,3-dihydro-1H-benzimidazole-4-carboxylate

A solution of methyl 3-methyl-2-oxo-2,3-dihydro-1H-benzimidazole-4-carboxylate (500 mg, 2.42 mmol), N-chlorosuccinimide (355 mg, 2.66 mmol) and 2,2'-azobis(isobutyronitrile) (20 mg, 0.12 mmol) in carbon tetrachloride (40 mL) was refluxed for 2 days. After cooling, the reaction mixture was concentrated in vacuo. The resultant was extracted with ethyl acetate and water. The organics was dried over magnesium sulfate, filtered, and concentrated in vacuo. The residue was chromatographed on a silica gel to give 167 mg (0.07 mmol, 29%) of the title compound.

$^1$H NMR (CDCl$_3$) δ 3.57 (3H, s), 3.95 (3H, s), 7.07 (1H, d, J=8.4 Hz), 7.50 (1H, d, J=8.4 Hz), 8.03 (1H, br).

MS Calcd.: 240. Found: 241 (M+H).

Methyl 2,4-dichloro-1-methyl-1H-benzimidazole-7-carboxylate

Methyl 7-chloro-3-methyl-2-oxo-2,3-dihydro-1H-benzimidazole-4-carboxylate (150 mg, 0.63 mmol) was dissolved in 3 mL of phosphorous oxychloride and heated at 110° C. overnight. The reaction mixture was allowed to cool to room temperature, poured into a crushed ice, and stirred for 1 h. The resultant was diluted in ethyl acetate, washed with aqueous sodium bicarbonate, dried over magnesium sulfate, filtered and concentrated in vacuo. The obtained (147 mg, 90%) was used in the next reaction without further purification.

MS Calcd.: 257. Found: 258 (M+H).

Methyl 4-chloro-2-[(4-chloro-2-methoxy-6-methylphenyl)amino]-1-methyl-1H-benzimidazole-7-carboxylate A mixture of methyl 2,4-dichloro-1-methyl-1H-benzimidazole-7-carboxylate (100 mg, 0.39 mmol) and 4-chloro-2-methoxy-6-methylaniline (200 mg, 1.17 mmol) was stirred at 130° C. overnight. After cooling, the reaction mixture was neutralized by aqueous sodium hydrogen carbonate and extracted with ethyl acetate. The organics was dried over magnesium sulfate, filtered, and concentrated in vacuo. The residue was chromatographed on a silica gel column to give 68 mg (0.17 mmol, 44%) of the title compound.

$^1$H NMR (CDCl$_3$) δ 2.19 (3H, s), 3.74 (3H, s), 3.80 (3H, s), 3.95 (3H, s), 6.17 (1H, br), 6.76 (1H, d, J=1.8 Hz), 6.88 (1H, d, J=1.8 Hz), 7.14 (1H, d, J=8.1 Hz), 7.53 (1H, d, J=8.1 Hz).

MS Calcd.: 393. Found: 394 (M+H).

1-{4-Chloro-2-[(4-chloro-2-methoxy-6-methylphenyl)amino]-1-methyl-1H-benzimidazol-7-yl}-2,2-dimethylpropan-1-one A n-pentane solution of tert-butyl lithium (1.46 M, 0.5 ml) was added to a solution of methyl 4-chloro-2-[(4-chloro-2-methoxy-6-methylphenyl)amino]-1-methyl-1H-benzimidazole-7-carboxylate (100 mg, 0.23 mmol) in diethyl ether (5 mL) at −78° C. and stirred for 1 h. The reaction mixture was diluted with water (5 mL), stirred at room temperature for 0.5 h and extracted with ethyl acetate. The organics was dried over magnesium sulfate, filtered, and concentrated in vacuo. The residue was purified by preparative HPLC. The resultant was neutralized with aqueous sodium hydrogen carbonate and extracted with ethyl acetate. The organics was dried over magnesium sulfate, filtered, and concentrated in vacuo to give 31 mg (0.073, mmol, 32%) of the title compound.

mp. 249-250° C.

$^1$H NMR (CDCl$_3$) δ 1.37 (9H, s), 2.20 (3H, s), 3.37 (3H, s), 3.80 (3H, s), 6.10 (1H, br), 6.78 (1H, d, J=1.8 Hz), 6.89 (1H, d, J=1.8 Hz), 7.08 (1H, d, J=8.1 Hz), 7.10 (1H, d, J=8.1 Hz).

MS Calcd.: 419. Found: 420 (M+H).

Example 106

3-{4-Chloro-2-[(4-chloro-2-methoxy-6-methylphenyl)amino]-1-methyl-1H-benzimidazol-7-yl}-2,2,4,4-tetramethylpentan-3-ol

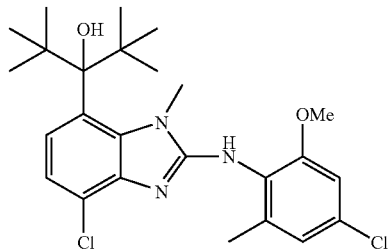

A n-pentane solution of tert-butyl lithium (1.46 M, 0.5 ml) was added to a solution of methyl 4-chloro-2-[(4-chloro-2-methoxy-6-methylphenyl)amino]-1-methyl-1H-benzimidazole-7-carboxylate (100 mg, 0.23 mmol) in diethyl ether (5 ml) at −78° C. and stirred for 1 h. The reaction mixture was diluted with water (5 mL), stirred at room temperature for 0.5 h and extracted with ethyl acetate. The organics was dried over magnesium sulfate, filtered, and concentrated in vacuo. The residue was purified by preparative HPLC. The resultant was neutralized with aqueous sodium hydrogen carbonate and extracted with ethyl acetate. The organics were dried over magnesium sulfate, filtered, and concentrated in vacuo to give 5 mg (0.010 mmol, 5%) of the title compound.

mp. 246-248° C.

$^1$H NMR (CDCl$_3$) δ 1.12 (18H, s), 2.20 (3H, s), 3.67 (3H, s), 3.75 (3H, s), 6.76 (1H, s), 6.87 (1H, s), 7.09 (1H, d, J=9.0 Hz), 7.21 (1H, d, J=9.0 Hz).
MS Calcd.: 477. Found: 478 (M+H).

Example 107

3-{4-Chloro-2-[(4-chloro-2-methoxy-6-methylphenyl)amino]-1-methyl-1H-benzimidazol-7-yl}-2,4-dimethylpentan-3-ol

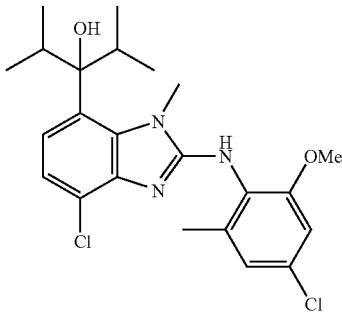

To a solution of methyl 4-chloro-2-[(4-chloro-2-methoxy-6-methylphenyl)amino]-1-methyl-1H-benzimidazole-7-carboxylate (200 mg, 0.50 mmol) in diethylether (3 mL) was added dropwise a pentane solution of isopropyl lithium (0.7 M solution, 5 mL) at −78° C., and stirred at 0° C. for 1 h. The reaction mixture was quenched with 6N hydrochloric acid, and extracted with ethyl acetate. The organic layer was dried over magnesium sulfate, filtered, and concentrated in vacuo. The residue was purified by preparative HPLC eluting with a 5-95% acetonitrile/water gradient mixture to give the title compound (153 mg, 68%).
mp. 218-219° C.
$^1$H NMR (CDCl$_3$) δ 0.87 (d, J=6.9 Hz, 6H), 0.93 (d, J=6.9 Hz, 6H), 2.19 (s, 3H), 2.31-2.43 (m, 2H), 3.77 (s, 3H), 3.87 (s, 3H), 6.76 (d, J=2.1 Hz, 1H), 6.79 (d, J=8.4 Hz, 1H), 6.88 (d, J=2.1 Hz, 1H), 7.08 (d, J=8.4 Hz, 1H).
MS Calcd.: 449. Found: 450 (M+H).

Example 108

4-Chloro-N-(4-chloro-2-methoxy-6-methylphenyl)-7-(1-isopropyl-2-methylprop-1-en-1-yl)-1-methyl-1H-benzimidazol-2-amine

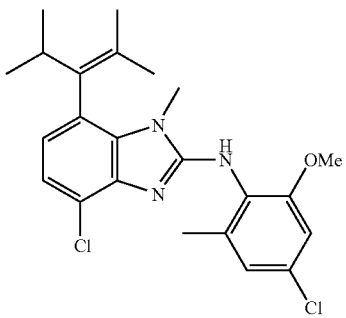

A solution of 3-{4-chloro-2-[(4-chloro-2-methoxy-6-methylphenyl)amino]-1-methyl-1H-benzimidazol-7-yl}-2,4-dimethylpentan-3-ol (75 mg, 0.17 mmol) in trifluoroacetic acid (3 mL) was heated at 70° C. for 1 h. After cooling, the reaction mixture was concentrated in vacuo, neutralized with saturated sodium hydrogen carbonate, and extracted with ethyl acetate. The organic layer was dried over magnesium sulfate, filtered, and concentrated in vacuo. The residue was purified by preparative HPLC eluting with a 5-95% acetonitrile/water gradient mixture to give the title compound (58 mg, 80%).
mp. 166-168° C.
$^1$H NMR (CDCl$_3$) δ 0.65 (d, J=6.6 Hz, 3H), 1.06 (d, J=6.6 Hz, 3H), 1.40 (s, 3H), 1.82 (s, 3H), 2.37 (s, 3H), 3.02-3.08 (m, 1H), 3.19 (s, 3H), 3.67 (s, 3H), 6.70 (d, J=8.7 Hz, 1H), 6.76 (d, J=2.1 Hz, 1H), 6.90 (d, J=2.1 Hz, 1H), 7.22 (d, J=8.7 Hz, 1H).
MS Calcd.: 431. Found: 432 (M+H).

Example 109

4-Chloro-N-(4-chloro-2-methoxy-6-methylphenyl)-7-[(1Z)-1-ethylprop-1-en-1-yl]-1-methyl-1H-benzimidazol-2-amine

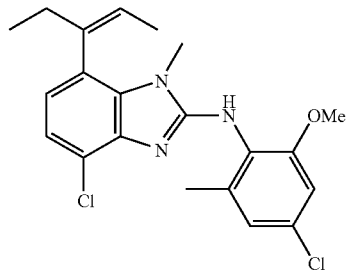

Example 109 was prepared in the similar method described in Example 108.
mp. 166-168° C.
$^1$H NMR (CDCl$_3$) δ 0.96 (t, J=7.5 Hz, 3H), 1.82 (d, J=6.6 Hz, 3H), 2.19 (s, 3H), 2.32-2.57 (m, 2H), 3.58 (s, 3H), 3.80 (s, 3H), 5.52 (q, J=6.6 Hz, 1H), 6.04 (s, 1H), 6.70 (d, J=8.1 Hz, 1H), 6.77 (d, J=2.1 Hz, 1H), 6.88 (d, J=2.1 Hz, 1H), 7.05 (d, J=8.1 Hz, 1H).
MS Calcd.: 403. Found: 404 (M+H).
Example 110-124 were prepared in the similar method described in Example 77.

Example 110

4-Chloro-N-(2,4-dichloro-6-methylphenyl)-7-(1-ethylpropyl)-1-methyl-1H-benzimidazol-2-amine

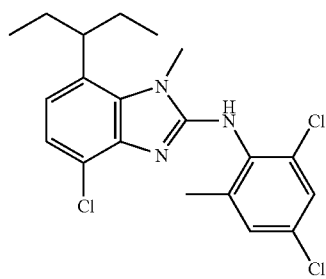

mp 237-238° C.

¹H NMR (CDCl₃) δ 0.85 (t, J=7.2 Hz, 6H), 1.60-1.85 (m, 4H), 2.18 (s, 3H), 3.15-3.25 (m, 1H), 3.71 (s, 3H), 6.00-6.05 (m, 1H), 6.87 (d, J=8.4 Hz, 1H), 7.05 (m, 1H), 7.16 (d, J=2.4 Hz, 1H), 7.31 (d, J=2.4 Hz, 1H).
MS Calcd.: 409. Found: 410 (M+H), 412.

Example 111

4-Chloro-N-(2,4-dimethoxy-6-methylpyridin-3-yl)-7-(1-ethylpropyl)-1-methyl-1H-benzimidazol-2-amine

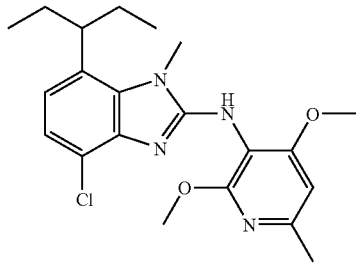

¹H NMR (CDCl₃) δ 0.81 (t, J=7.5 Hz, 6H), 1.60-1.80 (m, 4H), 2.43 (s, 3H), 3.15 (m, 1H), 3.66 (s, 3H), 3.78 (s, 3H), 3.88 (s, 3H), 6.45 (s, 1H), 6.85 (d, J=8.1 Hz, 1H), 7.11 (d, J=8.1 Hz, 1H), 7.25 (m, 1H).
MS Calcd.: 402. Found: 403 (M+H), 405.

Example 112

4-Chloro-N-[2-methoxy-5-(trifluoromethyl)phenyl]-1-methyl-7-(1-propylbutyl)-1H-benzimidazol-2-amine

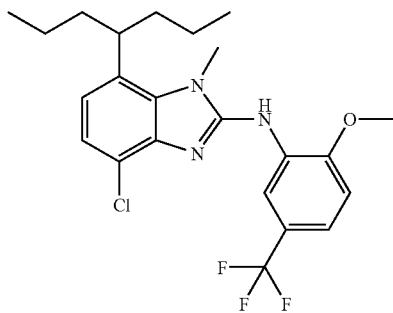

mp 178-180° C.
¹H NMR (CDCl₃) δ 0.86 (t, J=7.5 Hz, 6H), 1.10-1.30 (m, 4H), 1.55-1.80 (m, 4H), 3.30-3.45 (m, 1H), 3.75 (s, 3H), 3.99 (s, 3H), 6.90-7.00 (m, 3H), 7.20-7.30 (m, 2H), 8.24 (s, 1H).
MS Calcd.: 453. Found: 454 (M+H).

Example 113

4-Chloro-N-[2,4-dichloro-5-(trifluoromethyl)phenyl]-1-methyl-7-(1-propylbutyl)-1H-benzimidazol-2-amine

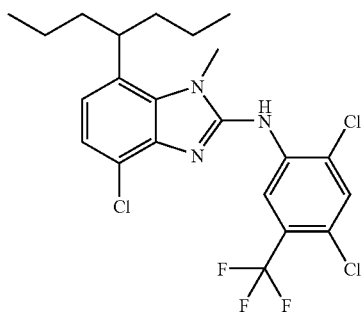

mp 206-208° C.

¹H NMR (CDCl₃) δ 0.86 (t, J=7.5 Hz, 6H), 1.10-1.30 (m, 4H), 1.55-1.80 (m, 4H), 3.30-3.45 (m, 1H), 3.86 (s, 3H), 6.89 (s, 1H), 7.00 (d, J=8.4 Hz, 1H), 7.23 (d, J=8.4 Hz, 1H), 7.56 (s, 1H), 8.25-8.65 (br, 1H).
MS Calcd.: 493. Found: 494 (M+H).

Example 114

4-Chloro-N-(4-chloro-2,6-dimethylphenyl)-1-methyl-7-(1-propylbutyl)-1H-benzimidazol-2-amine

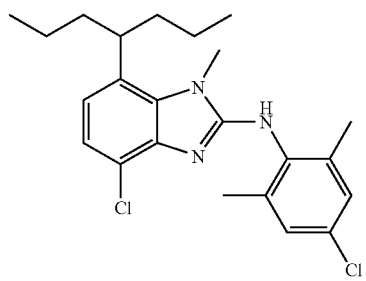

mp 230-232° C.

¹H NMR (CDCl₃) δ 0.85 (t, J=7.5 Hz, 6H), 1.10-1.30 (m, 4H), 1.55-1.80 (m, 4H), 2.10-2.20 (m, 6H), 3.20-3.90 (m, 4H), 6.00 (s, 1H), 6.85 (d, J=8.4 Hz, 1H), 7.00-7.20 (m, 3H).
MS Calcd.: 417. Found: 418 (M+H).

Example 115

N-(4-Bromo-2,6-dimethylphenyl)-4-chloro-1-methyl-7-(1-propylbutyl)-1H-benzimidazol-2-amine

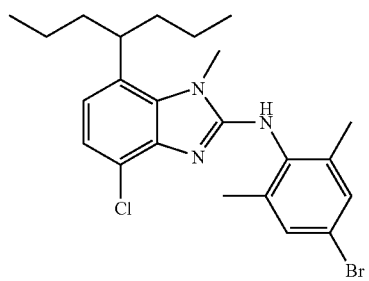

mp 234-236° C.

¹H NMR (CDCl₃) δ 0.85 (t, J=7.5 Hz, 6H), 1.10-1.30 (m, 4H), 1.55-1.80 (m, 4H), 2.10-2.20 (m, 6H), 3.15-3.80 (m, 4H), 5.90-6.20 (br, 1H), 6.85 (d, J=8.4 Hz, 1H), 7.00-7.20 (m, 1H), 7.20-7.25 (m, 2H).
MS Calcd.: 463. Found: 464 (M+H).

Example 116

5-{[4-Chloro-1-methyl-7-(1-propylbutyl)-1H-benzimidazol-2-yl]amino}-4-methylpyridin-2(1H)-one

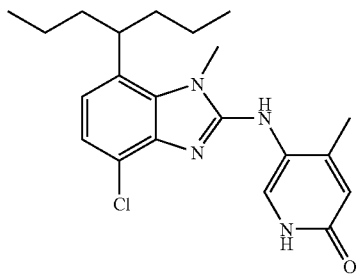

mp 237-239° C.
$^1$H NMR (CDCl$_3$) δ 0.80-0.95 (m, 6H), 1.00-1.80 (m, 8H), 2.10-2.30 (m, 3H), 3.20-4.85 (m, 4H), 5.55 (s, 1H), 6.30-7.70 (m, 4H), 8.35-8.60 (br, 1H).
MS Calcd.: 386. Found: 387 (M+H).

Example 117

4-Chloro-1-methyl-7-(1-propylbutyl)-N-(5,6,7,8-tetrahydronaphthalen-1-yl)-1H-benzimidazol-2-amine

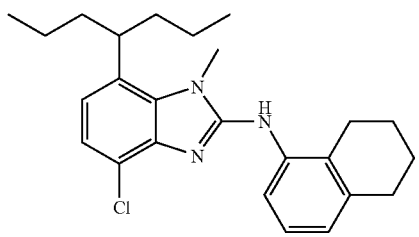

mp 236-238° C.
$^1$H NMR (CDCl$_3$) δ 0.86 (t, J=7.5 Hz, 6H), 1.10-1.30 (m, 4H), 1.60-1.95 (m, 8H), 2.66 (t, J=6.3 Hz, 2H), 2.81 (t, J=6.3 Hz, 2H), 3.20-3.40 (m, 1H), 3.60 (s, 3H), 6.11 (s, 1H), 6.69 (d, J=7.8 Hz, 1H), 6.81 (d, J=7.8 Hz, 1H), 6.96 (d, J=8.4 Hz, 1H), 7.03 (t, J=7.8 Hz, 1H), 7.20 (d, J=8.4 Hz, 1H).
MS Calcd.: 409. Found: 410 (M+H).

Example 118

4-Chloro-2-(5-methoxy-2,3-dihydro-1H-indol-1-yl)-1-methyl-7-(1-propylbutyl)-1H-benzimidazole

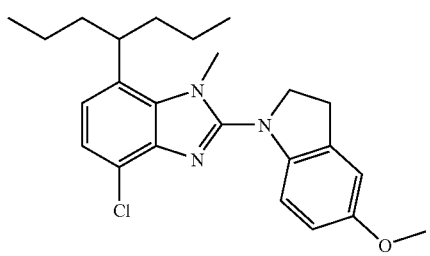

$^1$H NMR (CDCl$_3$) δ 0.89 (t, J=7.5 Hz, 6H), 1.15-1.30 (m, 4H), 1.60-1.80 (m, 4H), 3.17 (t, J=8.1 Hz, 2H), 3.30-3.50 (m, 1H), 3.76 (s, 6H), 4.20 (t, J=8.1 Hz, 2H), 6.45-7.30 (m, 5H).
MS Calcd.: 411. Found: 412 (M+H).

Example 119

1-[4-Chloro-1-methyl-7-(1-propylbutyl)-1H-benzimidazol-2-yl]-6-methoxy-1,2,3,4-tetrahydroquinoline

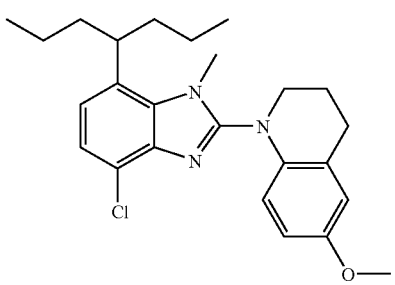

$^1$H NMR (CDCl$_3$) δ 0.86 (t, J=7.2 Hz, 6H), 1.15-1.30 (m, 4H), 1.55-1.75 (m, 4H), 2.05-2.20 (m, 2H), 2.88 (t, J=6.6 Hz, 2H), 3.30-3.40 (m, 1H), 3.58 (s, 3H), 3.75 (s, 3H), 3.88 (t, J=6.6 Hz, 2H), 6.34 (d, J=8.5 Hz, 1H), 6.57 (dd, J=8.5, 3.0 Hz, 1H), 6.69 (d, J=3.0 Hz, 1H), 6.97 (d, J=8.1 Hz, 1H), 7.19 (d, J=8.1 Hz, 1H).
MS Calcd.: 425. Found: 426 (M+H).

Example 120

1-[4-Chloro-1-methyl-7-(1-propylbutyl)-1H-benzimidazol-2-yl]-7-methoxy-2,3,4,5-tetrahydro-1H-1-benzazepine

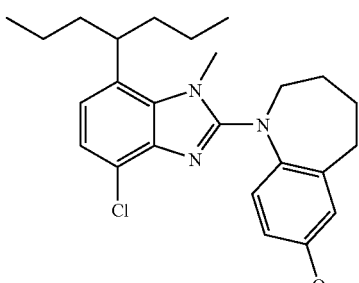

$^1$H NMR (CDCl$_3$) δ 0.80 (t, J=7.2 Hz, 6H), 1.05-1.20 (m, 4H), 1.50-1.90 (m, 8H), 2.80-3.00 (m, 2H), 3.10-3.25 (m, 1H), 3.19 (s, 3H), 3.79 (s, 3H), 3.80-4.30 (br, 2H), 6.95 (m, 2H), 6.79 (d, J=2.4 Hz, 1H), 6.87 (d, J=8.4 Hz, 1H), 7.14 (d, J=8.4 Hz, 1H).
MS Calcd.: 439. Found: 440 (M+H).

Example 121

5-Bromo-N-(4-chloro-2-methoxy-6-methylphenyl)-7-(1-ethylpropyl)-1-methyl-1H-benzimidazol-2-amine

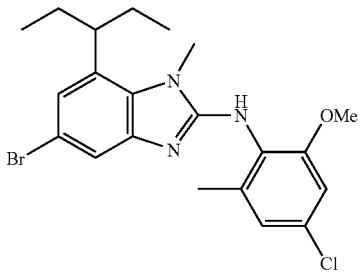

mp. 276-278° C.

$^1$H NMR (CDCl$_3$) δ 0.86 (t, J=7.5 Hz, 3H), 1.66-1.84 (m, 4H), 2.01 (s, 3H), 2.14 (s, 3H), 3.13-3.21 (m, 1H), 3.82 (s, 3H), 3.83 (s, 3H), 5.80-6.20 (br, 1H), 6.80 (d, J=2.4 Hz, 1H), 6.89 (d, J=2.4 Hz, 1H), 7.05 (s, 1H), 7.47 (s, 1H).

MS Calcd.: 493. Found: 494 (M+H).

Example 122

5-Chloro-4-{[4-chloro-1-methyl-7-(1-propylbutyl)-1H-benzimidazol-2-yl]amino}-2-(trifluoromethyl)phenol

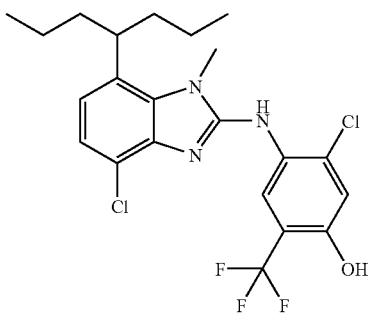

mp 197-199° C.

$^1$H NMR (CDCl$_3$) δ 0.87 (t, J=7.2 Hz, 6H), 1.15-1.35 (m, 4H), 1.60-1.80 (m, 5H), 3.30-3.40 (m, 1H), 3.88 (s, 3H), 6.97 (d, J=8.4 Hz, 1H), 7.13 (s, 1H), 7.19 (d, J=8.4 Hz, 1H), 7.20-7.30 (m, 2H).

MS Calcd.: 473. Found: 474 (M+H).

Example 123

4-Chloro-N-[2,4-dimethoxy-5-(trifluoromethyl)phenyl]-1-methyl-7-(1-propylbutyl)-1H-benzimidazol-2-amine

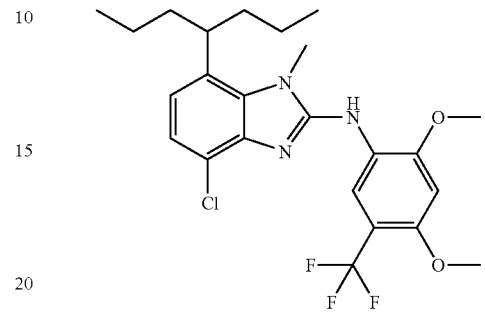

mp 196-198° C.

$^1$H NMR (CDCl$_3$) δ 0.85 (t, J=7.2 Hz, 6H), 1.15-1.30 (m, 4H), 1.60-1.80 (m, 4H), 3.30-3.40 (m, 1H), 3.78 (s, 3H), 3.88 (s, 3H), 3.99 (s, 3H), 6.57 (s, 1H), 6.66 (s, 1H), 6.92 (d, J=8.4 Hz, 1H), 7.17 (d, J=8.4 Hz, 1H), 8.22 (s, 1H).

MS Calcd.: 483. Found: 484 (M+H).

Example 124-144 were prepared in the similar method described in Example 97.

Example 124

4-Chloro-2-(mesityloxy)-1-methyl-7-(1-propylbutyl)-1H-benzimidazole

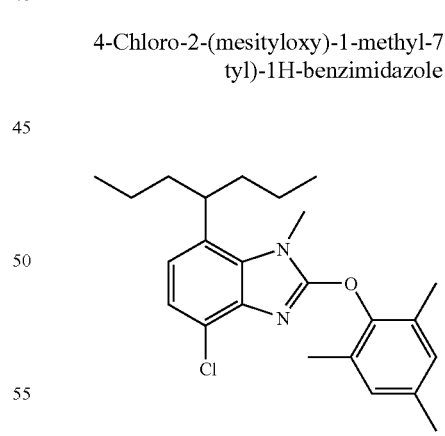

mp 165-167° C.

$^1$H NMR (CDCl$_3$) δ 0.88 (t, J=7.2 Hz, 6H), 1.20-1.40 (m, 4H), 1.60-1.80 (m, 4H), 2.17 (s, 6H), 2.30 (s, 3H), 3.30-3.45 (m, 1H), 3.96 (s, 3H), 6.85-6.95 (m, 3H), 7.10 (d, J=8.1 Hz, 1H).

MS Calcd.: 398. Found: 399 (M+H).

Example 125

4-Chloro-2-(4-chloro-2,6-dimethylphenoxy)-7-(1-ethylpropyl)-1-methyl-1H-benzimidazole

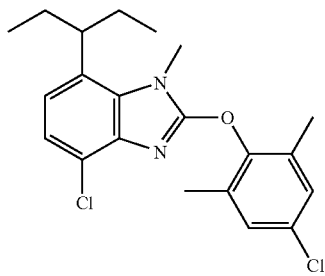

mp 168-169° C.
$^1$H NMR (CDCl$_3$) δ 0.87 (t, J=7.5 Hz, 6H), 1.60-1.85 (m, 4H), 2.81 (s, 6H), 3.20-3.30 (m, 1H), 3.98 (s, 3H), 6.92 (d, J=8.1 Hz, 1H), 7.10 (s, 2H), 7.13 (d, J=8.1 Hz, 1H).
MS Calcd.: 390. Found: 391 (M+H), 393.

Example 126

4-Chloro-2-(2,6-dimethoxy-4-methylphenoxy)-7-(1-ethylpropyl)-1-methyl-1H-benzimidazole

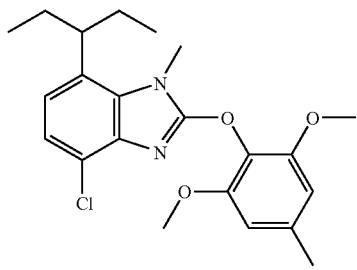

mp 161-162° C.
$^1$H NMR (CDCl$_3$) δ 0.84 (t, J=7.5 Hz, 6H), 1.60-1.85 (m, 4H), 2.36 (s, 3H), 3.20-3.30 (m, 1H), 3.77 (s, 6H), 3.95 (s, 3H), 6.47 (s, 2H), 6.89 (d, J=8.4 Hz, 1H), 7.10 (d, J=8.4 Hz, 1H).
MS Calcd.: 402. Found: 403 (M+H), 405.

Example 127

4-Chloro-2-(2,4-dichlorophenoxy)-1-methyl-7-(1-propylbutyl)-1H-benzimidazole

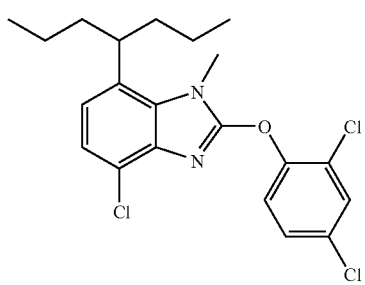

mp 87-88° C.

$^1$H NMR (CDCl$_3$) δ 0.87 (t, J=7.2 Hz, 6H), 1.10-1.40 (m, 4H), 1.60-1.90 (m, 4H), 3.30-3.45 (m, 1H), 3.97 (s, 3H), 6.98 (d, J=8.4 Hz, 1H), 7.17 (d, J=8.4 Hz, 1H), 7.32 (dd, J=8.8, 2.4 Hz, 1H), 7.47 (d, J=2.4 Hz, 1H), 7.74 (d, J=8.8 Hz, 1H).
MS Calcd.: 424. Found: 425 (M+H).

Example 128

2-(4-Bromo-2-chlorophenoxy)-4-chloro-1-methyl-7-(1-propylbutyl)-1H-benzimidazole

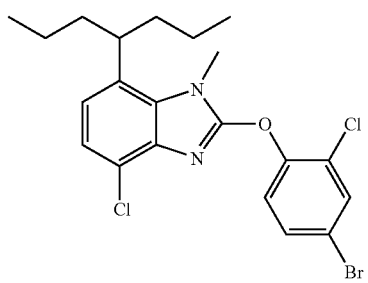

mp 97-99° C.
$^1$H NMR (CDCl$_3$) δ 0.87 (t, J=7.2 Hz, 6H), 1.10-1.40 (m, 4H), 1.60-1.90 (m, 4H), 3.30-3.45 (m, 1H), 3.97 (s, 3H), 6.98 (d, J=8.4 Hz, 1H), 7.18 (d, J=8.4 Hz, 1H), 7.47 (dd, J=8.8, 2.4 Hz, 1H), 7.63 (d, J=2.4 Hz, 1H), 7.70 (d, J=8.8 Hz, 1H).
MS Calcd.: 470. Found: 471 (M+H).

Example 129

4-Chloro-2-(2,4-dichloro-6-methylphenoxy)-1-methyl-7-(1-propylbutyl)-1H-benzimidazole

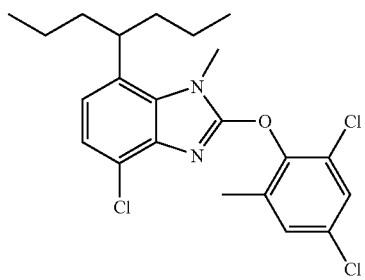

mp 148-150° C.
$^1$H NMR (CDCl$_3$) δ 0.88 (t, J=7.2 Hz, 6H), 1.10-1.40 (m, 4H), 1.60-1.80 (m, 4H), 2.31 (s, 3H), 3.30-3.45 (m, 1H), 3.98 (s, 3H), 6.95 (d, J=8.4 Hz, 1H), 7.14 (d, J=8.4 Hz, 1H), 7.20 (d, J=2.4 Hz, 1H), 7.31 (d, J=2.4 Hz, 1H).
MS Calcd.: 438. Found: 439 (M+H).

Example 130

4-Chloro-2-(4-chloro-2,6-dimethylphenoxy)-1-methyl-7-(1-propylbutyl)-1H-benzimidazole

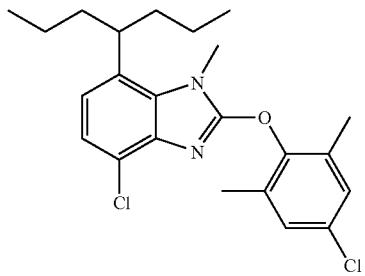

mp 160-162° C.
$^1$H NMR (CDCl$_3$) δ 0.88 (t, J=7.2 Hz, 6H), 1.15-1.40 (m, 4H), 1.60-1.80 (m, 4H), 2.19 (s, 6H), 3.30-3.45 (m, 1H), 3.97 (s, 3H), 6.94 (d, J=8.4 Hz, 1H), 7.10-7.20 (m, 3H).
MS Calcd.: 418. Found: 419 (M+H).

Example 131

2-(4-Bromo-2,6-dimethylphenoxy)-4-chloro-1-methyl-7-(1-propylbutyl)-1H-benzimidazole

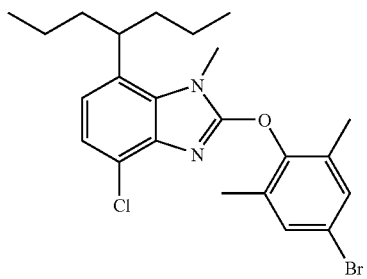

mp 155-157° C.
$^1$H NMR (CDCl$_3$) δ 0.88 (t, J=7.2 Hz, 6H), 1.20-1.40 (m, 0.4H), 1.60-1.80 (m, 4H), 2.19 (s, 6H), 3.30-3.45 (m, 1H), 3.97 (s, 3H), 6.94 (d, J=8.4 Hz, 1H), 7.13 (d, J=8.4 Hz, 1H), 7.20-7.30 (m, 2H).
MS Calcd.: 464. Found: 465 (M+H).

Example 132

4-Chloro-1-methyl-7-(1-propylbutyl)-2-(2,4,6-trichlorophenoxy)-1H-benzimidazole

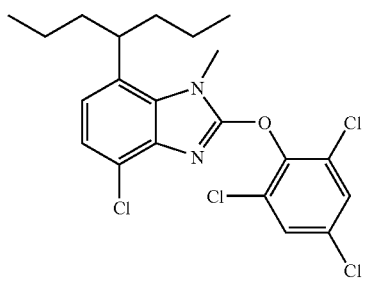

mp 148-150° C.
$^1$H NMR (CDCl$_3$) δ 0.88 (t, J=7.2 Hz, 6H), 1.20-1.40 (m, 4H), 1.60-1.80 (m, 4H), 3.30-3.45 (m, 1H), 3.99 (s, 3H), 6.97 (d, J=8.4 Hz, 1H), 7.15 (d, J=8.4 Hz, 1H), 7.26 (s, 1H), 7.43 (s, 1H).
MS Calcd.: 458. Found: 459 (M+H).

Example 133

4-Chloro-2-(2,6-dimethoxy-4-methylphenoxy)-1-methyl-7-(1-propylbutyl)-1H-benzimidazole

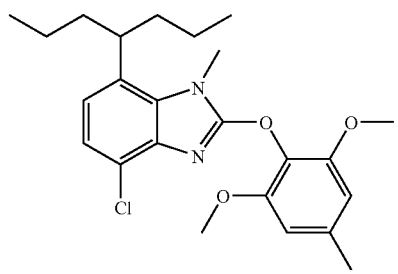

mp 203-205° C.
$^1$H NMR (CDCl$_3$) δ 0.87 (t, J=7.2 Hz, 6H), 1.15-1.40 (m, 4H), 1.60-1.80 (m, 4H), 2.36 (s, 3H), 3.30-3.45 (m, 1H), 3.77 (s, 6H), 3.95 (s, 3H), 6.47 (s, 2H), 6.90 (d, J=8.4 Hz, 1H), 7.10 (d, J=8.4 Hz, 1H).
MS Calcd.: 430. Found: 431 (M+H).

Example 134

9-{[4-Chloro-1-methyl-7-(1-propylbutyl)-1H-benzimidazol-2-yl]oxy}-1,2,5,6-tetrahydro-4H-pyrrolo[3,2,1-ij]quinolin-4-one

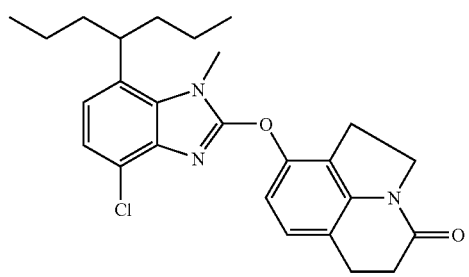

mp 150-152° C.
$^1$H NMR (CDCl$_3$) δ 0.88 (t, J=7.2 Hz, 6H), 1.15-1.40 (m, 4H), 1.60-1.80 (m, 4H), 2.70 (t, J=7.8 Hz, 2H), 2.98 (t, J=7.8 Hz, 2H), 3.17 (t, J=8.7 Hz, 2H), 3.30-3.45 (m, 1H), 3.92 (s, 3H), 4.10 (t, J=8.7 Hz, 2H), 6.90-7.05 (m, 3H), 7.17 (d, J=8.1 Hz, 1H).
MS Calcd.: 451. Found: 452 (M+H).

Example 135

2-(2-Bromo-4-chlorophenoxy)-4-chloro-7-(1-ethylpropyl)-1-methyl-1H-benzimidazole

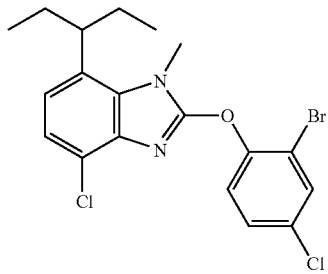

mp 114-115° C.
¹H NMR (CDCl₃) δ 0.85 (t, J=7.2 Hz, 6H), 1.60-1.85 (m, 4H), 3.15-3.30 (m, 1H), 3.98 (s, 3H), 6.96 (d, J=8.4 Hz, 1H), 7.18 (d, J=8.4 Hz, 1H), 7.37 (dd, J=2.4, 8.7 Hz, 1H), 7.63 (d, J=2.4 Hz, 1H), 7.76 (d, J=7.8 Hz, 1H)
MS Calcd.: 440. Found: 441 (M+H), 443, 445.

Example 136

5-Bromo-2-(4-chloro-2,6-dimethylphenoxy)-7-(1-ethylpropyl)-1-methyl-1H-benzimidazole

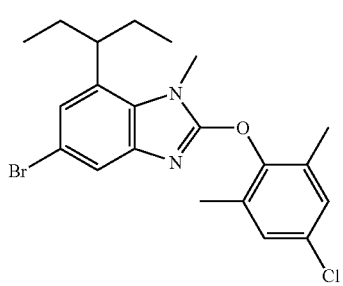

mp 214-216° C.
¹H NMR (CDCl₃) δ 0.86 (t, J=7.5 Hz, 6H), 1.65-1.83 (m, 4H), 2.18 (s, 6H), 3.18-3.26 (m, 1H), 3.95 (s, 3H), 7.08-7.10 (m, 3H), 7.46 (d, J=2.1 Hz, 1H).
MS Calcd.: 433. Found: 434 (M+H).

Example 137

2-(4-Bromo-2,6-dimethylphenoxy)-4-chloro-7-(1-ethylpropyl)-1-methyl-1H-benzimidazole

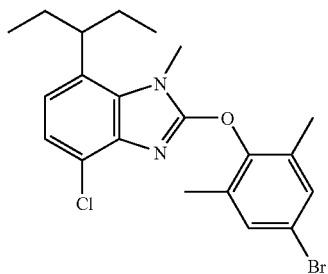

mp 197-198° C.

¹H NMR (CDCl₃) δ 0.86 (t, J=7.2 Hz, 6H), 1.75-1.82 (m, 4H), 2.18 (s, 6H), 3.19-3.25 (m, 1H), 3.97 (s, 3H), 6.91 (d, J=8.1 Hz, 1H), 7.12 (d, J=8.1 Hz, 1H), 7.24 (s, 2H).
MS Calcd.: 434. Found: 435 (M+H).

Example 138

4-Chloro-7-(1-ethylpropyl)-1-methyl-2-(2,4,6-trichlorophenoxy)-1H-benzimidazole

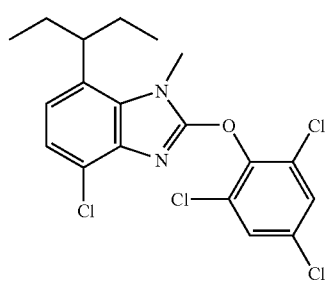

mp 155-157° C.
¹H NMR (CDCl₃) δ 0.86 (t, J=7.2 Hz, 6H), 1.65-1.77 (m, 4H), 3.18-3.25 (m, 1H), 3.99 (s, 3H), 6.93 (d, J=8.4 Hz, 1H), 7.15 (d, J=8.4 Hz, 1H), 7.42 (s, 2H).
MS Calcd.: 430. Found: 431 (M+H).

Example 139

4-Chloro-7-(1-ethylpropyl)-2-[(4-methoxy-2,6-dimethylpyridin-3-yl)oxy]-1-methyl-1H-benzimidazole

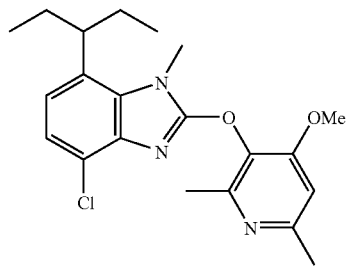

mp 183-184° C.

¹H NMR (CDCl₃) δ 0.86 (t, J=7.2 Hz, 6H), 1.68-1.82 (m, 4H), 2.45 (s, 3H), 2.52 (s, 3H), 3.20-3.26 (m, 1H), 3.76 (s, 3H), 3.96 (s, 3H), 6.66 (s, 1H), 6.91 (d, J=8.4 Hz, 1H), 7.12 (d, J=8.4 Hz, 1H).
MS Calcd.: 387. Found: 388 (M+H).

Example 140

4-Chloro-2-[2,6-dichloro-4-(trifluoromethoxy)phenoxy]-7-(1-ethylpropyl)-1-methyl-1H-benzimidazole

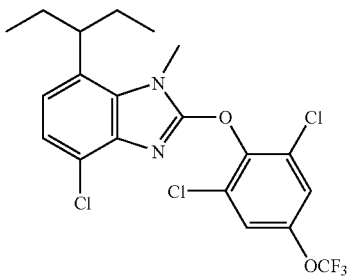

mp 145-147° C.
$^1$H NMR (CDCl$_3$) δ 0.85 (t, J=7.2 Hz, 6H), 1.68-1.82 (m, 4H), 3.20-3.24 (m, 1H), 4.00 (s, 3H), 6.95 (d, J=8.4 Hz, 1H), 7.16 (d, J=8.4 Hz, 1H), 7.32 (s, 2H).
MS Calcd.: 480. Found: 481 (M+H).

Example 141

3-{[4-Chloro-7-(1-ethylpropyl)-1-methyl-1H-benzimidazol-2-yl]oxy}-N,N,2,6-tetramethylpyridin-4-amine

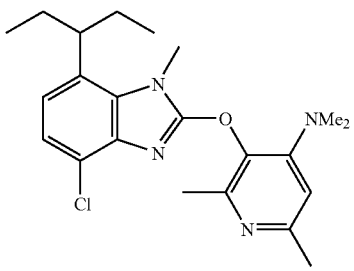

mp 175-177° C.
$^1$H NMR (CDCl$_3$) δ 0.86 (t, J=7.2 Hz, 6H), 1.70-1.82 (m, 4H), 2.27 (s, 3H), 2.46 (s, 3H), 2.92 (s, 6H), 3.20-3.24 (m, 1H), 3.97 (s, 3H), 6.49 (s, 1H), 6.91 (d, J=8.1 Hz, 1H), 7.12 (d, J=8.1 Hz, 1H).
MS Calcd.: 400. Found: 401 (M+H).

Example 142

3,5-Dichloro-4-{[4-chloro-7-(1-ethylpropyl)-1-methyl-1H-benzimidazol-2-yl]oxy}-N,N-dimethylaniline

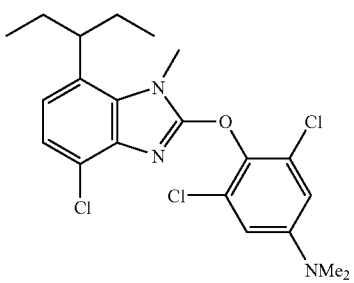

mp 200-202° C.

$^1$H NMR (CDCl$_3$) δ 0.86 (t, J=7.2 Hz, 6H), 1.68-1.81 (m, 4H), 2.97 (s, 6H), 3.20-3.26 (m, 1H), 3.98 (s, 3H), 6.62 (s, 2H), 6.91 (d, J=8.4 Hz, 1H), 7.12 (d, J=8.4 Hz, 1H).
MS Calcd.: 439. Found: 440 (M+H).

Example 143

3,5-Dichloro-2-{[4-chloro-7-(1-ethylpropyl)-1-methyl-1H-benzimidazol-2-yl]oxy}-N,N-dimethylbenzamide

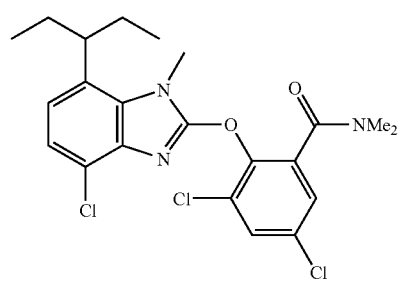

mp 141-143° C.
$^1$H NMR (CDCl$_3$) δ 0.84 (t, J=7.2 Hz, 6H), 1.67-1.81 (m, 4H), 2.63 (s, 3H), 3.08 (s, 3H), 3.20-3.23 (m, 1H), 3.95 (s, 3H), 6.95 (d, J=8.4 Hz, 1H), 7.14 (d, J=8.4 Hz, 1H), 7.18 (d, J=2.4 Hz, 1H), 7.51 (d, J=2.4 Hz, 1H).
MS Calcd.: 467. Found: 468 (M+H).

Example 144

4-Chloro-2-(4-chloro-2-methoxy-6-methylphenoxy)-7-(1-ethyl-1-propyl)-1-methyl-1H-benzimidazole

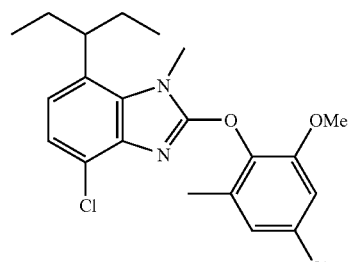

mp 165-167° C.
$^1$H NMR (CDCl$_3$) δ 0.86 (t, J=7.2 Hz, 6H), 1.75-1.82 (m, 4H), 2.27 (s, 3H), 3.20-3.24 (m, 1H), 3.71 (s, 3H), 3.95 (s, 3H), 6.81 (d, J=2.4 Hz, 1H), 6.86 (d, J=2.4 Hz, 1H), 6.90 (d, J=8.1 Hz, 1H), 7.11 (d, J=8.1 Hz, 1H).
MS Calcd.: 406. Found: 407 (M+H).

Example 145

2-(2,4-Dichloro-6-methylphenoxy)-7-(1-ethylpropyl)-4-methoxy-1-methyl-1H-benzimidazole

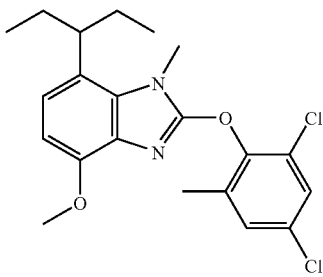

A mixture of 2,4-dichloro-7-(1-ethylpropyl)-1-methyl-1H-benzimidazole (200 mg, 0.750 mmol), 2,4-dichloro-6-methylphenol (398 mg, 2.25 mmol), potassium carbonate (311 mg, 2.25 mmol) and 1-methyl-2-pyrrolidone (0.5 ml) was stirred at 120° C. for 12 h under nitrogen atmosphere. The mixture was diluted with water, extracted with ethyl acetate, and washed with brine. The organic layer was dried over magnesium sulfate, and concentrated in vacuo. The residue was purified by chromatography on silica gel with a 2-30% ethyl acetate/n-hexane gradient mixture and crystallized from methanol to afford the title compound as colorless crystals (109 mg, 36%).

mp 130-131° C.

$^1$H NMR (CDCl$_3$) δ 0.86 (t, J=7.5 Hz, 6H), 1.60-1.85 (m, 4H), 2.30 (s, 3H), 3.15-3.25 (m, 1H), 3.89 (s, 3H), 3.97 (s, 3H), 6.64 (d, J=8.4 Hz, 1H), 6.92 (d, J=8.4 Hz, 1H), 7.15 (d, J=1.8 Hz, 1H), 7.25 (d, J=1.8 Hz, 1H).

MS Calcd.: 406. Found: 407 (M+H), 409.

Example 146

2-(2-Bromo-4-chlorophenoxy)-7-(1-ethylpropyl)-4-methoxy-1-methyl-1H-benzimidazole

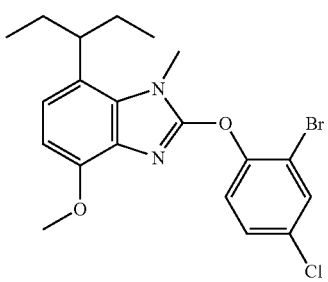

Example 146 was prepared in the similar method described in Example 145.

mp 106-107° C.

$^1$H NMR (CDCl$_3$) δ 0.85 (t, J=7.2 Hz, 6H), 1.50-1.85 (m, 4H), 3.10-3.25 (m, 1H), 3.92 (s, 3H), 3.97 (s, 3H), 6.66 (d, J=8.7 Hz, 1H), 6.95 (d, J=8.7 Hz, 1H), 7.32 (dd, J=2.4, 7.8 Hz, 1H), 7.59 (d, J=2.4 Hz, 1H), 7.66 (d, J=7.8 Hz, 1H)

MS Calcd.: 436. Found: 437 (M+H), 439, 441.

Example 147

2-(2-Bromo-4-chlorophenoxy)-7-(1-ethylpropyl)-1-methyl-1H-benzimidazol-4-ol

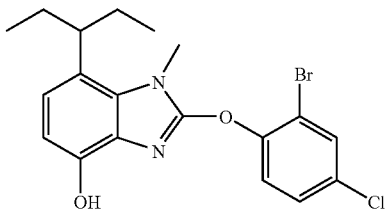

To a solution of 2-(2-bromo-4-chlorophenoxy)-7-(1-ethylpropyl)-4-methoxy-1-methyl-1H-benzimidazole (80 mg, 0.18 mmol) in dichloromethane (2 mL) was added dropwise a dichloromethane solution (1M, 2 mL) of boron tribromide at 0° C., and stirred at room temperature for 1 h. The reaction mixture was cooled at 0° C., quenched with water, and extracted with ethyl acetate. The organic layer was dried over magnesium sulfate, filtered, and concentrated in vacuo. The residue was washed with isopropyl ether and hexane (1:1) to give the title compound (67 mg, 86%).

mp 175-177° C.

$^1$H NMR (CDCl$_3$) δ 0.85 (t, J=7.5 Hz, 6H), 1.66-1.82 (m, 4H), 3.08-3.18 (m, 1H), 3.96 (s, 3H), 6.00-6.40 (br, 1H), 6.71 (d, J=8.1 Hz, 1H), 6.92 (d, J=8.1 Hz, 1H), 7.35 (dd, J=2.4, 8.7 Hz, 1H), 7.54 (d, J=8.7 Hz, 1H), 7.65 (d, J=2.4 Hz, 1H).

MS Calcd.: 422. Found: 423 (M+H).

Example 148

2-(2-Bromo-4-chlorophenoxy)-4-(difluoromethoxy)-7-(1-ethylpropyl)-1-methyl-1H-benzimidazole

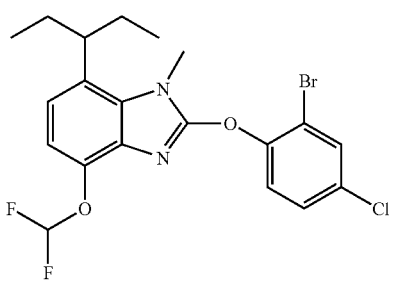

To a solution of aqueous potassium hydroxide (50% solution) was added dropwise a solution of 2-(2-bromo-4-chlorophenoxy)-7-(1-ethylpropyl)-1-methyl-1H-benzimidazol-4-ol in dichloromethane (2 mL) at 0° C. After stirring for 20 min, to the reaction mixture was bubbled chlorodifluoromethane at 0° C. for 30 min. The reaction mixture was diluted with water, and extracted with ethyl acetate. The organic layer was dried over magnesium sulfate, filtered, and concentrated in vacuo. The residue was purified by preparative HPLC eluting with a 5-95% acetonitrile/water gradient mixture to give the title compound as an oil (24 mg, 43%).

$^1$H NMR (CDCl$_3$) δ 0.85 (t, J=7.2 Hz, 6H), 1.64-1.87 (m, 4H), 3.17-3.27 (m, 1H), 3.99 (s, 3H), 6.94-7.00 (m, 2H), 7.09

(t, J=76 Hz, 1H), 7.38 (dd, J=2.4, 8.7 Hz, 1H), 7.65 (d, J=2.4 Hz, 1H), 7.68 (d, J=8.7 Hz, 1H).
MS Calcd.: 472. Found: 473 (M+H).

Example 149

2-(2-Bromo-4-chlorophenoxy)-7-(1-ethylpropyl)-4-(2-furyl)-1-methyl-1H-benzimidazole

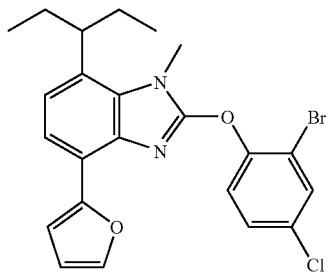

7-(1-Ethylpropyl)-4-(2-furyl)-1-methyl-1,3-dihydro-2H-benzimidazole-2-one

To a mixture of 4-bromo-7-(1-ethylpropyl)-1-methyl-1,3-dihydro-2H-benzimidazole-2-one (150 mg, 0.505 mmol) and 2-(tributhylstanyl)furan (361 mg, 1.01 mmol) in toluene (2 ml) was added tetrakis(triphenylphosphine)palladium(0) (117 mg, 0.101 mmol) and the mixture was refluxed for 3 h. After cooling, the solvent was evaporated in vacuo and the residue was diluted with ethyl acetate. The ethyl acetate solution was washed with aqueous saturated sodium bicarbonate and brine, dried over magnesium sulfate filtered and concentrated under vacuum. The residue was purified by preparative HPLC eluting with a 5-95% acetonitrile/water gradient mixture to give 81 mg (0.285 mmol, 56%) of the title compound.
¹H NMR (CDCl₃) δ 0.83 (t, J=7.5 Hz, 6H), 1.60-1.80 (m, 4H), 3.10-3.25 (m, 1H), 3.66 (s, 3H), 6.52 (dd, J=2.1, 3.3 Hz, 1H), 6.68 (d, J=3.3 Hz, 1H), 6.95 (d, J=8.1 Hz, 1H), 7.25 (d, J=8.4 Hz, 1H), 7.51 (d, J=2.1 Hz, 1H), 8.74 (s, 1H).
MS Calcd.: 284. Found: 285 (M+H).

2-Chloro-7-(1-ethylpropyl)-4-(2-furyl)-1-methyl-1H-benzimidazole

A mixture of 7-(1-ethylpropyl)-4-(2-furyl)-1-methyl-1,3-dihydro-2H-benzimidazole-2-one (79 mg, 0.278 mmol) in phosphorous oxychloride (0.78 ml, 8.33 mmol) was stirred at 120° C. for 2 h. The reaction was allowed to cool to room temperature and concentrated in vacuo. The residue was dissolved in ethyl acetate, washed with aqueous saturated sodium bicarbonate and brine. The organic layer was dried over magnesium sulfate, filtered and concentrated in vacuo. The residue was purified by chromatography on silica gel with a 1-30% ethyl acetate/n-hexane gradient mixture to give 44 mg (0.145 mmol, 52%) of the title compound.
¹H NMR (CDCl₃) δ 0.82 (t, J=7.5 Hz, 6H), 1.65-1.85 (m, 4H), 3.20-3.35 (m, 1H), 4.01 (s, 3H), 6.54 (dd, J=1.8, 3.3 Hz, 1H), 7.15 (d, J=7.8 Hz, 1H), 7.40-7.50 (m, 2H), 7.67 (d, J=7.8 Hz, 1H).
MS Calcd.: 302. Found: 303 (M+H), 305.

2-(2-Bromo-4-chlorophenoxy)-7-(1-ethylpropyl)-4-(2-furyl)-1-methyl-1H-benzimidazole A mixture of 2-chloro-7-(1-ethylpropyl)-4-(2-furyl)-1-methyl-1H-benzimidazole (42 mg, 0.139 mmol), 2-bromo-4-chlorophenol (87 mg, 0.417 mmol) and potassium carbonate (58 mg, 0.417 mmol) was heated at 120° C. for 18 h under an argon atmosphere. The mixture was diluted with water. The aqueous solution was extracted with ethyl acetate. The extract was washed with brine, dried over sodium sulfate, filtered and concentrated in vacuo. The residue was purified by column chromatography on silica gel with a 1-20% ethyl acetate/n-hexane gradient mixture to give 45 mg (0.0950 mmol, 68%) of the title compound) as a colorless crystal.
mp 159-162° C.
¹H NMR (CDCl₃) δ 0.86 (t, J=7.5 Hz, 6H), 1.70-1.85 (m, 4H), 3.20-3.35 (m, 1H), 4.01 (s, 3H), 6.47 (dd, J=1.5, 3.3 Hz, 1H), 7.09 (d, J=8.1 Hz, 1H), 7.20 (d, J=3.3 Hz, 1H), 7.35-7.45 (m, 2H), 7.64 (d, J=8.1 Hz, 1H), 7.66 (s, 1H), 7.85 (d, J=9.0 Hz, 1H).
MS Calcd.: 472. Found: 473 (M+H), 475.

Example 150

2-(2-Bromo-4-chlorophenoxy)-7-(1-ethylpropyl)-1-methyl-1H-benzimidazole-4-carbonitrile

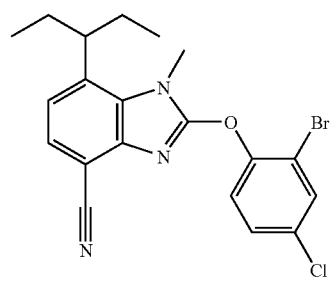

7-(1-Ethylpropyl)-1-methyl-2-oxo-2,3-dihydro-1H-benzimidazole-4-carbonitrile

A mixture of 4-bromo-7-(1-ethylpropyl)-1-methyl-1,3-dihydro-2H-benzimidazol-2-one (300 mg, 1.01 mmol) and copper cyanide (116 mg, 1.30 mmol) in 1-methyl-2-pyrrolidone (3 mL) was irradiated by microwave (200 w) at 150° C. for 1 h. After cooling, to the reaction mixture was diluted with saturated sodium bicarbonate, and extracted with ethyl acetate. The extract was dried over magnesium sulfate, filtered, and concentrated in vacuo. The residue was washed with 50% diisopropyl ether/n-hexane to give the title compound (209 mg, 86%).
¹H NMR (CDCl₃) δ 0.81 (t, J=7.8 Hz, 6H), 1.57-1.83 (m, 4H), 3.18-3.27 (m, 1H), 3.67 (s, 3H), 6.98 (d, J=8.4 Hz, 1H), 7.27 (d, J=8.4 Hz, 1H), 9.51 (s, 1H).
MS Calcd.: 243. Found: 244 (M+H).

2-Chloro-7-(1-ethylpropyl)-1-methyl-1H-benzimidazole-4-carbonitrile

A mixture of 7-(1-ethylpropyl)-1-methyl-1,3-dihydro-2H-benzimidazol-2-one (3.80 g, 15.6 mmol) and phosphorus oxychloride (50 mL) was heated at 120° C. for 6 h. After cooling, the reaction mixture was poured into a crushed ice and stirred for 30 min, neutralized with sodium hydrogen carbonate and extracted with ethyl acetate. The organic layers were dried over magnesium sulfate, filtered, and concentrated in vacuo. The residue was washed with diisopropyl ether to give the title compound (3.76 g, 92%).

¹H NMR (CDCl₃) δ 0.83 (t, J=7.5 Hz, 6H), 1.65-1.91 (m, 4H), 3.27-3.36 (m, 1H), 4.05 (s, 3H), 7.18 (d, J=8.4 Hz, 1H), 7.58 (d, J=8.4 Hz, 1H).
MS Calcd.: 261. Found: 262 (M+H).

2-(2-Bromo-4-chlorophenoxy)-7-(1-ethylpropyl)-1-methyl-1H-benzimidazole-4-carbonitrile A mixture of 2-chloro-7-(1-ethylpropyl)-1-methyl-1H-benzimidazole-4-carbonitrile (250 mg, 0.957 mmol), 2-bromo-4-chlorophenol (595 mg, 2.87 mmol), potassium carbonate (397 mg, 2.87 mmol) and 1-methyl-2-pyrrolidone (0.5 ml) was stirred at 120° C. for 12 h under nitrogen atmosphere. The mixture was diluted with water, extracted with ethyl acetate, and washed with brine. The organic layer was dried over magnesium sulfate, and concentrated in vacuo. The residue was purified by chromatography on silica gel with a 2-30% ethyl acetate/n-hexane gradient mixture and crystallized from methanol to afford the title compound as colorless crystals (134 mg, 32%).
mp 136-137° C.
¹H NMR (CDCl₃) δ 0.85 (t, J=7.5 Hz, 6H), 1.65-1.90 (m, 4H), 3.25-3.35 (m, 1H), 4.02 (s, 3H), 7.07 (d, J=8.1 Hz, 1H), 7.39 (dd, J=2.4, 8.7 Hz, 1H), 7.47 (d, J=8.1 Hz, 1H), 7.65 (d, J=2.4 Hz, 1H), 7.81 (d, J=7.8 Hz, 1H)
MS Calcd.: 431. Found: 432 (M+H), 434.

Example 151

2-(2,4-Dichloro-6-methylphenoxy)-7-(1-ethylpropyl)-1-methyl-1H-benzimidazole-4-carbonitrile

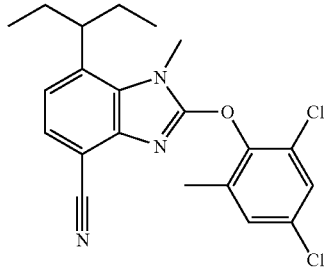

Example 151 was prepared in the similar method described in Example 150.
mp 192-192° C.
¹H NMR (CDCl₃) δ 0.86 (t, J=7.2 Hz, 6H), 1.65-1.90 (m, 4H), 2.31 (s, 3H), 3.20-3.35 (m, 1H), 4.01 (s, 3H), 7.04 (d, J=8.4 Hz, 1H), 7.22 (d, J=2.4 Hz, 1H), 7.32 (d, J=2.4 Hz, 1H), 7.43 (d, J=8.4 Hz, 1H).
MS Calcd.: 401. Found: 402 (M+H), 404.

Example 152

2-[(4-Chloro-2-methoxy-6-methylphenyl)amino]-7-(1-ethylpropyl)-1-methyl-1H-benzimidazole-4-carbonitrile

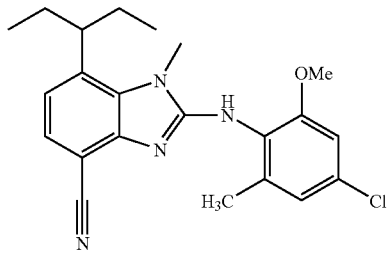

A mixture of 2-chloro-7-(1-ethylpropyl)-1-methyl-1H-benzimidazole-4-carbonitrile (1.00 g, 3.82 mmol), 4-chloro-2-methoxy-6-methylaniline (1.97 g, 11.50 mmol) and 1-methyl-2-pyrrolidone (0.5 ml) was heated at 130° C. for 48 h. After cooling, the reaction mixture was diluted with aqueous saturated sodium hydrogen carbonate. The mixture was extracted with ethyl acetate, dried over magnesium sulfate and concentrated in vacuo. The residue was purified by column chromatography on silica gel to give the title compound as a white powder (670 mg, 44%).
¹H NMR (CDCl₃) δ 0.83 (t, J=7.5 Hz, 6H), 1.64-1.85 (m, 4H), 2.20 (s, 3H), 3.17-3.27 (m, 1H), 3.79 (s, 6H), 6.13 (s, 1H), 6.78 (d, J=2.1 Hz, 1H), 6.89 (d, J=2.1 Hz, 1H), 6.94 (d, J=8.1 Hz, 1H), 7.37 (d, J=8.1 Hz, 1H). MS Calcd.: 396. Found: 397 (M+H). mp. 223-225° C.

Example 153

Methyl 2-(2,4-dichloro-6-methylphenoxy)-7-(1-ethylpropyl)-1-methyl-1H-benzimidazole-4-carboxylate

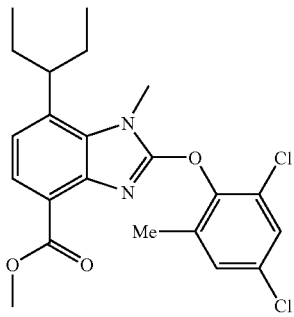

Methyl 7-(1-ethylpropyl)-1-methyl-2-oxo-2,3-dihydro-1H-benzimidazole-4-carboxylate A mixture of 7-(1-ethylpropyl)-1-methyl-2-oxo-2,3-dihydro-1H-benzimidazole-4-carbonitrile (1.50 g, 6.17 mmol), potassium hydroxide (20.0 g, 356 mmol), water (30 ml) and ethanol (30 ml) was heated under reflux for 48 h. The reaction mixture was concentrated in vacuo. The residue was diluted with ethyl acetate and 2N hydrochloric acid was added and extracted. The extracts were washed with water, dried over magnesium sulfate and concentrated in vacuo to give crude carboxylic acid. Trimethyl orthoacetate (10 ml) and toluene (10 ml) were added to the residue and heated at 100° C. for 6 h. The reaction mixture was concentrated in vacuo. The residue was purified by column chromatography on silica gel with a 35% ethyl acetate/n-hexane to give 1.31 g (4.74 mmol, 77%) of the title compound as a white powder.
¹H NMR (CDCl₃) δ 0.81 (t, J=7.44 Hz, 6H), 1.57-1.88 (m, 4H), 3.15-3.31 (m, 1H), 3.65 (s, 3H), 3.95 (s, 3H), 6.96 (d, J=8.48 Hz, 1H), 7.62 (d, J=8.67 Hz, 1H), 9.21 (s, 1H).
MS: Calcd.: 276. Found: 277 (M+H).

Methyl 2-chloro-7-(1-ethylpropyl)-1-methyl-1H-benzimidazole-4-carboxylate

A mixture of methyl 7-(1-ethylpropyl)-1-methyl-2-oxo-2,3-dihydro-1H-benzimidazole-4-carboxylate (1.30 g, 4.70 mmol) and phosphoryl chloride (10 ml) was heated at 100° C. for 3 h. The mixture was diluted with toluene and concentrated in vacuo to remove excess reagent. The residue was diluted with aqueous saturated sodium bicarbonate and extracted with ethyl acetate. The extracts were washed with water, dried over magnesium sulfate and concentrated in vacuo. The residue was purified by chromatography on column silica gel with a 10% ethyl acetate/n-hexane to give 1.18 g (4.00 mmol, 85%) of the title compound as a colorless oil.
¹H NMR (CDCl₃) δ 0.82 (t, J=7.35 Hz, 6H), 1.64-1.91 (m, 4H), 3.27-3.40 (m, 1H), 4.01 (s, 3H), 4.05 (s, 3H), 7.19 (d, J=8.10 Hz, 1H), 7.92 (d, J=8.29 Hz, 1H).

Methyl 2-(2,4-dichloro-6-methylphenoxy)-7-(1-ethylpropyl)-1-methyl-1H-benzimidazole-4-carboxylate A mixture of methyl 2-chloro-7-(1-ethylpropyl)-1-methyl-1H-benzimidazole-4-carboxylate (1.15 g, 3.90 mmol), 4,6-dichloro-o-cresol (2.07 g, 11.70 mmol), potassium carbonate (2.16 g, 15.60 mmol) and N,N-dimethylformamide (15 ml) was heated at 110° C. for 5 h. The residue was diluted with aqueous saturated sodium bicarbonate and extracted with ethyl acetate. The extracts were washed with water, dried over magnesium sulfate and concentrated in vacuo. The residue was purified by column chromatography on alumina with a 15% ethyl acetate/n-hexane to give 1.41 g (3.24 mmol, 83%) of the title compound as a white powder.
mp 177-178° C.
¹H NMR (CDCl₃) δ 0.86 (t, J=7.44 Hz, 6H), 1.65-1.92 (m, 4H), 2.36 (s, 3H), 3.25-3.39 (m, 1H), 3.84 (s, 3H), 4.03 (s, 3H) 7.06 (d, J=8.29 Hz, 1H), 7.21 (d, J=1.88 Hz, 1H), 7.30 (d, J=2.64 Hz, 1H), 7.79 (d, J=8.29 Hz, 1H).
MS: Calcd.: 435. Found: 436 (M+H).

Example 154

[2-(2,4-Dichloro-6-methylphenoxy)-7-(1-ethylpropyl)-1-methyl-1H-benzimidazol-4-yl]methanol

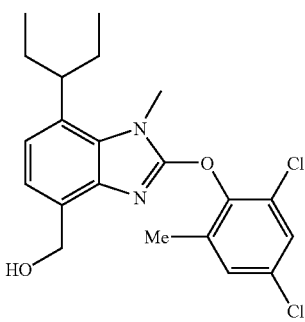

A mixture of methyl 2-(2,4-dichloro-6-methylphenoxy)-7-(1-ethylpropyl)-1-methyl-1H-benzimidazole-4-carboxylate (1.00 g, 2.30 mmol), lithium borohydride (100 mg, 4.60 mmol) and tetrahydrofuran (20 ml) was heated at 55° C. for 1 h. The reaction mixture was concentrated in vacuo. The residue was diluted with aqueous saturated sodium bicarbonate and extracted with ethyl acetate. The extracts were washed with water, dried over magnesium sulfate and concentrated in vacuo. The residue was purified by column chromatography on silica gel with a 30% ethyl acetate/n-hexane to give 920 mg (2.26 mmol, 98%) of the title compound as a white powder.
mp 141-143° C.
¹H NMR (CDCl₃) δ 0.87 (t, J=7.35 Hz, 6H), 1.66-1.88 (m, 4H), 2.29 (s, 3H), 3.16-3.30 (m, 1H), 3.90 (d, J=6.31 Hz, 1H), 3.99 (s, 3H), 4.85 (d, J=6.22 Hz, 2H), 6.98 (s, 2H), 7.20 (d, J=1.70 Hz, 1H), 7.32 (d, J=2.45 Hz, 1H).
MS: Calcd.: 407. Found: 408 (M+H).

Example 155

2-(2,4-Dichloro-6-methylphenoxy)-7-(1-ethylpropyl)-1-methyl-1H-benzimidazole-4-carbaldehyde

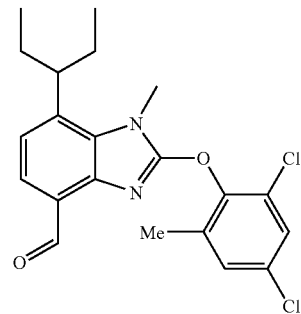

A mixture of [2-(2,4-dichloro-6-methylphenoxy)-7-(1-ethylpropyl)-1-methyl-1H-benzimidazol-4-yl]methanol (100 mg, 0.25 mmol), manganese(IV) oxide (428 mg, 4.92 mmol) and tetrahydrofuran (5 ml) was stirred at room temperature for 16 h. The reaction mixture was concentrated in vacuo. The residue was purified by column chromatography on alumina with a 50% ethyl acetate/n-hexane to give 93 mg (0.23 mmol, 93%) of the title compound as a white powder.
mp 148-149° C.
¹H NMR (CDCl₃) δ 0.87 (t, J=7.44 Hz, 6H), 1.70-1.93 (m, 4H), 2.32 (s, 3H), 3.25-3.39 (m, 1H), 4.04 (s, 3H), 7.11 (d, J=8.29 Hz, 1H), 7.24 (d, J=1.88 Hz, 1H), 7.35 (d, J=2.45 Hz, 1H), 7.72 (d, J=8.10 Hz, 1H), 10.55 (s, 1H).

Example 156

2-(2,4-Dichloro-6-methylphenoxy)-7-(1-ethylpropyl)-1-methyl-4-(pyrrolidin-1-ylmethyl)-1H-benzimidazole

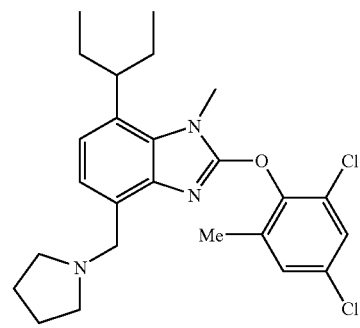

To a mixture of 2-(2,4-dichloro-6-methylphenoxy)-7-(1-ethylpropyl)-1-methyl-1H-benzimidazole-4-carbaldehyde (93 mg, 0.23 mmol), pyrrolidine (33 mg, 0.46 mmol), acetic acid (0.5 ml) and ethyl acetate (1.5 ml) was added sodium triacetoxyborohydride (244 mg, 1.15 mmol) and the reaction mixture was stirred at room temperature for 1 h. The residue was diluted with aqueous saturated sodium bicarbonate and extracted with ethyl acetate. The extracts were washed with water, dried over magnesium sulfate and concentrated in vacuo. The residue was purified by column chromatography on alumina with a 5% ethyl acetate/n-hexane to give 100 mg (0.22 mmol, 94%) of the title compound as a white powder.

mp 107-108° C.

$^1$H NMR (CDCl$_3$) δ 0.87 (t, J=7.35 Hz, 6H), 1.65-1.86 (m, 8H), 2.30 (s, 3H), 2.47-2.59 (m, 4H), 3.20-3.26 (m, 1H), 3.83 (s, 2H), 3.97 (s, 3H), 6.98 (d, J=7.91 Hz, 1H), 7.17 (d, J=7.91 Hz, 1H), 7.21 (d, J=1.88 Hz, 1H), 7.32 (d, J=2.45 Hz, 1H).

MS: Calcd.: 460. Found: 461 (M+H).

Example 157

N-{[2-(2,4-Dichloro-6-methylphenoxy)-7-(1-ethylpropyl)-1-methyl-1H-benzimidazol-4-yl]methyl}-N-methylethanamine

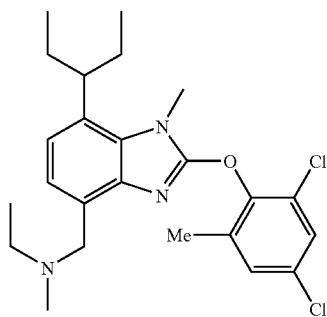

To a mixture of 2-(2,4-dichloro-6-methylphenoxy)-7-(1-ethylpropyl)-1-methyl-1H-benzimidazole-4-carbaldehyde (120 mg, 0.296 mmol), methyl amine (2M tetrahydrofuran solution, 1.48 ml, 2.96 mmol), acetic acid (0.5 ml) and ethyl acetate (2.0 ml) was added sodium triacetoxyborohydride (314 mg, 1.48 mmol) and the reaction mixture was stirred at room temperature for 48 h. The residue was diluted with aqueous saturated sodium bicarbonate and extracted with ethyl acetate. The extracts were washed with water, dried over magnesium sulfate and concentrated in vacuo. The residue was purified by chromatography on alumina with a 5% ethyl acetate/n-hexane to give 93 mg (0.21 mmol, 70%) of the title compound as a white powder.

$^1$H NMR (CDCl$_3$) δ 0.87 (t, J=7.35 Hz, 6H), 1.04 (t, J=7.16 Hz, 3H), 1.65-1.87 (m, 4H), 2.18 (s, 3H), 2.29 (s, 3H), 2.42 (q, J=7.16 Hz, 2H), 3.16-3.31 (m, 1H), 3.72 (s, 2H), 3.97 (s, 3H), 6.98 (d, J=7.91 Hz, 1H), 7.14 (d, J=7.91 Hz, 1H), 7.18-7.23 (m, 1H), 7.31 (d, J=1.88 Hz, 1H).

MS: Calcd.: 448. Found: 449 (M+H).

Example 158

N-(4-Chloro-2-methoxy-6-methylphenyl)-7-(1-ethylpropyl)-1-methyl-4-(trifluoromethyl)-1H-benzimidazol-2-amine

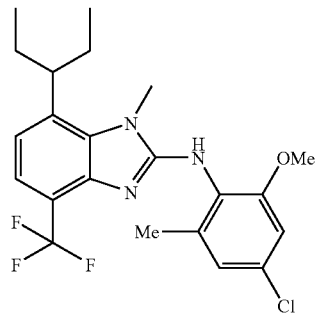

Methyl 2-nitro-4-(trifluoromethyl)benzoate

A mixture of 2-nitro-4-trifluoromethylbenzoic acid (23.5 g, 0.10 mol), trimethyl orthoacetate (60.1 g, 0.50 mol) and toluene (60 ml) was heated at 80° C. for 16 h. The reaction mixture was concentrated in vacuo. Toluene was added and concentrated again to remove excess reagent. The residue was purified by column chromatography on silica gel with a 1-10% ethyl acetate/n-hexane gradient mixture to give 24.9 g (0.50 mol 100%) of the title compound as a colorless oil.

$^1$H NMR (CDCl$_3$) δ: 3.97 (s, 3H), 7.87-7.90 (m, 1H), 7.95-7.97 (m, 1H), 8.22 (s, 1H).

Methyl 2-amino-4-(trifluoromethyl)benzoate

A mixture of methyl 2-nitro-4-(trifluoromethyl)benzoate (2.49 g 0.01 mol), sodium hydrosulfite (8.71 g, 0.05 mol), ethanol (20 ml) and water (20 ml) was heated at 50° C. for 3 h. Water was added and extracted with ethyl acetate. The extracts were washed with water, dried over magnesium sulfate and concentrated in vacuo. The residue was purified by column chromatography on silica gel with a 5% ethyl acetate/n-hexane to give 1.46 g (6.67 mmol 67%) of the title compound as a white powder.

$^1$H NMR (CDCl$_3$) δ 3.90 (s, 3H), 5.50-6.20 (brs, 2H), 6.85 (d, J=8.48 Hz, 1H), 6.90 (s, 1H), 7.95 (d, J=8.48 Hz, 1H).

MS Calcd.: 219. Found: 220 (M+H).

Methyl 2-(acetylamino)-4-(trifluoromethyl)benzoate

A mixture of methyl 2-amino-4-(trifluoromethyl)benzoate (8.00 g, 0.036 mol), acetic anhydride (11.18 g, 0.109 mol), pyridine (8.62 g, 0.109 mol) and chloroform (20 ml) was stirred at room temperature for 48 h. The reaction mixture was concentrated in vacuo. The residue was diluted with water and extracted with ethyl acetate. The extracts were washed with 1N hydrochloric acid and water, dried over magnesium sulfate and concentrated in vacuo. The residue was purified by column chromatography on silica gel with a 50% ethyl acetate/n-hexane to give 8.10 g (0.031 mol 86%) of the title compound as a white powder.

mp 86-87° C.

¹H NMR (CDCl₃) δ 2.26 (s, 3H), 3.97 (s, 3H), 7.32 (dd, J=1.41, 8.38 Hz, 1H), 8.14 (d, J=8.29 Hz, 1H), 9.08 (s, 1H), 11.11 (s, 1H).
MS Calcd.: 261. Found: 262 (M+H).

Methyl 2-(acetylamino)-3-nitro-4-(trifluoromethyl) benzoate

To an ice-cooled nitric acid (fuming) (20 ml) was added methyl 2-(acetylamino)-4-(trifluoromethyl)benzoate (7.30 g, 0.028 mol) portionwise and stirred for 30 min. The reaction mixture was poured into ice-water and extracted with ethyl acetate. The extracts were washed with aqueous saturated sodium bicarbonate and water, dried over magnesium sulfate and concentrated in vacuo. The residue was purified by column chromatography on silica gel with a 30% ethyl acetate/n-hexane to give 3.20 g (0.010 mol, 38%) of the title compound as a yellow powder.
¹H NMR (CDCl₃) δ 2.21 (s, 3H), 3.98 (s, 3H), 7.68 (d, J=8.29 Hz, 1H), 8.19 (d, J=8.29 Hz, 1H), 9.10 (s, 1H).

Methyl 2-amino-3-nitro-4-(trifluoromethyl)benzoate

A mixture of methyl 2-(acetylamino)-3-nitro-4-(trifluoromethyl)benzoate (1.00 g, 3.27 mmol) and 10% hydrochloric acid in methanol solution (10 ml) was heated at 55° C. for 16 h. The reaction mixture was concentrated in vacuo. The residue was diluted with aqueous saturated sodium bicarbonate and extracted with ethyl acetate. The extracts were washed with water, dried over magnesium sulfate and concentrated in vacuo. The residue was purified by column chromatography on silica gel with a 30% ethyl acetate/n-hexane to give 780 mg (0.030 mol 90%) of the title compound as a yellow powder.
¹H NMR (CDCl₃) δ3.95 (s, 3H), 6.90-7.15 (brs, 2H), 6.99 (d, J=8.29 Hz, 1H), 8.16 (d, J=8.29 Hz, 1H).

Methyl 2,3-diamino-4-(trifluoromethyl)benzoate

To a stirring solution of methyl 2-amino-3-nitro-4-(trifluoromethyl)benzoate (5.80 g, 0.022 mol), ammonium formate (30.0 g, 0.476 mol) in ethanol (300 ml) was added 10% palladium on carbon (500 mg) at room temperature and stirred for 2 h. Insoluble was filtered off and filtrates were concentrated in vacuo. The residue was diluted with water and extracted with ethyl acetate. The extracts were washed with water, dried over magnesium sulfate and concentrated in vacuo. The residue was purified by column chromatography on silica gel with a 20% ethyl acetate/n-hexane to give 5.10 g (0.022 mol, 99%) of the title compound as a yellow powder.
¹H NMR (CDCl₃) δ 3.87 (brs, 2H), 3.90 (s, 3H), 5.68 (brs, 2H), 6.88 (d, J=8.67 Hz, 1H), 7.47 (d, J=8.67 Hz, 1H).
MS Calcd.: 234. Found: 235 (M+H).

Methyl 2-oxo-7-(trifluoromethyl)-2,3-dihydro-1H-benzimidazole-4-carboxylate

To a stirring solution of methyl 2,3-diamino-4-(trifluoromethyl)benzoate (5.10 g, 0.022 mol) and diisopropylethylamine (6.26 g, 0.048 mol) in toluene (50 ml) was added a solution of triphosgene (2.58 g, 0.0087 mol) in toluene (20 ml) dropwise and stirred at room temperature for 16 h. The reaction mixture was concentrated in vacuo. The residue was diluted with 1N hydrochloric acid and extracted with ethyl acetate and tetrahydrofuran. The extracts were washed with water, dried over magnesium sulfate and concentrated in vacuo. A solution of 50% diisopropylether/n-hexane was added to the residue and white precipitates were filtered, washed with same solvent to give 5.00 g (0.019 mol 87%) of the title as a white powder
mp. 281-283° C.
¹H NMR (DMSO-d₆) δ 3.92 (s, 3H) 7.32 (d, J=8.48 Hz, 1H), 7.61 (d, J=8.48 Hz, 1H), 11.23 (s, 1H), 11.63 (s, 1H).
MS Calcd.: 260. Found: 261 (M+H)

Methyl 3-methyl-2-oxo-7-(trifluoromethyl)-2,3-dihydro-1H-benzimidazole-4-carboxylate To a stirring mixture of methyl 2-oxo-7-(trifluoromethyl)-2,3-dihydro-1H-benzimidazole-4-carboxylate (2.34 g, 9.00 mmol), di-t-butyl dicarbonate (4.32 g, 20.0 mmol) and N,N-dimethylformamide (240 ml) was added 60% sodium hydride (800 mg, 20.0 mmol) portionwise and stirred at 50° C. for 2 h. The reaction mixture was poured into 1N hydrochloric acid and extracted with ethyl acetate. The extracts were washed with aqueous saturated sodium bicarbonate and water, dried over magnesium sulfate and concentrated in vacuo. A solution of 50% diisopropylether/n-hexane was added to the residue and white precipitates (starting materials) were filtered off. The filtrates were concentrated in vacuo to give crude 1-tert-butyl 4-methyl 2-oxo-7-(trifluoro-methyl)-2,3-dihydro-1H-benzimidazole-1,4-dicarboxylate as a colorless oil.

To a stirring mixture of obtained crude dicarboxylate, methyl iodide (2.82 g, 20.0 mmol) and N,N-dimethylformamide (10 ml) was added 60% sodium hydride (800 mg, 20.0 mmol) portionwise and stirred at room temperature for 30 min. The reaction mixture was poured into 1N hydrochloric acid and extracted with ethyl acetate. The extracts were washed with aqueous saturated sodium bicarbonate and water, dried over magnesium sulfate and concentrated in vacuo to give crude 1-tert-butyl 4-methyl 3-methyl-2-oxo-7-(trifluoromethyl)-2,3-dihydro-1H-benzimidazole-1,4-dicarboxylate as a colorless oil.

A mixture of obtained crude 1,4-dicarboxylate and trifluoroacetic acid (5 ml) was stirred at 50° C. for 10 min and concentrated in vacuo. The residue was diluted with aqueous saturated sodium bicarbonate and extracted with ethyl acetate. The extracts were washed with water, dried over magnesium sulfate and concentrated in vacuo. The residue was purified by column chromatography on silica gel with a 20% ethyl acetate/n-hexane to give 1.13 g (4.12 mmol 46%) of the title compound as a white powder.
¹H NMR (CDCl₃) δ 3.57 (s, 3H), 3.99 (s, 3H), 7.29 (d, J=8.48 Hz, 1H), 7.54 (dd, J=0.75, 8.48 Hz, 1H), 9.36 (brs, 1H).
MS Calcd.: 274. Found: 275 (M+H).

7-(1-Ethylprop-1-en-1-yl)-1-methyl-4-(trifluoromethyl)-1,3-dihydro-2H-benzimidazol-2-one To an ice-cooled solution of, methyl 3-methyl-2-oxo-7-(trifluoromethyl)-2,3-dihydro-1H-benzimidazole-4-carboxylate (2.80 g, 10.2 mmol) in tetrahydrofuran (30 ml) was added a solution of 3M ethylmagnesium bromide in diethylether (13.6 ml, 40.8 mmol) dropwise and stirred at 45° C. for 16 h. Methanol and water were carefully added to decompose excess reagent. 2N hydrochloric acid was added and extracted with ethyl acetate. The extracts were washed with aqueous saturated sodium bicarbonate and water, dried over magnesium sulfate and concentrated in vacuo. Ethanol (40 ml) and conc. hydrochloric acid (10 ml) were added to the residue and the resulting mixture was heated at 80° C. for 6 h. The reaction mixture was concentrated in vacuo. Aqueous saturated sodium bicarbonate was added to the residue and extracted with ethyl acetate. The extracts were washed with water, dried over magnesium sulfate and concentrated in vacuo. The residue was purified by chromatography on silica gel with a 20% ethyl acetate/n-hexane to give 609 mg (2.14 mmol, 21%, cis/trans=3/1) of the title compound as a white powder.

$^1$H NMR (CDCl$_3$) δ 0.97 (t, J=7.50 Hz, 3H×0.75), 1.06 (t, J=7.44 Hz, 3H×0.25), 1.39-1.45 (m, 3H×0.25), 1.83 (d, J=6.78 Hz, 3H×0.75), 2.19-2.68 (m, 2H), 3.44 (s, 3H), 5.49 (q, J=6.78 Hz, 1H×0.75), 5.74 (q, J=6.78 Hz, 1H×0.25), 6.80 (d, J=8.10 Hz, 1H×0.25), 6.86 (d, J=8.10 Hz, 1H×0.75), 7.19 (d, J=8.29 Hz, 1H×0.75), 7.24 (d, J=8.28 Hz, 1H×0.25), 9.07 (s, 1H).

MS Calcd.: 284. Found: 285 (M+H).

7-(1-Ethylpropyl)-1-methyl-4-(trifluoromethyl)-1,3-dihydro-2H-benzimidazol-2-one A mixture of 7-(1-ethylprop-1-en-1-yl)-1-methyl-4-(trifluoromethyl)-1,3-dihydro-2H-benzimidazol-2-one (486 mg, 1.71 mmol), 10% palladium on carbon (200 mg) and acetic acid (5 ml) was hydrogenated under 5 atom of hydrogen at 50° C. for 2 h. Catalyst was filtered off and filtrates were concentrated in vacuo. Aqueous saturated sodium bicarbonate was added to the residue and extracted with ethyl acetate. The extracts were washed with water, dried over magnesium sulfate and concentrated in vacuo. The residue was purified by recrystallization from diisopropylether/n-hexane to give 350 mg (1.22 mmol, 72%) of the title compound as a white powder.

mp. 205-206° C.
$^1$H NMR (CDCl$_3$) δ 0.82 (t, J=7.44 Hz, 6H), 1.58-1.88 (m, 4H), 3.14-3.36 (m, 1H), 3.67 (s, 3H), 7.02 (d, J=8.48 Hz, 1H), 7.21-7.27 (m, 1H), 8.92 (brs, 1H).

MS Calcd.: 286. Found: 287 (M+H).

2-Chloro-7-(1-ethylpropyl)-1-methyl-4-(trifluoromethyl)-1H-benzimidazole

A mixture of 7-(1-ethylpropyl)-1-methyl-4-(trifluoro-methyl)-1,3-dihydro-2H-benzimidazol-2-one (310 mg, 1.08 mmol) and phosphoryl chloride (5 ml) was heated at 110° C. for 1 h and concentrated in vacuo. Toluene was added and concentrated again to remove excess reagent. Aqueous saturated sodium bicarbonate was added to the residue and extracted with ethyl acetate. The extracts were washed with water, dried over magnesium sulfate and concentrated in vacuo. The residue was purified by column chromatography on silica gel with a 20% ethyl acetate/n-hexane to give 300 mg (0.99 mmol, 91%) of the title compound as a colorless oil.

$^1$H NMR (CDCl$_3$) δ 0.83 (t, J=7.50 Hz, 6H), 1.65-1.91 (m, 4H), 3.24-3.40 (m, 1H), 4.05 (s, 3H), 7.19 (d, J=7.91 Hz, 1H), 7.53 (d, J=8.10 Hz, 1H).

MS Calcd.: 304. Found: 305 (M+H).

N-(4-Chloro-2-methoxy-6-methylphenyl)-7-(1-ethylpropyl)-1-methyl-4-(trifluoromethyl)-1H-benzimidazol-2-amine A mixture of 2-chloro-7-(1-ethylpropyl)-1-methyl-4-(trifluoromethyl)-1H-benzimidazole (290 mg, 0.95 mmol), 4-chloro-2-methoxy-6-methylaniline (491 mg, 2.86 mmol) and N-methyl-2-pyrrolidinone (3 drops) was heated at 110° C. for 72 h. Aqueous saturated sodium bicarbonate was added to the residue and extracted with ethyl acetate. The extracts were washed with water, dried over magnesium sulfate and concentrated in vacuo. The residue was purified by chromatography on silica gel with a 10% ethyl acetate/n-hexane and recrystallized from diisopropylether/n-hexane to give 140 mg (0.32 mmol, 34%) of the title compound as a white powder.

mp. 187-188° C.
$^1$H NMR (CDCl$_3$) δ 0.83 (t, J=7.35 Hz, 6H), 1.63-1.89 (m, 4H), 2.18 (s, 3H), 3.20-3.30 (m, 1H), 3.74 (s, 3H), 3.78 (s, 3H), 6.18 (s, 1H), 6.78 (s, 1H), 6.88 (d, J=2.07 Hz, 1H), 6.97 (d, J=8.29 Hz, 1H), 7.36 (d, J=8.29 Hz, 1H).

MS Calcd.: 440. Found: 441 (M+H).

Example 159

N-(2-Bromo-4-chlorophenyl)-7-(1-ethylpropyl)-1-methyl-4-(trifluoromethyl)-1H-benzimidazol-2-amine

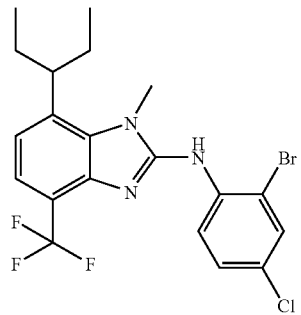

Example 159 was prepared in the similar method described in Example 158.

mp. 151-152° C.
$^1$H NMR (CDCl$_3$) δ 0.84 (t, J=7.44 Hz, 6H), 1.65-1.91 (m, 4H), 3.19-3.34 (m, 1H), 3.87 (s, 3H), 6.93 (s, 1H), 7.07 (d, J=8.10 Hz, 1H), 7.34 (dd, J=2.45, 8.85 Hz, 1H), 7.45 (d, J=7.35 Hz, 1H), 7.56 (d, J=2.45 Hz, 1H), 8.29 (d, J=8.67 Hz, 1H).

MS Calcd.: 474. Found: 475 (M+H).

Example 160

2-(2,4-Dichloro-6-methylphenoxy)-7-(1-ethylpropyl)-1-methyl-4-(trifluoromethyl)-1H-benzimidazole

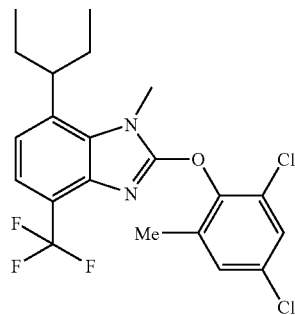

A mixture of 2-chloro-7-(1-ethylpropyl)-1-methyl-4-(trifluoromethyl)-1H-benzimidazole (304 mg, 1.00 mmol), 4,6-dichloro-o-cresol (531 mg, 3.00 mmol), potassium carbonate (553 mg, 4.0 mmol) and N,N-dimethylformamide (5 ml) was heated at 110° C. for 48 h. Aqueous saturated sodium bicarbonate was added to the residue and extracted with ethyl acetate. The extracts were washed with water, dried over magnesium sulfate and concentrated in vacuo. The residue was purified by column chromatography on silica gel with a 10% ethyl acetate/n-hexane and recrystallization from diisopropylether/n-hexane to give 290 mg (0.65 mmol, 65%) of the title compound as a white powder.

mp. 149-151° C.

$^1$H NMR (CDCl$_3$) δ 0.87 (t, J=7.35 Hz, 6H), 1.66-1.91 (m, 4H), 2.31 (s, 3H), 3.24-3.37 (m, 1H), 4.02 (s, 3H), 7.05 (d, J=8.10 Hz, 1H), 7.21 (d, J=1.88 Hz, 1H), 7.31 (d, J=2.45 Hz, 1H), 7.39 (d, J=8.10 Hz, 1H).

MS Calcd.: 445. Found: 446 (M+H).

Example 161

2-(2-Bromo-4-chlorophenoxy)-7-(1-ethylpropyl)-1-methyl-4-(trifluoromethyl)-1H-benzimidazole

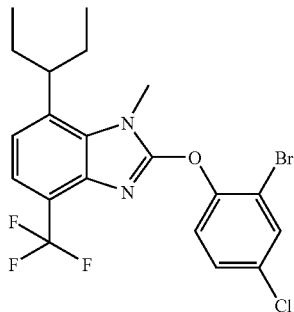

Example 161 was prepared in the similar method described in Example 160.

mp. 119-120° C.

$^1$H NMR (CDCl$_3$) δ 0.85 (t, J=7.44 Hz, 6H), 1.65-1.91 (m, 4H), 3.24-3.37 (m, 1H), 4.02 (s, 3H), 7.10 (d, J=8.10 Hz, 1H), 7.39 (dd, J=2.45, 8.85 Hz, 1H), 7.44 (d, J=8.29 Hz, 1H), 7.64 (d, J=2.45 Hz, 1H), 7.95 (d, J=9.04 Hz, 1H).

MS Calcd.: 475. Found: 476 (M+H).

Example 162

2-(2,4-Dichloro-6-methylphenoxy)-7-(3,5-diethyl-1H-pyrazol-1-yl)-1-methyl-1H-benzimidazole

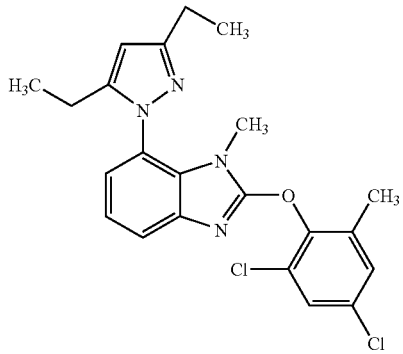

A suspension of 2-chloro-7-(3,5-diethyl-1H-pyrazol-1-yl)-1-methyl-1H-benzimidazole (92 mg, 0.318 mmol), 2,4-dichloro-6-methylphenol (114 mg, 0.643 mmol), potassium carbonate (89 mg, 0.643 mmol) in N,N-dimethylformamide (1.5 ml) was stirred at 90° C. for 5.5 days (2,4-dichloro-6-methylphenol and potassium carbonate were added in three equal portions each over 5.5 days). After cooling, the reaction mixture was diluted with water and extracted with ethyl acetate. The organic layer was washed with water and brine, dried over sodium sulfate and concentrated in vacuo. The residue was purified by column chromatography on silica gel eluting with a 10-25% ethyl acetate/n-hexane gradient mixture to give 107 mg (0.249 mmol, 78.3%) of the title compound as an oil. The oil was crystallized from hexane to give 70 mg (51%) as a pale yellow crystal.

mp: 115-119° C.

$^1$H NMR (CDCl$_3$) δ: 1.19 (3H, t, J=7.5 Hz), 1.32 (3H, t, J=7.5 Hz), 2.26 (3H, s), 2.50 (2H, q, J=7.5 Hz), 2.72 (2H, q, J=7.5 Hz), 3.23 (3H, s), 6.10 (1H, s), 7.09-7.19 (3H, m), 7.31 (1H, d, J=2.4 Hz), 7.57 (1H, d, J=6.9 Hz).

MS Calcd.: 428. Found: 429 (M+H), 431.

Example 163

3,5-Dichloro-4-{([7-(1-ethylpropyl)-4-methoxy-1-methyl-1H-benzimidazol-2-yl]oxy}-N,N-dimethylaniline

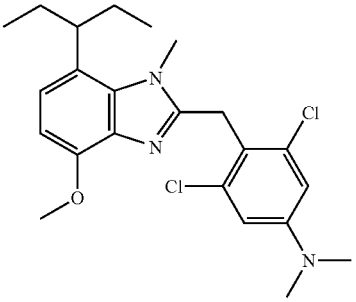

Example 163 was prepared in the similar method described in Example 145.

mp 176-177° C.

$^1$H NMR (CDCl$_3$) δ 0.86 (t, J=7.5 Hz, 6H), 1.65-1.85 (m, 4H), 2.94 (s, 6H), 3.15-3.25 (m, 1H), 3.89 (s, 3H), 3.97 (s, 3H), 6.63 (d, J=8.4 Hz, 1H), 6.63 (s, 2H), 6.91 (d, J=8.4 Hz, 1H).

MS Calcd.: 435. Found: 436 (M+H), 438.

Experiment 1

Measurement of Corticotropin-Releasing Factor (CRF) Binding Inhibitory Rate

A receptor binding experiment was carried out using a human CRF receptor expressing CHO cellular membrane fraction and ovine CRF, [$^{125}$I]-tyr$^0$ ($^{125}$I-CRF). 1000 nM of a test compound was incubated with 1 μg of human CRF receptor expressing CHO cellular membrane fraction and 50 pM of $^{125}$I-CRF in a binding assay buffer (50 mM Tris-HCl, 5 mM EDTA, 10 mM MgCl$_2$, 0.05% CHAPS, 0.1% BSA, 0.5 mM PMSF, 0.1 μg/ml pepstatin, 20 μg/ml leupeptin, pH 7.5). In addition, for measuring nonspecific binding (NSB), 0.1 μM unlabelled human Urocortin was incubated with 1 μg of human CRF receptor expressing CHO cellular membrane fraction and 50 pM of $^{125}$I-CRF in a binding assay buffer.

After a binding reaction was carried out at room temperature for 1.5 hour, the membrane was entrapped on a glass filter (UniFilter plate GF-C/Perkin Elmer) by suction filtration using a cell harvester (Perkin Elmer), and washed with ice-cooled 50 mM Tris-HCl (pH 7.5). After drying the glass filter, a liquid scintillation cocktail (Microscinti 0, Perkin Elmer) was added, and the radioactivity of $^{125}$I-CRF remaining on a glass filter was measured using Topcount (Perkin Elmer).

(TB−SB)/(TB−NSB)×100 (SB: radioactivity when a compound is added, TB: maximum binding radioactivity, NSB: nonspecific binding radioactivity) was calculated to obtain a binding inhibitory rate under the presence of 1,000 nM of each test substances. The IC$_{50}$ values were calculated by using GraphPad Prism software.

Binding inhibitory rates of respective compounds measured by the aforementioned method are shown in Table 8.

TABLE 8

| Example No. | Binding inhibitory rate (%) 1000 nM |
|---|---|
| 1 | >80 |
| 9 | >80 |
| 64 | >80 |
| 69 | >80 |
| 77 | >80 |
| 84 | >80 |
| 90 | >80 |
| 97 | >80 |
| 101 | >80 |
| 103 | >80 |

Values of IC$_{50}$ of respective compounds were measured by the aforementioned method, and are shown as A and B in Table 9. [A: less than 10 nM; B: 10-50 nM]

TABLE 9

| Example No. | IC$_{50}$ (nM) |
|---|---|
| 15 | B |
| 66 | B |
| 77 | B |
| 97 | A |
| 101 | A |
| 145 | A |

INDUSTRIAL APPLICABILITY

Compound (I) or (I') of the present invention has an excellent CRF antagonistic activity, and therefore useful as drugs for treating or preventing affective disorder, depression, anxiety, and the like.

The invention claimed is:

1. A compound represented by formula (I):

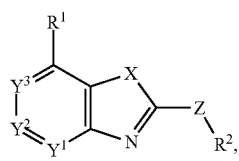

(I)

wherein R$^1$ is an acyclic branched C$_{3-7}$ alkyl optionally substituted with hydroxyl; a phenyl optionally substituted with a halogen, nitro, hydroxyl, C$_{1-6}$ alkoxy, amino, methyl, methylaminomethyl, ethyl or propyl; or a N-linked pyrrolyl or pyrazolyl each of which may be substituted with 1 to 3 substituents selected from the group consisting of C$_{1-6}$ alkyl and C$_{6-10}$ aryl;

R$^2$ is a phenyl which may be substituted with acetyl, propionyl, dimethylaminocarbonyl, methylaminocarbonyl, dimethylamino, methylamino, amino, halogen, methyl, ethyl, trifluoromethyl, methoxy, ethoxy or trifluoromethoxy;

X is —NR$^3$— (wherein R$^3$ is a C$_{1-8}$ alkyl optionally substituted with hydroxyl);

Y$^1$ is CR$^{3a}$, wherein R$^{3a}$ is a hydrogen, a halogen, a cyano, a C$_{1-3}$ alkyl optionally substituted with hydroxyl, or a C$_{1-3}$ alkoxy optionally substituted with halogen;

Y$^2$ is CR$^{3b}$, wherein R$^{3b}$ is a hydrogen;

Y$^3$ is CR$^{3c}$, wherein R$^{3c}$ is a hydrogen; and

Z is an oxygen or —NR$^4$—, wherein R$^4$ is a hydrogen; or a salt thereof.

2. The compound according to claim 1, wherein R$^1$ is an acyclic branched C$_{3-7}$ alkyl optionally substituted with hydroxyl.

3. The compound according to claim 1, wherein R$^1$ is a phenyl optionally substituted with a halogen, nitro, hydroxyl, C$_{1-6}$ alkoxy, amino, methyl, methylaminomethyl, ethyl or propyl.

4. The compound according to claim 1, wherein R$^1$ is a N-linked pyrrolyl or pyrazolyl each of which may be substituted with 1 to 3 substituents selected from the group consisting of C$_{1-6}$ alkyl and C$_{6-10}$ aryl.

5. The compound according to claim 1, wherein R$^3$ is methyl, ethyl or hydroxyethyl.

6. The compound according to claim 1, wherein R$^{3a}$ is hydrogen, chlorine, bromine, methoxy or methyl.

7. The compound according to claim 1, wherein R$^2$ is phenyl which is 2,4,6-trisubstituted, 2,4,5-trisubstituted or 2,4-disubstituted.

8. The compound according to claim 1 which is
N-(4-chloro-2-methoxy-6-methylphenyl)-7-(2-ethylphenyl)-1-methyl-1H-benzimidazol-2-amine,
N-(4-bromo-2-methoxy-6-methylphenyl)-7-(3,5-diethyl-1H-pyrazol-1-yl)-1-methyl-1H-benzimidazol-2-amine,
N-(4-bromo-2-methoxy-6-methylphenyl)-4-chloro-7-(1-ethylpropyl)-1-methyl-1H-benzimidazol-2-amine,
N-(4-chloro-2-methoxy-6-methylphenyl)-7-(1-ethylpropyl)-1,4-dimethyl-1H-benzimidazol-2-amine, or
4-chloro-N-(2,4-dichloro-6-methylphenyl)-7-(1-ethylpropyl)-1-methyl-1H-benzimidazol-2-amine, or a salt thereof.

9. A pharmaceutical composition which comprises the compound according to claim 1.

10. A CRF receptor antagonist which is the compound represented by the formula (I):

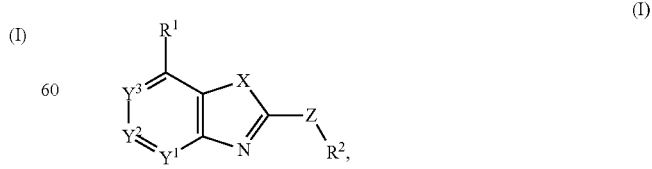

(I)

according to claim 1; or a salt thereof.

11. A method for treating affective disorder, depression, anxiety or irritable bowel syndrome, which comprises administering to a subject in need thereof an effective amount of the CRF receptor antagonist according to claim 10.

12. A pharmaceutical composition for treating affective disorder, depression, anxiety or irritable bowel syndrome, which comprises the CRF receptor antagonist according to claim 10.

13. The compound according to claim 1 which is 4-chloro-2-(2,4-dichloro-6-methylphenoxy)-7-(1-ethylpropyl)-1-methyl-1H-benzimidazole, or 2-(2,4-dichloro-6-methylphenoxy)-7-(1-ethylpropyl)-4-methoxy-1-methyl-1H-benzimidazole, or a salt thereof.

14. N-(4-chloro-2-methoxy-6-methylphenyl)-7-(2-ethylphenyl)-1-methyl-1H-benzimidazol-2-amine or a salt thereof.

15. N-(4-bromo-2-methoxy-6-methylphenyl)-7-(3,5-diethyl-1H-pyrazol-1-yl)-1-methyl-1H-benzimidazol-2-amine or a salt thereof.

16. N-(4-bromo-2-methoxy-6-methylphenyl)-4-chloro-7-(1-ethylpropyl)-1-methyl-1H-benzimidazol-2-amine or a salt thereof.

17. N-(4-chloro-2-methoxy-6-methylphenyl)-7-(1-ethylpropyl)-1,4-dimethyl-1H-benzimidazol-2-amine or a salt thereof.

18. 4-chloro-N-(2,4-dichloro-6-methylphenyl)-7-(1-ethylpropyl)-1-methyl-1H-benzimidazol-2-amine or a salt thereof.

19. 4-chloro-2-(2,4-dichloro-6-methylphenoxy)-7-(1-ethylpropyl)-1-methyl-1H-benzimidazole or a salt thereof.

20. 2-(2,4-dichloro-6-methylphenoxy)-7-(1-ethylpropyl)-4-methoxy-1-methyl-1H-benzimidazole or a salt thereof.

\* \* \* \* \*